(12) United States Patent
Bathe et al.

(10) Patent No.: US 7,585,650 B2
(45) Date of Patent: Sep. 8, 2009

(54) ALLELES OF THE ZWF GENE FROM CORYNEFORM BACTERIA

(75) Inventors: Brigitte Bathe, Salzkotten (DE); Natalie Schischka, Bielefeld (DE); Georg Thierbach, Bielefeld (DE)

(73) Assignee: Degussa AG, Dusseldorf (DE)

( * ) Notice: Subject to any disclaimer, the term of this patent is extended or adjusted under 35 U.S.C. 154(b) by 40 days.

(21) Appl. No.: 11/790,063

(22) Filed: Apr. 23, 2007

(65) Prior Publication Data

US 2007/0224666 A1 Sep. 27, 2007

Related U.S. Application Data

(62) Division of application No. 11/284,416, filed on Nov. 22, 2005, now abandoned.

(60) Provisional application No. 60/709,094, filed on Aug. 18, 2005.

(30) Foreign Application Priority Data

Mar. 24, 2005 (DE) .................. 10 2005 013 676

(51) Int. Cl.
  *C12P 13/04* (2006.01)
  *C12P 13/22* (2006.01)
  *C12P 13/08* (2006.01)
  *C12N 1/20* (2006.01)
  *C07H 21/04* (2006.01)

(52) U.S. Cl. .................... 435/106; 435/252.3; 435/108; 435/115; 435/320.1; 536/23.2

(58) Field of Classification Search .................... None
See application file for complete search history.

(56) References Cited

U.S. PATENT DOCUMENTS

| | | | |
|---|---|---|---|
| 4,601,893 A | 7/1986 | Cardinal | 424/15 |
| 5,175,108 A | 12/1992 | Bachmann et al. | 435/252.32 |
| 5,965,391 A | 10/1999 | Reinscheid et al. | 435/69.1 |
| 6,410,705 B1 | 6/2002 | Ziegler et al. | 536/23.2 |
| 6,420,151 B1 | 7/2002 | Eikmanns et al. | 435/194 |
| 6,586,214 B1 | 7/2003 | Dunican et al. | 435/115 |
| 6,822,085 B2 | 11/2004 | Farwick et al. | |
| 6,825,029 B2 | 11/2004 | Dunican et al. | 435/252.32 |
| 7,078,204 B2 | 7/2006 | Yokoi | |
| 7,226,762 B2 | 6/2007 | Zelder | |
| 2002/0065403 A1 | 5/2002 | Eikmanns et al. | 536/23.1 |
| 2002/0082403 A1 | 6/2002 | Mockel et al. | 536/23.1 |
| 2002/0106748 A1 | 8/2002 | Mockel et al. | 435/106 |
| 2002/0107378 A1 | 8/2002 | Ziegler et al. | 536/23.2 |
| 2002/0127663 A1 | 9/2002 | Mockel et al. | 435/115 |
| 2002/0146781 A1 | 10/2002 | Ziegler et al. | 435/106 |
| 2002/0168731 A1 | 11/2002 | Ziegler et al. | 435/106 |
| 2002/0197605 A1 | 12/2002 | Nakagawa et al. | 435/6 |
| 2003/0003548 A1 | 1/2003 | Eikmanns et al. | 435/106 |
| 2003/0049802 A1 | 3/2003 | Ziegler et al. | 435/106 |
| 2003/0175911 A1 | 9/2003 | Hans et al. | 435/115 |
| 2003/0199045 A1 | 10/2003 | Burke | |
| 2005/0112733 A1 | 5/2005 | Burke | |
| 2005/0196848 A1 | 9/2005 | Dusch et al. | 435/115 |
| 2005/0233424 A1 | 10/2005 | Farwick et al. | |
| 2006/0014259 A9 | 1/2006 | Burke | |

FOREIGN PATENT DOCUMENTS

| | | |
|---|---|---|
| AU | 200068075 A1 | 5/2001 |
| DE | 195 48 222 A1 | 6/1997 |
| DE | 198 31 609 A1 | 4/1999 |
| DE | 199 41 478 A1 | 3/2001 |
| DE | 199 47 791 A1 | 4/2001 |
| DE | 199 50 409 A1 | 4/2001 |
| DE | 199 51 975 A1 | 5/2001 |
| DE | 199 59 327 A1 | 6/2001 |
| DE | 199 59 328 A1 | 6/2001 |
| EP | 0 197 335 A1 | 10/1986 |
| EP | 0 375 889 A2 | 7/1990 |
| EP | 0 435 132 A1 | 7/1991 |
| EP | 0 472 869 A2 | 3/1992 |
| EP | 0 733 712 A1 | 9/1996 |
| EP | 1 096 013 A2 | 10/2000 |
| EP | 1 108 790 A2 | 6/2001 |
| EP | 1 302 537 | 4/2003 |
| JP | 9-224661 | 9/1997 |
| JP | 9-224662 | 9/1997 |
| JP | 2002 191370 | 7/2002 |
| WO | EP 0 358 940 B1 | 9/1995 |
| WO | WO 96/15246 | 5/1996 |
| WO | WO 01/00844 | 1/2001 |
| WO | WO 01/04322 A1 | 1/2001 |
| WO | WO 01/70995 | 9/2001 |
| WO | WO 01/98472 A1 | 12/2001 |
| WO | WO 03/042389 A1 | 5/2003 |

OTHER PUBLICATIONS

Nishio et al. ( Accession No. Q8FT74).*
Nishio et al. Genome Res: 2003, vol. 13, 1572-1579.*
Archer, et al., "A C-Terminal Deletion in *Corynebacterium glutamicum* Dehydrogenase Abolishes Allosteric Inhibition by L-Threonine," *Gene* 107:53-59 (1991).

(Continued)

*Primary Examiner*—Nashaat T Nashed
*Assistant Examiner*—Mohammad Younus Meah
(74) *Attorney, Agent, or Firm*—Law Office of: Michael A. Senzo, LLC

(57) ABSTRACT

The invention relates to mutants and alleles of the zwf gene of coryneform bacteria, which encode variants of the Zwf subunit of glucose 6-phosphate dehydrogenase (EC: 1.1.1.49), and to processes for preparing amino acids, in particular L-lysine and L-tryptophan, by using bacteria which harbor said alleles.

21 Claims, No Drawings

OTHER PUBLICATIONS

Birnboim, et al., "A Rapid Alkaline Extraction Procedure for Screening Recombinant Plasmid DNA," *Nucleic Acids Res.* 7:1513-1523 (1979).

Eggeling, et al., "L-Glutamate and L-Lysine: Traditional Products with Impetuous Developments," *Appl. Microbiol. Biotechnol.* 52:146-153 (1999).

Eikmanns, et al., "Nucleotide Sequence, Expression and Transcriptional Analysis of the *Corynebacterium glutamicum gltA* Gene Encoding Citrate Synthase," *Microbiology* 140:1817-1828 (1994).

Eikmanns, et al., "Identification, Sequence Analysis, and Expression of a *Corynebacterium glutamicum* Gene Cluster Encoding the Three Glycolytic Enzymes Glyceraldehyde-3-Phosphate Dehydrogenase, 3-Phosphoglycerate Kinase, and Triosephosphate Isomerase," *J. Bacteriol.* 174:6076-6086 (1992).

Eikmanns, et al., "A Family of *Corynebacterium glutamicum/Escherichia coli* Shuttle Vectors for Cloning, Controlled Gene Expression, and Promoter Probing," *Gene* 102:93-98 (1991).

Grabau, et al., "Nucleotide Sequence and Deduced Amino Acid Sequence of *Escherichia coli* Pyruvate Oxidase, a Lipid-Activated Flavorprotein," *Nucleic Acids Res.* 14:5449-5460 (1986).

Heery, et al., "Cloning to the *trp* Gene Cluster from a Tryptophan-Hyperproducing Strain of *Corynebacterium glutamicum*: Identification of a Mutation in the *trp* Leader Sequence," *Appl. Environ. Microbiol.* 59:791-799 (1993).

Jensen, et al., "Artificial Promoters for Metabolic Optimization," *Biotechnol. Bioeng.* 58:191-195 (1998).

Kalinowski, et al., "Aspartokinase Genes *lysCa* and *lysC*β Overlap and Are Adjacent to the Aspartate β-Semialdehyde Dehydrogenase Gene *asd* in *Corynebacterium glutamicum*," *Mol. Gen. Genet.* 224:317-324 (1990).

Krämer, Genetic and Physiological Approaches for the Production of Amino Acids, *J. Bacteriol.* 45:1-21 (1996).

Kupor, et al., "6-Phosphogluconolactonase Mutants of *Escherichia coli* and a Maltose Blue Gene," *J. Bacteriol.* 100:1296-1301 (1969).

Labarre, et al., "Gene Replacement, Integration, and Amplification at the *gdhA* Locus of *Corynebacterium glutamicum*," *J. Bacteriol.* 175:1001-1007 (1993).

Liebl, et al., "High Efficiency Electroporation of Intact *Corynebacterium glutamicum* Cells," *FEMS Microbiol. Letts.* 65:299-304 (1989).

Malumbres, et al., "Codon Preference in Corynebacteria," *Gene* 134:25-24 (1993).

Molenaar, et al., "Biochemical and Genetic Characterization of the Membrane-Associated Malate Dehydrogenase (Acceptor) from *Corynebacterium glutamicum*," *Eur. J. Biochem.* 254:395-403 (1998).

Moritz, et al., "Kinetic Properties of the Glucose-6-Phosphate and 6-Phosphogluconate Dehydrogenases from *Corynebacterium glutamincum* and Their Application for Predicting Pentose Phosphate Pathway Flux in vivo," *Eur. J. Biochem.* 267:3442-3452 (2000).

Peoples, et al., "Nucleotide Sequence and Fine Structural Analysis of the *Corynebacterium glutamicum hom-thrB* Operon," *Mol. Microbiol.* 2:63-72 (1988).

Reinshceid, et al., "Stable Expression of *hom-1-thrB* in *Corynebacterium glutamicum* and Its Effect on the Carbon Flux to Threonine and Related Amino Acids," *Appl. Environ. Microbiol.* 60:126-132 (1994).

Schwarzer, et al., "Manipulation of *Corynebacterium glutamicum* by Gene Disruption and Replacement," *Biotechnology* 9:84-87-(1991).

Spratt, et al., "Kanamycin-Resistant Vectors that are Analogues of Plasmids pUC8, pUC9, pEMBL8, and pEMBL9," *Gene* 41:337-342 (1986).

Sugimoto, et al., "Regulation of Glucose-6-Phosphate Dehydrogenase in *Brevibacterium flavum*," *Agric. Biol. Chem.* 51:101-108 (1987).

Tauch, et al., "*Corynebacterium glutamicum* DNA Is Subjected to Methylation-Restriction in *Escherichia coli*," *FEMS Microbiol. Letts.* 123:343-348 (1994).

Yanisch-Perron, et al., "Improved M13 Phage Cloning Vectors and Host Strains: Nucleotide Sequences of the M13mp18 and pUC19 Vectors," *Gene* 33:103-119 (1985).

Abstract for WO 96/15246, reference B1 above.
Abstract for WO 01/98472, reference B3 above.
Abstract for WO 03/042389, reference B4 above.
Abstract for EP 0 375 889, reference B7 above.
Abstract for EP 0 435 132, reference B8 above.
Abstract for EP 0 472 869, reference B9 above.
Abstract for DE 195 48 222, reference B14 above.
Abstract for DE 198 31 609, reference B15 above.
Abstract for DE 199 41 478, reference B16 above.
Abstract for DE 199 47 791, reference B17 above.
Abstract for DE 199 50 409, reference B18 above.
Abstract for DE 199 51 975, reference B19 above.
Abstract for DE 199 59 327, reference B20 above.
Abstract for DE 199 59 328, reference B21 above.
Abstract for JP 9-224661, reference B22 above.
Abstract for JP 9-224662, reference B23 above.
Abstract for JP 2002 191370, reference B24 above.

Bork, "Powers and Pitfalls in Sequence Analysis: The 70% Hurdle," *Genome Research* 10:398-400 (2000).

Brenner, "Errors in Genome Annotation," *TIG* 15:132-133 (1999).

Kobayashi, et al., "Purification and Properties of NAD-Dependent D-Glucose Dehydrogenase Produced by Alkalophilic *Corynebacterium* sp. No. 93-1," *Agricultural and Biological Chemistry* 44(10):2261-2269 (1980).

Newman, et al., "A Comparison of Gene Organization in the *zwf* Region of the Genomes of the Cyanobacteria *Synechococcus* sp. PCC 7942 and *Anabaena* sp. PCC 7120," *FEMS Microbiology Letters* 133(1-2):187-193 (1995).

Schaeffer, et al., "Glucose-6-phosphate Dehydrogenase of *Anabaena* sp.," *Arch. Microbiol.* 116(1):9-19 (1978).

Summers, et al., "Transcriptional Regulation of *zwf*, Encoding Glucose-6-phosphate Dehydrogenase, from the Cyanobacterium *Nostoc Punctiforme* Strain ATCC 29133," *Mol. Microbiol.* 22(3)473-480 (1996).

Sundaram, et al., "Multiple Oligomeric Forms of Glucose-6-phosphate Dehydrogenase in Cyanobacteria and the Role of OpcA in the Assembly Process," *Microbiology* 144(Pt. 6):1549-1556 (1998).

EMBL:E13655, Hatakeyama, et al, "gDNA encoding Glucose-6-phosphate Dehydrogenase," XP002152311 (1998).

Sequence Alignment, GeneSeq. Accession No. AAT88030, Dec. 1997.

Ohnishi, et al., "A Novel *gnd* Mutation Leading to Increased L-lysine Production in *Corynebacterium glutamicum*," *FEMS Microbiol. Lett.* 242:265-274 (2005).

International Search Report for PCT/EP2006/060519 filed Mar. 7, 2006.

Written Opinion of the International Searching Authority for PCT/EP2006/060519 filed Mar. 7, 2006.

International Preliminary Report on Patentability for PCT/EP2006/060519 filed Mar. 7, 2006.

* cited by examiner

SEQUENCE LISTING

<160> NUMBER OF SEQ ID NOS: 24

<210> SEQ ID NO 1
<211> LENGTH: 1545
<212> TYPE: DNA
<213> ORGANISM: Corynebacterium glutamicum
<220> FEATURE:
<221> NAME/KEY: CDS
<222> LOCATION: (1)..(1542)
<223> OTHER INFORMATION: zwf wild-type gene

<400> SEQUENCE: 1

```
gtg agc aca aac acg acc ccc tcc agc tgg aca aac cca ctg cgc gac      48
Met Ser Thr Asn Thr Thr Pro Ser Ser Trp Thr Asn Pro Leu Arg Asp
1               5                   10                  15
```

-continued

| | |
|---|---|
| ccg cag gat aaa cga ctc ccc cgc atc gct ggc cct tcc ggc atg gtg<br>Pro Gln Asp Lys Arg Leu Pro Arg Ile Ala Gly Pro Ser Gly Met Val<br>20                        25                   30 | 96 |
| atc ttc ggt gtc act ggc gac ttg gct cga aag aag ctg ctc ccc gcc<br>Ile Phe Gly Val Thr Gly Asp Leu Ala Arg Lys Lys Leu Leu Pro Ala<br>35                        40                   45 | 144 |
| att tat gat cta gca aac cgc gga ttg ctg ccc cca gga ttc tcg ttg<br>Ile Tyr Asp Leu Ala Asn Arg Gly Leu Leu Pro Pro Gly Phe Ser Leu<br>50                        55                   60 | 192 |
| gta ggt tac ggc cgc cgc gaa tgg tcc aaa gaa gac ttt gaa aaa tac<br>Val Gly Tyr Gly Arg Arg Glu Trp Ser Lys Glu Asp Phe Glu Lys Tyr<br>65                        70                   75                   80 | 240 |
| gta cgc gat gcc gca agt gct ggt gct cgt acg gaa ttc cgt gaa aat<br>Val Arg Asp Ala Ala Ser Ala Gly Ala Arg Thr Glu Phe Arg Glu Asn<br>85                        90                   95 | 288 |
| gtt tgg gag cgc ctc gcc gag ggt atg gaa ttt gtt cgc ggc aac ttt<br>Val Trp Glu Arg Leu Ala Glu Gly Met Glu Phe Val Arg Gly Asn Phe<br>100                     105                 110 | 336 |
| gat gat gat gca gct ttc gac aac ctc gct gca aca ctc aag cgc atc<br>Asp Asp Asp Ala Ala Phe Asp Asn Leu Ala Ala Thr Leu Lys Arg Ile<br>115                     120                 125 | 384 |
| gac aaa acc cgc ggc acc gcc ggc aac tgg gct tac tac ctg tcc att<br>Asp Lys Thr Arg Gly Thr Ala Gly Asn Trp Ala Tyr Tyr Leu Ser Ile<br>130                     135                 140 | 432 |
| cca cca gat tcc ttc aca gcg gtc tgc cac cag ctg gag cgt tcc ggc<br>Pro Pro Asp Ser Phe Thr Ala Val Cys His Gln Leu Glu Arg Ser Gly<br>145                     150                 155                 160 | 480 |
| atg gct gaa tcc acc gaa gaa gca tgg cgc cgc gtg atc atc gag aag<br>Met Ala Glu Ser Thr Glu Glu Ala Trp Arg Arg Val Ile Ile Glu Lys<br>165                     170                 175 | 528 |
| cct ttc ggc cac aac ctc gaa tcc gca cac gag ctc aac cag ctg gtc<br>Pro Phe Gly His Asn Leu Glu Ser Ala His Glu Leu Asn Gln Leu Val<br>180                     185                 190 | 576 |
| aac gca gtc ttc cca gaa tct tct gtg ttc cgc atc gac cac tat ttg<br>Asn Ala Val Phe Pro Glu Ser Ser Val Phe Arg Ile Asp His Tyr Leu<br>195                     200                 205 | 624 |
| ggc aag gaa aca gtt caa aac atc ctg gct ctg cgt ttt gct aac cag<br>Gly Lys Glu Thr Val Gln Asn Ile Leu Ala Leu Arg Phe Ala Asn Gln<br>210                     215                 220 | 672 |
| ctg ttt gag cca ctg tgg aac tcc aac tac gtt gac cac gtc cag atc<br>Leu Phe Glu Pro Leu Trp Asn Ser Asn Tyr Val Asp His Val Gln Ile<br>225                     230                 235                 240 | 720 |
| acc atg gct gaa gat att ggc ttg ggt gga cgt gct ggt tac tac gac<br>Thr Met Ala Glu Asp Ile Gly Leu Gly Gly Arg Ala Gly Tyr Tyr Asp<br>245                     250                 255 | 768 |
| ggc atc ggc gca gcc cgc gac gtc atc cag aac cac ctg atc cag ctc<br>Gly Ile Gly Ala Ala Arg Asp Val Ile Gln Asn His Leu Ile Gln Leu<br>260                     265                 270 | 816 |
| ttg gct ctg gtt gcc atg gaa gaa cca att tct ttc gtg cca gcg cag<br>Leu Ala Leu Val Ala Met Glu Glu Pro Ile Ser Phe Val Pro Ala Gln<br>275                     280                 285 | 864 |
| ctg cag gca gaa aag atc aag gtg ctc tct gcg aca aag ccg tgc tac<br>Leu Gln Ala Glu Lys Ile Lys Val Leu Ser Ala Thr Lys Pro Cys Tyr<br>290                     295                 300 | 912 |
| cca ttg gat aaa acc tcc gct cgt ggt cag tac gct gcc ggt tgg cag<br>Pro Leu Asp Lys Thr Ser Ala Arg Gly Gln Tyr Ala Ala Gly Trp Gln<br>305                     310                 315                 320 | 960 |
| ggc tct gag tta gtc aag gga ctt cgc gaa gaa gat ggc ttc aac cct<br>Gly Ser Glu Leu Val Lys Gly Leu Arg Glu Glu Asp Gly Phe Asn Pro | 1008 |

```
                325                 330                 335
gag tcc acc act gag act ttt gcg gct tgt acc tta gag atc acg tct     1056
Glu Ser Thr Thr Glu Thr Phe Ala Ala Cys Thr Leu Glu Ile Thr Ser
            340                 345                 350 cgt cgc tgg gct ggt gtg ccg ttc tac ctg cgc acc ggt aag cgt ctt     1104
Arg Arg Trp Ala Gly Val Pro Phe Tyr Leu Arg Thr Gly Lys Arg Leu
        355                 360                 365 ggt cgc cgt gtt act gag att gcc gtg gtg ttt aaa gac gca cca cac     1152
Gly Arg Arg Val Thr Glu Ile Ala Val Val Phe Lys Asp Ala Pro His
    370                 375                 380 cag cct ttc gac ggc gac atg act gta tcc ctt ggc caa aac gcc atc     1200
Gln Pro Phe Asp Gly Asp Met Thr Val Ser Leu Gly Gln Asn Ala Ile
385                 390                 395                 400 gtg att cgc gtg cag cct gat gaa ggt gtg ctc atc cgc ttc ggt tcc     1248
Val Ile Arg Val Gln Pro Asp Glu Gly Val Leu Ile Arg Phe Gly Ser
                405                 410                 415 aag gtt cca ggt tct gcc atg gaa gtc cgt gac gtc aac atg gac ttc     1296
Lys Val Pro Gly Ser Ala Met Glu Val Arg Asp Val Asn Met Asp Phe
            420                 425                 430 tcc tac tca gaa tcc ttc act gaa gaa tca cct gaa gca tac gag cgc     1344
Ser Tyr Ser Glu Ser Phe Thr Glu Glu Ser Pro Glu Ala Tyr Glu Arg
        435                 440                 445 ctc att ttg gat gcg ctg tta gat gaa tcc agc ctc ttc cct acc aac     1392
Leu Ile Leu Asp Ala Leu Leu Asp Glu Ser Ser Leu Phe Pro Thr Asn
    450                 455                 460 gag gaa gtg gaa ctg agc tgg aag att ctg gat cca att ctt gaa gca     1440
Glu Glu Val Glu Leu Ser Trp Lys Ile Leu Asp Pro Ile Leu Glu Ala
465                 470                 475                 480 tgg gat gcc gat gga gaa cca gag gat tac cca gcg ggt acg tgg ggt     1488
Trp Asp Ala Asp Gly Glu Pro Glu Asp Tyr Pro Ala Gly Thr Trp Gly
                485                 490                 495 cca aag agc gct gat gaa atg ctt tcc cgc aac ggt cac acc tgg cgc     1536
Pro Lys Ser Ala Asp Glu Met Leu Ser Arg Asn Gly His Thr Trp Arg
            500                 505                 510 agg cca taa                                                          1545
Arg Pro <210> SEQ ID NO 2
<211> LENGTH: 514
<212> TYPE: PRT
<213> ORGANISM: Corynebacterium glutamicum

<400> SEQUENCE: 2

Met Ser Thr Asn Thr Thr Pro Ser Ser Trp Thr Asn Pro Leu Arg Asp
1               5                   10                  15

Pro Gln Asp Lys Arg Leu Pro Arg Ile Ala Gly Pro Ser Gly Met Val
            20                  25                  30

Ile Phe Gly Val Thr Gly Asp Leu Ala Arg Lys Lys Leu Leu Pro Ala
        35                  40                  45

Ile Tyr Asp Leu Ala Asn Arg Gly Leu Leu Pro Pro Gly Phe Ser Leu
    50                  55                  60

Val Gly Tyr Gly Arg Arg Glu Trp Ser Lys Glu Asp Phe Glu Lys Tyr
65                  70                  75                  80

Val Arg Asp Ala Ala Ser Ala Gly Ala Arg Thr Glu Phe Arg Glu Asn
                85                  90                  95

Val Trp Glu Arg Leu Ala Glu Gly Met Glu Phe Val Arg Gly Asn Phe
            100                 105                 110

Asp Asp Asp Ala Ala Phe Asp Asn Leu Ala Ala Thr Leu Lys Arg Ile
```

```
                115                 120                 125
Asp Lys Thr Arg Gly Thr Ala Gly Asn Trp Ala Tyr Tyr Leu Ser Ile
    130                 135                 140
Pro Pro Asp Ser Phe Thr Ala Val Cys His Gln Leu Glu Arg Ser Gly
145                 150                 155                 160
Met Ala Glu Ser Thr Glu Ala Trp Arg Arg Val Ile Ile Glu Lys
                165                 170                 175
Pro Phe Gly His Asn Leu Glu Ser Ala His Glu Leu Asn Gln Leu Val
                180                 185                 190
Asn Ala Val Phe Pro Glu Ser Ser Val Phe Arg Ile Asp His Tyr Leu
            195                 200                 205
Gly Lys Glu Thr Val Gln Asn Ile Leu Ala Leu Arg Phe Ala Asn Gln
        210                 215                 220
Leu Phe Glu Pro Leu Trp Asn Ser Asn Tyr Val Asp His Val Gln Ile
225                 230                 235                 240
Thr Met Ala Glu Asp Ile Gly Leu Gly Gly Arg Ala Gly Tyr Tyr Asp
                245                 250                 255
Gly Ile Gly Ala Ala Arg Asp Val Ile Gln Asn His Leu Ile Gln Leu
            260                 265                 270
Leu Ala Leu Val Ala Met Glu Glu Pro Ile Ser Phe Val Pro Ala Gln
        275                 280                 285
Leu Gln Ala Glu Lys Ile Lys Val Leu Ser Ala Thr Lys Pro Cys Tyr
    290                 295                 300
Pro Leu Asp Lys Thr Ser Ala Arg Gly Gln Tyr Ala Ala Gly Trp Gln
305                 310                 315                 320
Gly Ser Glu Leu Val Lys Gly Leu Arg Glu Glu Asp Gly Phe Asn Pro
                325                 330                 335
Glu Ser Thr Thr Glu Thr Phe Ala Ala Cys Thr Leu Glu Ile Thr Ser
                340                 345                 350
Arg Arg Trp Ala Gly Val Pro Phe Tyr Leu Arg Thr Gly Lys Arg Leu
            355                 360                 365
Gly Arg Arg Val Thr Glu Ile Ala Val Val Phe Lys Asp Ala Pro His
        370                 375                 380
Gln Pro Phe Asp Gly Asp Met Thr Val Ser Leu Gly Gln Asn Ala Ile
385                 390                 395                 400
Val Ile Arg Val Gln Pro Asp Glu Gly Val Leu Ile Arg Phe Gly Ser
                405                 410                 415
Lys Val Pro Gly Ser Ala Met Glu Val Arg Asp Val Asn Met Asp Phe
                420                 425                 430
Ser Tyr Ser Glu Ser Phe Thr Glu Glu Ser Pro Glu Ala Tyr Glu Arg
            435                 440                 445
Leu Ile Leu Asp Ala Leu Leu Asp Glu Ser Ser Leu Phe Pro Thr Asn
        450                 455                 460
Glu Glu Val Glu Leu Ser Trp Lys Ile Leu Asp Pro Ile Leu Glu Ala
465                 470                 475                 480
Trp Asp Ala Asp Gly Glu Pro Glu Asp Tyr Pro Ala Gly Thr Trp Gly
                485                 490                 495
Pro Lys Ser Ala Asp Glu Met Leu Ser Arg Asn Gly His Thr Trp Arg
            500                 505                 510
Arg Pro

<210> SEQ ID NO 3
<211> LENGTH: 2100
```

```
<212> TYPE: DNA
<213> ORGANISM: Corynebacterium glutamicum
<220> FEATURE:
<221> NAME/KEY: CDS
<222> LOCATION: (308)..(1849)
<223> OTHER INFORMATION: zwf wild-type gene

<400> SEQUENCE: 3
tcgacgcggt tctggagcag ggcaacctgc acggtgacac cctgtccaac tccgcggcag      60
aagctgacgc tgtgttctcc cagcttgagg ctctgggcgt tgacttggca gatgtcttcc     120
aggtcctgga gaccgagggt gtggacaagt tcgttgcttc ttggagcgaa ctgcttgagt     180
ccatggaagc tcgcctgaag tagaatcagc acgctgcatc agtaacggcg acatgaaatc     240
gaattagttc gatcttatgt ggccgttaca catctttcat taaagaaagg atcgtgacac     300 taccatc gtg agc aca aac acg acc ccc tcc agc tgg aca aac cca ctg       349
        Met Ser Thr Asn Thr Thr Pro Ser Ser Trp Thr Asn Pro Leu
        1               5                   10 cgc gac ccg cag gat aaa cga ctc ccc cgc atc gct ggc cct tcc ggc       397
Arg Asp Pro Gln Asp Lys Arg Leu Pro Arg Ile Ala Gly Pro Ser Gly
15                  20                  25                  30 atg gtg atc ttc ggt gtc act ggc gac ttg gct cga aag aag ctg ctc       445
Met Val Ile Phe Gly Val Thr Gly Asp Leu Ala Arg Lys Lys Leu Leu
                35                  40                  45 ccc gcc att tat gat cta gca aac cgc gga ttg ctg ccc cca gga ttc       493
Pro Ala Ile Tyr Asp Leu Ala Asn Arg Gly Leu Leu Pro Pro Gly Phe
            50                  55                  60 tcg ttg gta ggt tac ggc cgc cgc gaa tgg tcc aaa gaa gac ttt gaa       541
Ser Leu Val Gly Tyr Gly Arg Arg Glu Trp Ser Lys Glu Asp Phe Glu
        65                  70                  75 aaa tac gta cgc gat gcc gca agt gct ggt gct cgt acg gaa ttc cgt       589
Lys Tyr Val Arg Asp Ala Ala Ser Ala Gly Ala Arg Thr Glu Phe Arg
    80                  85                  90 gaa aat gtt tgg gag cgc ctc gcc gag ggt atg gaa ttt gtt cgc ggc       637
Glu Asn Val Trp Glu Arg Leu Ala Glu Gly Met Glu Phe Val Arg Gly
95                  100                 105                 110 aac ttt gat gat gat gca gct ttc gac aac ctc gct gca aca ctc aag       685
Asn Phe Asp Asp Asp Ala Ala Phe Asp Asn Leu Ala Ala Thr Leu Lys
                115                 120                 125 cgc atc gac aaa acc cgc ggc acc gcc ggc aac tgg gct tac tac ctg       733
Arg Ile Asp Lys Thr Arg Gly Thr Ala Gly Asn Trp Ala Tyr Tyr Leu
            130                 135                 140 tcc att cca cca gat tcc ttc aca gcg gtc tgc cac cag ctg gag cgt       781
Ser Ile Pro Pro Asp Ser Phe Thr Ala Val Cys His Gln Leu Glu Arg
        145                 150                 155 tcc ggc atg gct gaa tcc acc gaa gaa gca tgg cgc cgc gtg atc atc       829
Ser Gly Met Ala Glu Ser Thr Glu Glu Ala Trp Arg Arg Val Ile Ile
    160                 165                 170 gag aag cct ttc ggc cac aac ctc gaa tcc gca cac gag ctc aac cag       877
Glu Lys Pro Phe Gly His Asn Leu Glu Ser Ala His Glu Leu Asn Gln
175                 180                 185                 190 ctg gtc aac gca gtc ttc cca gaa tct tct gtg ttc cgc atc gac cac       925
Leu Val Asn Ala Val Phe Pro Glu Ser Ser Val Phe Arg Ile Asp His
                195                 200                 205 tat ttg ggc aag gaa aca gtt caa aac atc ctg gct ctg cgt ttt gct       973
Tyr Leu Gly Lys Glu Thr Val Gln Asn Ile Leu Ala Leu Arg Phe Ala
            210                 215                 220 aac cag ctg ttt gag cca ctg tgg aac tcc aac tac gtt gac cac gtc      1021
Asn Gln Leu Phe Glu Pro Leu Trp Asn Ser Asn Tyr Val Asp His Val
        225                 230                 235
```

-continued

```
cag atc acc atg gct gaa gat att ggc ttg ggt gga cgt gct ggt tac       1069
Gln Ile Thr Met Ala Glu Asp Ile Gly Leu Gly Gly Arg Ala Gly Tyr
    240                 245                 250 tac gac ggc atc ggc gca gcc cgc gac gtc atc cag aac cac ctg atc       1117
Tyr Asp Gly Ile Gly Ala Ala Arg Asp Val Ile Gln Asn His Leu Ile
255                 260                 265                 270 cag ctc ttg gct ctg gtt gcc atg gaa gaa cca att tct ttc gtg cca       1165
Gln Leu Leu Ala Leu Val Ala Met Glu Glu Pro Ile Ser Phe Val Pro
                275                 280                 285 gcg cag ctg cag gca gaa aag atc aag gtg ctc tct gcg aca aag ccg       1213
Ala Gln Leu Gln Ala Glu Lys Ile Lys Val Leu Ser Ala Thr Lys Pro
        290                 295                 300 tgc tac cca ttg gat aaa acc tcc gct cgt ggt cag tac gct gcc ggt       1261
Cys Tyr Pro Leu Asp Lys Thr Ser Ala Arg Gly Gln Tyr Ala Ala Gly
            305                 310                 315 tgg cag ggc tct gag tta gtc aag gga ctt cgc gaa gaa gat ggc ttc       1309
Trp Gln Gly Ser Glu Leu Val Lys Gly Leu Arg Glu Glu Asp Gly Phe
320                 325                 330 aac cct gag tcc acc act gag act ttt gcg gct tgt acc tta gag atc       1357
Asn Pro Glu Ser Thr Thr Glu Thr Phe Ala Ala Cys Thr Leu Glu Ile
335                 340                 345                 350 acg tct cgt cgc tgg gct ggt gtg ccg ttc tac ctg cgc acc ggt aag       1405
Thr Ser Arg Arg Trp Ala Gly Val Pro Phe Tyr Leu Arg Thr Gly Lys
                355                 360                 365 cgt ctt ggt cgc gtt act gag att gcc gtg gtg ttt aaa gac gca           1453
Arg Leu Gly Arg Arg Val Thr Glu Ile Ala Val Val Phe Lys Asp Ala
        370                 375                 380 cca cac cag cct ttc gac ggc gac atg act gta tcc ctt ggc caa aac       1501
Pro His Gln Pro Phe Asp Gly Asp Met Thr Val Ser Leu Gly Gln Asn
            385                 390                 395 gcc atc gtg att cgc gtg cag cct gat gaa ggt gtg ctc atc cgc ttc       1549
Ala Ile Val Ile Arg Val Gln Pro Asp Glu Gly Val Leu Ile Arg Phe
400                 405                 410 ggt tcc aag gtt cca ggt tct gcc atg gaa gtc cgt gac gtc aac atg       1597
Gly Ser Lys Val Pro Gly Ser Ala Met Glu Val Arg Asp Val Asn Met
415                 420                 425                 430 gac ttc tcc tac tca gaa tcc ttc act gaa gaa tca cct gaa gca tac       1645
Asp Phe Ser Tyr Ser Glu Ser Phe Thr Glu Glu Ser Pro Glu Ala Tyr
                435                 440                 445 gag cgc ctc att ttg gat gcg ctg tta gat gaa tcc agc ctc ttc cct       1693
Glu Arg Leu Ile Leu Asp Ala Leu Leu Asp Glu Ser Ser Leu Phe Pro
        450                 455                 460 acc aac gag gaa gtg gaa ctg agc tgg aag att ctg gat cca att ctt       1741
Thr Asn Glu Glu Val Glu Leu Ser Trp Lys Ile Leu Asp Pro Ile Leu
            465                 470                 475 gaa gca tgg gat gcc gat gga gaa cca gag gat tac cca gcg ggt acg       1789
Glu Ala Trp Asp Ala Asp Gly Glu Pro Glu Asp Tyr Pro Ala Gly Thr
480                 485                 490 tgg ggt cca aag agc gct gat gaa atg ctt tcc cgc aac ggt cac acc       1837
Trp Gly Pro Lys Ser Ala Asp Glu Met Leu Ser Arg Asn Gly His Thr
495                 500                 505                 510 tgg cgc agg cca taatttaggg gcaaaaaatg atctttgaac ttccggatac          1889
Trp Arg Arg Pro caccacccag caaatttcca agaccctaac tcgactgcgt gaatcgggca cccaggtcac    1949
caccggccga gtgctcaccc tcatcgtggt cactgactcc gaaagcgatg tcgctgcagt    2009
taccgagtcc accatgaagg cctcgcgcga gcacccatct cgcgtgatca ttttggtggt    2069
tggcgataaa actgcagaaa acaaagttga c                                    2100
```

<210> SEQ ID NO 4
<211> LENGTH: 514
<212> TYPE: PRT
<213> ORGANISM: Corynebacterium glutamicum

<400> SEQUENCE: 4

Met Ser Thr Asn Thr Pro Ser Ser Trp Thr Asn Pro Leu Arg Asp
1               5                   10                  15

Pro Gln Asp Lys Arg Leu Pro Arg Ile Ala Gly Pro Ser Gly Met Val
            20                  25                  30

Ile Phe Gly Val Thr Gly Asp Leu Ala Arg Lys Lys Leu Leu Pro Ala
        35                  40                  45

Ile Tyr Asp Leu Ala Asn Arg Gly Leu Leu Pro Pro Gly Phe Ser Leu
    50                  55                  60

Val Gly Tyr Gly Arg Arg Glu Trp Ser Lys Glu Asp Phe Glu Lys Tyr
65                  70                  75                  80

Val Arg Asp Ala Ala Ser Ala Gly Ala Arg Thr Glu Phe Arg Glu Asn
                85                  90                  95

Val Trp Glu Arg Leu Ala Glu Gly Met Glu Phe Val Arg Gly Asn Phe
            100                 105                 110

Asp Asp Asp Ala Ala Phe Asp Asn Leu Ala Ala Thr Leu Lys Arg Ile
        115                 120                 125

Asp Lys Thr Arg Gly Thr Ala Gly Asn Trp Ala Tyr Tyr Leu Ser Ile
    130                 135                 140

Pro Pro Asp Ser Phe Thr Ala Val Cys His Gln Leu Glu Arg Ser Gly
145                 150                 155                 160

Met Ala Glu Ser Thr Glu Glu Ala Trp Arg Arg Val Ile Ile Glu Lys
                165                 170                 175

Pro Phe Gly His Asn Leu Glu Ser Ala His Glu Leu Asn Gln Leu Val
            180                 185                 190

Asn Ala Val Phe Pro Glu Ser Ser Val Phe Arg Ile Asp His Tyr Leu
        195                 200                 205

Gly Lys Glu Thr Val Gln Asn Ile Leu Ala Leu Arg Phe Ala Asn Gln
    210                 215                 220

Leu Phe Glu Pro Leu Trp Asn Ser Asn Tyr Val Asp His Val Gln Ile
225                 230                 235                 240

Thr Met Ala Glu Asp Ile Gly Leu Gly Gly Arg Ala Gly Tyr Tyr Asp
                245                 250                 255

Gly Ile Gly Ala Ala Arg Asp Val Ile Gln Asn His Leu Ile Gln Leu
            260                 265                 270

Leu Ala Leu Val Ala Met Glu Glu Pro Ile Ser Phe Val Pro Ala Gln
        275                 280                 285

Leu Gln Ala Glu Lys Ile Lys Val Leu Ser Ala Thr Lys Pro Cys Tyr
    290                 295                 300

Pro Leu Asp Lys Thr Ser Ala Arg Gly Gln Tyr Ala Ala Gly Trp Gln
305                 310                 315                 320

Gly Ser Glu Leu Val Lys Gly Leu Arg Glu Glu Asp Gly Phe Asn Pro
                325                 330                 335

Glu Ser Thr Thr Glu Thr Phe Ala Ala Cys Thr Leu Glu Ile Thr Ser
            340                 345                 350

Arg Arg Trp Ala Gly Val Pro Phe Tyr Leu Arg Thr Gly Lys Arg Leu
        355                 360                 365

Gly Arg Arg Val Thr Glu Ile Ala Val Val Phe Lys Asp Ala Pro His
    370                 375                 380

```
Gln Pro Phe Asp Gly Asp Met Thr Val Ser Leu Gly Gln Asn Ala Ile
385                 390                 395                 400

Val Ile Arg Val Gln Pro Asp Glu Gly Val Leu Ile Arg Phe Gly Ser
            405                 410                 415

Lys Val Pro Gly Ser Ala Met Glu Val Arg Asp Val Asn Met Asp Phe
            420                 425                 430

Ser Tyr Ser Glu Ser Phe Thr Glu Glu Ser Pro Glu Ala Tyr Glu Arg
            435                 440                 445

Leu Ile Leu Asp Ala Leu Leu Asp Glu Ser Ser Leu Phe Pro Thr Asn
            450                 455                 460

Glu Glu Val Glu Leu Ser Trp Lys Ile Leu Asp Pro Ile Leu Glu Ala
465                 470                 475                 480

Trp Asp Ala Asp Gly Glu Pro Glu Asp Tyr Pro Ala Gly Thr Trp Gly
            485                 490                 495

Pro Lys Ser Ala Asp Glu Met Leu Ser Arg Asn Gly His Thr Trp Arg
            500                 505                 510

Arg Pro

<210> SEQ ID NO 5
<211> LENGTH: 1545
<212> TYPE: DNA
<213> ORGANISM: Corynebacterium glutamicum
<220> FEATURE:
<221> NAME/KEY: CDS
<222> LOCATION: (1)..(1542)
<223> OTHER INFORMATION: zwf allele
<220> FEATURE:
<221> NAME/KEY: mutation
<222> LOCATION: (961)..(961)
<223> OTHER INFORMATION: G -> A transition

<400> SEQUENCE: 5 gtg agc aca aac acg acc ccc tcc agc tgg aca aac cca ctg cgc gac    48
Met Ser Thr Asn Thr Thr Pro Ser Ser Trp Thr Asn Pro Leu Arg Asp
1               5                   10                  15 ccg cag gat aaa cga ctc ccc cgc atc gct ggc cct tcc ggc atg gtg    96
Pro Gln Asp Lys Arg Leu Pro Arg Ile Ala Gly Pro Ser Gly Met Val
            20                  25                  30 atc ttc ggt gtc act ggc gac ttg gct cga aag aag ctg ctc ccc gcc   144
Ile Phe Gly Val Thr Gly Asp Leu Ala Arg Lys Lys Leu Leu Pro Ala
        35                  40                  45 att tat gat cta gca aac cgc gga ttg ctg ccc cca gga ttc tcg ttg   192
Ile Tyr Asp Leu Ala Asn Arg Gly Leu Leu Pro Pro Gly Phe Ser Leu
    50                  55                  60 gta ggt tac ggc cgc cgc gaa tgg tcc aaa gaa gac ttt gaa aaa tac   240
Val Gly Tyr Gly Arg Arg Glu Trp Ser Lys Glu Asp Phe Glu Lys Tyr
65                  70                  75                  80 gta cgc gat gcc gca agt gct ggt gct cgt acg gaa ttc cgt gaa aat   288
Val Arg Asp Ala Ala Ser Ala Gly Ala Arg Thr Glu Phe Arg Glu Asn
                85                  90                  95 gtt tgg gag cgc ctc gcc gag ggt atg gaa ttt gtt cgc ggc aac ttt   336
Val Trp Glu Arg Leu Ala Glu Gly Met Glu Phe Val Arg Gly Asn Phe
            100                 105                 110 gat gat gat gca gct ttc gac aac ctc gct gca aca ctc aag cgc atc   384
Asp Asp Asp Ala Ala Phe Asp Asn Leu Ala Ala Thr Leu Lys Arg Ile
        115                 120                 125 gac aaa acc cgc ggc acc gcc ggc aac tgg gct tac tac ctg tcc att   432
Asp Lys Thr Arg Gly Thr Ala Gly Asn Trp Ala Tyr Tyr Leu Ser Ile
    130                 135                 140
```

-continued

```
cca cca gat tcc ttc aca gcg gtc tgc cac cag ctg gag cgt tcc ggc    480
Pro Pro Asp Ser Phe Thr Ala Val Cys His Gln Leu Glu Arg Ser Gly
145                 150                 155                 160 atg gct gaa tcc acc gaa gaa gca tgg cgc cgc gtg atc atc gag aag    528
Met Ala Glu Ser Thr Glu Glu Ala Trp Arg Arg Val Ile Ile Glu Lys
                165                 170                 175 cct ttc ggc cac aac ctc gaa tcc gca cac gag ctc aac cag ctg gtc    576
Pro Phe Gly His Asn Leu Glu Ser Ala His Glu Leu Asn Gln Leu Val
            180                 185                 190 aac gca gtc ttc cca gaa tct tct gtg ttc cgc atc gac cac tat ttg    624
Asn Ala Val Phe Pro Glu Ser Ser Val Phe Arg Ile Asp His Tyr Leu
        195                 200                 205 ggc aag gaa aca gtt caa aac atc ctg gct ctg cgt ttt gct aac cag    672
Gly Lys Glu Thr Val Gln Asn Ile Leu Ala Leu Arg Phe Ala Asn Gln
    210                 215                 220 ctg ttt gag cca ctg tgg aac tcc aac tac gtt gac cac gtc cag atc    720
Leu Phe Glu Pro Leu Trp Asn Ser Asn Tyr Val Asp His Val Gln Ile
225                 230                 235                 240 acc atg gct gaa gat att ggc ttg ggt gga cgt gct ggt tac tac gac    768
Thr Met Ala Glu Asp Ile Gly Leu Gly Gly Arg Ala Gly Tyr Tyr Asp
                245                 250                 255 ggc atc ggc gca gcc cgc gac gtc atc cag aac cac ctg atc cag ctc    816
Gly Ile Gly Ala Ala Arg Asp Val Ile Gln Asn His Leu Ile Gln Leu
            260                 265                 270 ttg gct ctg gtt gcc atg gaa gaa cca att tct ttc gtg cca gcg cag    864
Leu Ala Leu Val Ala Met Glu Glu Pro Ile Ser Phe Val Pro Ala Gln
        275                 280                 285 ctg cag gca gaa aag atc aag gtg ctc tct gcg aca aag ccg tgc tac    912
Leu Gln Ala Glu Lys Ile Lys Val Leu Ser Ala Thr Lys Pro Cys Tyr
    290                 295                 300 cca ttg gat aaa acc tcc gct cgt ggt cag tac gct gcc ggt tgg cag    960
Pro Leu Asp Lys Thr Ser Ala Arg Gly Gln Tyr Ala Ala Gly Trp Gln
305                 310                 315                 320 agc tct gag tta gtc aag gga ctt cgc gaa gaa gat ggc ttc aac cct   1008
Ser Ser Glu Leu Val Lys Gly Leu Arg Glu Glu Asp Gly Phe Asn Pro
                325                 330                 335 gag tcc acc act gag act ttt gcg gct tgt acc tta gag atc acg tct   1056
Glu Ser Thr Thr Glu Thr Phe Ala Ala Cys Thr Leu Glu Ile Thr Ser
            340                 345                 350 cgt cgc tgg gct ggt gtg ccg ttc tac ctg cgc acc ggt aag cgt ctt   1104
Arg Arg Trp Ala Gly Val Pro Phe Tyr Leu Arg Thr Gly Lys Arg Leu
        355                 360                 365 ggt cgc cgt gtt act gag att gcc gtg gtg ttt aaa gac gca cca cac   1152
Gly Arg Arg Val Thr Glu Ile Ala Val Val Phe Lys Asp Ala Pro His
    370                 375                 380 cag cct ttc gac ggc gac atg act gta tcc ctt ggc caa aac gcc atc   1200
Gln Pro Phe Asp Gly Asp Met Thr Val Ser Leu Gly Gln Asn Ala Ile
385                 390                 395                 400 gtg att cgc gtg cag cct gat gaa ggt gtg ctc atc cgc ttc ggt tcc   1248
Val Ile Arg Val Gln Pro Asp Glu Gly Val Leu Ile Arg Phe Gly Ser
                405                 410                 415 aag gtt cca ggt tct gcc atg gaa gtc cgt gac gtc aac atg gac ttc   1296
Lys Val Pro Gly Ser Ala Met Glu Val Arg Asp Val Asn Met Asp Phe
            420                 425                 430 tcc tac tca gaa tcc ttc act gaa gaa tca cct gaa gca tac gag cgc   1344
Ser Tyr Ser Glu Ser Phe Thr Glu Glu Ser Pro Glu Ala Tyr Glu Arg
        435                 440                 445 ctc att ttg gat gcg ctg tta gat gaa tcc agc ctc ttc cct acc aac   1392
Leu Ile Leu Asp Ala Leu Leu Asp Glu Ser Ser Leu Phe Pro Thr Asn
    450                 455                 460
```

```
                                                         -continued
gag gaa gtg gaa ctg agc tgg aag att ctg gat cca att ctt gaa gca   1440
Glu Glu Val Glu Leu Ser Trp Lys Ile Leu Asp Pro Ile Leu Glu Ala
465                 470                 475                 480 tgg gat gcc gat gga gaa cca gag gat tac cca gcg ggt acg tgg ggt   1488
Trp Asp Ala Asp Gly Glu Pro Glu Asp Tyr Pro Ala Gly Thr Trp Gly
                485                 490                 495 cca aag agc gct gat gaa atg ctt tcc cgc aac ggt cac acc tgg cgc   1536
Pro Lys Ser Ala Asp Glu Met Leu Ser Arg Asn Gly His Thr Trp Arg
            500                 505                 510 agg cca taa                                                       1545
Arg Pro

<210> SEQ ID NO 6
<211> LENGTH: 514
<212> TYPE: PRT
<213> ORGANISM: Corynebacterium glutamicum

<400> SEQUENCE: 6

Met Ser Thr Asn Thr Thr Pro Ser Ser Trp Thr Asn Pro Leu Arg Asp
1               5                   10                  15

Pro Gln Asp Lys Arg Leu Pro Arg Ile Ala Gly Pro Ser Gly Met Val
            20                  25                  30

Ile Phe Gly Val Thr Gly Asp Leu Ala Arg Lys Lys Leu Leu Pro Ala
        35                  40                  45

Ile Tyr Asp Leu Ala Asn Arg Gly Leu Leu Pro Pro Gly Phe Ser Leu
    50                  55                  60

Val Gly Tyr Gly Arg Arg Glu Trp Ser Lys Glu Asp Phe Glu Lys Tyr
65                  70                  75                  80

Val Arg Asp Ala Ala Ser Ala Gly Ala Arg Thr Glu Phe Arg Glu Asn
                85                  90                  95

Val Trp Glu Arg Leu Ala Glu Gly Met Glu Phe Val Arg Gly Asn Phe
            100                 105                 110

Asp Asp Asp Ala Ala Phe Asp Asn Leu Ala Ala Thr Leu Lys Arg Ile
        115                 120                 125

Asp Lys Thr Arg Gly Thr Ala Gly Asn Trp Ala Tyr Tyr Leu Ser Ile
    130                 135                 140

Pro Pro Asp Ser Phe Thr Ala Val Cys His Gln Leu Glu Arg Ser Gly
145                 150                 155                 160

Met Ala Glu Ser Thr Glu Glu Ala Trp Arg Arg Val Ile Ile Glu Lys
                165                 170                 175

Pro Phe Gly His Asn Leu Glu Ser Ala His Glu Leu Asn Gln Leu Val
            180                 185                 190

Asn Ala Val Phe Pro Glu Ser Ser Val Phe Arg Ile Asp His Tyr Leu
        195                 200                 205

Gly Lys Glu Thr Val Gln Asn Ile Leu Ala Leu Arg Phe Ala Asn Gln
    210                 215                 220

Leu Phe Glu Pro Leu Trp Asn Ser Asn Tyr Val Asp His Val Gln Ile
225                 230                 235                 240

Thr Met Ala Glu Asp Ile Gly Leu Gly Gly Arg Ala Gly Tyr Tyr Asp
                245                 250                 255

Gly Ile Gly Ala Ala Arg Asp Val Ile Gln Asn His Leu Ile Gln Leu
            260                 265                 270

Leu Ala Leu Val Ala Met Glu Glu Pro Ile Ser Phe Val Pro Ala Gln
        275                 280                 285

Leu Gln Ala Glu Lys Ile Lys Val Leu Ser Ala Thr Lys Pro Cys Tyr
```

-continued

```
           290                 295                 300
Pro Leu Asp Lys Thr Ser Ala Arg Gly Gln Tyr Ala Ala Gly Trp Gln
305                 310                 315                 320

Ser Ser Glu Leu Val Lys Gly Leu Arg Glu Glu Asp Gly Phe Asn Pro
                325                 330                 335

Glu Ser Thr Thr Glu Thr Phe Ala Ala Cys Thr Leu Glu Ile Thr Ser
            340                 345                 350

Arg Arg Trp Ala Gly Val Pro Phe Tyr Leu Arg Thr Gly Lys Arg Leu
                355                 360                 365

Gly Arg Arg Val Thr Glu Ile Ala Val Val Phe Lys Asp Ala Pro His
370                 375                 380

Gln Pro Phe Asp Gly Asp Met Thr Val Ser Leu Gly Gln Asn Ala Ile
385                 390                 395                 400

Val Ile Arg Val Gln Pro Asp Glu Gly Val Leu Ile Arg Phe Gly Ser
                405                 410                 415

Lys Val Pro Gly Ser Ala Met Glu Val Arg Asp Val Asn Met Asp Phe
                420                 425                 430

Ser Tyr Ser Glu Ser Phe Thr Glu Glu Ser Pro Glu Ala Tyr Glu Arg
            435                 440                 445

Leu Ile Leu Asp Ala Leu Leu Asp Glu Ser Ser Leu Phe Pro Thr Asn
        450                 455                 460

Glu Glu Val Glu Leu Ser Trp Lys Ile Leu Asp Pro Ile Leu Glu Ala
465                 470                 475                 480

Trp Asp Ala Asp Gly Glu Pro Glu Asp Tyr Pro Ala Gly Thr Trp Gly
                485                 490                 495

Pro Lys Ser Ala Asp Glu Met Leu Ser Arg Asn Gly His Thr Trp Arg
                500                 505                 510

Arg Pro
```

```
<210> SEQ ID NO 7
<211> LENGTH: 1545
<212> TYPE: DNA
<213> ORGANISM: Corynebacterium glutamicum
<220> FEATURE:
<221> NAME/KEY: CDS
<222> LOCATION: (1)..(1542)
<223> OTHER INFORMATION: zwf allele
<220> FEATURE:
<221> NAME/KEY: mutation
<222> LOCATION: (22)..(22)
<223> OTHER INFORMATION: T -> A transversion
<220> FEATURE:
<221> NAME/KEY: mutation
<222> LOCATION: (961)..(961)
<223> OTHER INFORMATION: G -> A transition

<400> SEQUENCE: 7
```

```
gtg agc aca aac acg acc ccc acc agc tgg aca aac cca ctg cgc gac      48
Met Ser Thr Asn Thr Thr Pro Thr Ser Trp Thr Asn Pro Leu Arg Asp
1               5                   10                  15 ccg cag gat aaa cga ctc ccc cgc atc gct ggc cct tcc ggc atg gtg      96
Pro Gln Asp Lys Arg Leu Pro Arg Ile Ala Gly Pro Ser Gly Met Val
                20                  25                  30 atc ttc ggt gtc act ggc gac ttg gct cga aag aag ctg ctc ccc gcc     144
Ile Phe Gly Val Thr Gly Asp Leu Ala Arg Lys Lys Leu Leu Pro Ala
            35                  40                  45 att tat gat cta gca aac cgc gga ttg ctg ccc cca gga ttc tcg ttg     192
Ile Tyr Asp Leu Ala Asn Arg Gly Leu Leu Pro Pro Gly Phe Ser Leu
        50                  55                  60
```

```
gta ggt tac ggc cgc cgc gaa tgg tcc aaa gaa gac ttt gaa aaa tac      240
Val Gly Tyr Gly Arg Arg Glu Trp Ser Lys Glu Asp Phe Glu Lys Tyr
 65                  70                  75                  80 gta cgc gat gcc gca agt gct ggt gct cgt acg gaa ttc cgt gaa aat      288
Val Arg Asp Ala Ala Ser Ala Gly Ala Arg Thr Glu Phe Arg Glu Asn
                 85                  90                  95 gtt tgg gag cgc ctc gcc gag ggt atg gaa ttt gtt cgc ggc aac ttt      336
Val Trp Glu Arg Leu Ala Glu Gly Met Glu Phe Val Arg Gly Asn Phe
            100                 105                 110 gat gat gat gca gct ttc gac aac ctc gct gca aca ctc aag cgc atc      384
Asp Asp Asp Ala Ala Phe Asp Asn Leu Ala Ala Thr Leu Lys Arg Ile
        115                 120                 125 gac aaa acc cgc ggc acc gcc ggc aac tgg gct tac tac ctg tcc att      432
Asp Lys Thr Arg Gly Thr Ala Gly Asn Trp Ala Tyr Tyr Leu Ser Ile
    130                 135                 140 cca cca gat tcc ttc aca gcg gtc tgc cac cag ctg gag cgt tcc ggc      480
Pro Pro Asp Ser Phe Thr Ala Val Cys His Gln Leu Glu Arg Ser Gly
145                 150                 155                 160 atg gct gaa tcc acc gaa gaa gca tgg cgc cgc gtg atc atc gag aag      528
Met Ala Glu Ser Thr Glu Glu Ala Trp Arg Arg Val Ile Ile Glu Lys
                165                 170                 175 cct ttc ggc cac aac ctc gaa tcc gca cac gag ctc aac cag ctg gtc      576
Pro Phe Gly His Asn Leu Glu Ser Ala His Glu Leu Asn Gln Leu Val
            180                 185                 190 aac gca gtc ttc cca gaa tct tct gtg ttc cgc atc gac cac tat ttg      624
Asn Ala Val Phe Pro Glu Ser Ser Val Phe Arg Ile Asp His Tyr Leu
        195                 200                 205 ggc aag gaa aca gtt caa aac atc ctg gct ctg cgt ttt gct aac cag      672
Gly Lys Glu Thr Val Gln Asn Ile Leu Ala Leu Arg Phe Ala Asn Gln
    210                 215                 220 ctg ttt gag cca ctg tgg aac tcc aac tac gtt gac cac gtc cag atc      720
Leu Phe Glu Pro Leu Trp Asn Ser Asn Tyr Val Asp His Val Gln Ile
225                 230                 235                 240 acc atg gct gaa gat att ggc ttg ggt gga cgt gct ggt tac tac gac      768
Thr Met Ala Glu Asp Ile Gly Leu Gly Gly Arg Ala Gly Tyr Tyr Asp
                245                 250                 255 ggc atc ggc gca gcc cgc gac gtc atc cag aac cac ctg atc cag ctc      816
Gly Ile Gly Ala Ala Arg Asp Val Ile Gln Asn His Leu Ile Gln Leu
            260                 265                 270 ttg gct ctg gtt gcc atg gaa gaa cca att tct ttc gtg cca gcg cag      864
Leu Ala Leu Val Ala Met Glu Glu Pro Ile Ser Phe Val Pro Ala Gln
        275                 280                 285 ctg cag gca gaa aag atc aag gtg ctc tct gcg aca aag ccg tgc tac      912
Leu Gln Ala Glu Lys Ile Lys Val Leu Ser Ala Thr Lys Pro Cys Tyr
    290                 295                 300 cca ttg gat aaa acc tcc gct cgt ggt cag tac gct gcc ggt tgg cag      960
Pro Leu Asp Lys Thr Ser Ala Arg Gly Gln Tyr Ala Ala Gly Trp Gln
305                 310                 315                 320 agc tct gag tta gtc aag gga ctt cgc gaa gaa gat ggc ttc aac cct     1008
Ser Ser Glu Leu Val Lys Gly Leu Arg Glu Glu Asp Gly Phe Asn Pro
                325                 330                 335 gag tcc acc act gag act ttt gcg gct tgt acc tta gag atc acg tct     1056
Glu Ser Thr Thr Glu Thr Phe Ala Ala Cys Thr Leu Glu Ile Thr Ser
            340                 345                 350 cgt cgc tgg gct ggt gtg ccg ttc tac ctg cgc acc ggt aag cgt ctt     1104
Arg Arg Trp Ala Gly Val Pro Phe Tyr Leu Arg Thr Gly Lys Arg Leu
        355                 360                 365 ggt cgc cgt gtt act gag att gcc gtg gtg ttt aaa gac gca cca cac     1152
Gly Arg Arg Val Thr Glu Ile Ala Val Val Phe Lys Asp Ala Pro His
    370                 375                 380
```

```
cag cct ttc gac ggc gac atg act gta tcc ctt ggc caa aac gcc atc    1200
Gln Pro Phe Asp Gly Asp Met Thr Val Ser Leu Gly Gln Asn Ala Ile
385                 390                 395                 400 gtg att cgc gtg cag cct gat gaa ggt gtc ctc atc cgc ttc ggt tcc    1248
Val Ile Arg Val Gln Pro Asp Glu Gly Val Leu Ile Arg Phe Gly Ser
            405                 410                 415 aag gtt cca ggt tct gcc atg gaa gtc cgt gac gtc aac atg gac ttc    1296
Lys Val Pro Gly Ser Ala Met Glu Val Arg Asp Val Asn Met Asp Phe
        420                 425                 430 tcc tac tca gaa tcc ttc act gaa gaa tca cct gaa gca tac gag cgc    1344
Ser Tyr Ser Glu Ser Phe Thr Glu Glu Ser Pro Glu Ala Tyr Glu Arg
    435                 440                 445 ctc att ttg gat gcg ctg tta gat gaa tcc agc ctc ttc cct acc aac    1392
Leu Ile Leu Asp Ala Leu Leu Asp Glu Ser Ser Leu Phe Pro Thr Asn
450                 455                 460 gag gaa gtg gaa ctg agc tgg aag att ctg gat cca att ctt gaa gca    1440
Glu Glu Val Glu Leu Ser Trp Lys Ile Leu Asp Pro Ile Leu Glu Ala
465                 470                 475                 480 tgg gat gcc gat gga gaa cca gag gat tac cca gcg ggt acg tgg ggt    1488
Trp Asp Ala Asp Gly Glu Pro Glu Asp Tyr Pro Ala Gly Thr Trp Gly
            485                 490                 495 cca aag agc gct gat gaa atg ctt tcc cgc aac ggt cac acc tgg cgc    1536
Pro Lys Ser Ala Asp Glu Met Leu Ser Arg Asn Gly His Thr Trp Arg
        500                 505                 510 agg cca taa                                                        1545
Arg Pro
```

<210> SEQ ID NO 8
<211> LENGTH: 514
<212> TYPE: PRT
<213> ORGANISM: Corynebacterium glutamicum

<400> SEQUENCE: 8

```
Met Ser Thr Asn Thr Thr Pro Thr Ser Trp Thr Asn Pro Leu Arg Asp
1               5                   10                  15

Pro Gln Asp Lys Arg Leu Pro Arg Ile Ala Gly Pro Ser Gly Met Val
            20                  25                  30

Ile Phe Gly Val Thr Gly Asp Leu Ala Arg Lys Lys Leu Leu Pro Ala
        35                  40                  45

Ile Tyr Asp Leu Ala Asn Arg Gly Leu Leu Pro Pro Gly Phe Ser Leu
    50                  55                  60

Val Gly Tyr Gly Arg Arg Glu Trp Ser Lys Glu Asp Phe Glu Lys Tyr
65                  70                  75                  80

Val Arg Asp Ala Ala Ser Ala Gly Ala Arg Thr Glu Phe Arg Glu Asn
                85                  90                  95

Val Trp Glu Arg Leu Ala Glu Gly Met Glu Phe Val Arg Gly Asn Phe
            100                 105                 110

Asp Asp Asp Ala Ala Phe Asp Asn Leu Ala Ala Thr Leu Lys Arg Ile
        115                 120                 125

Asp Lys Thr Arg Gly Thr Ala Gly Asn Trp Ala Tyr Tyr Leu Ser Ile
    130                 135                 140

Pro Pro Asp Ser Phe Thr Ala Val Cys His Gln Leu Glu Arg Ser Gly
145                 150                 155                 160

Met Ala Glu Ser Thr Glu Glu Ala Trp Arg Arg Val Ile Ile Glu Lys
                165                 170                 175

Pro Phe Gly His Asn Leu Glu Ser Ala His Glu Leu Asn Gln Leu Val
            180                 185                 190
```

```
Asn Ala Val Phe Pro Glu Ser Ser Val Phe Arg Ile Asp His Tyr Leu
            195                 200                 205

Gly Lys Glu Thr Val Gln Asn Ile Leu Ala Leu Arg Phe Ala Asn Gln
        210                 215                 220

Leu Phe Glu Pro Leu Trp Asn Ser Asn Tyr Val Asp His Val Gln Ile
225                 230                 235                 240

Thr Met Ala Glu Asp Ile Gly Leu Gly Gly Arg Ala Gly Tyr Tyr Asp
                245                 250                 255

Gly Ile Gly Ala Ala Arg Asp Val Ile Gln Asn His Leu Ile Gln Leu
            260                 265                 270

Leu Ala Leu Val Ala Met Glu Glu Pro Ile Ser Phe Val Pro Ala Gln
        275                 280                 285

Leu Gln Ala Glu Lys Ile Lys Val Leu Ser Ala Thr Lys Pro Cys Tyr
    290                 295                 300

Pro Leu Asp Lys Thr Ser Ala Arg Gly Gln Tyr Ala Ala Gly Trp Gln
305                 310                 315                 320

Ser Ser Glu Leu Val Lys Gly Leu Arg Glu Glu Asp Gly Phe Asn Pro
                325                 330                 335

Glu Ser Thr Thr Glu Thr Phe Ala Ala Cys Thr Leu Glu Ile Thr Ser
            340                 345                 350

Arg Arg Trp Ala Gly Val Pro Phe Tyr Leu Arg Thr Gly Lys Arg Leu
        355                 360                 365

Gly Arg Arg Val Thr Glu Ile Ala Val Val Phe Lys Asp Ala Pro His
    370                 375                 380

Gln Pro Phe Asp Gly Asp Met Thr Val Ser Leu Gly Gln Asn Ala Ile
385                 390                 395                 400

Val Ile Arg Val Gln Pro Asp Glu Gly Val Leu Ile Arg Phe Gly Ser
                405                 410                 415

Lys Val Pro Gly Ser Ala Met Glu Val Arg Asp Val Asn Met Asp Phe
            420                 425                 430

Ser Tyr Ser Glu Ser Phe Thr Glu Glu Ser Pro Glu Ala Tyr Glu Arg
        435                 440                 445

Leu Ile Leu Asp Ala Leu Leu Asp Glu Ser Ser Leu Phe Pro Thr Asn
    450                 455                 460

Glu Glu Val Glu Leu Ser Trp Lys Ile Leu Asp Pro Ile Leu Glu Ala
465                 470                 475                 480

Trp Asp Ala Asp Gly Glu Pro Glu Asp Tyr Pro Ala Gly Thr Trp Gly
                485                 490                 495

Pro Lys Ser Ala Asp Glu Met Leu Ser Arg Asn Gly His Thr Trp Arg
            500                 505                 510

Arg Pro

<210> SEQ ID NO 9
<211> LENGTH: 1545
<212> TYPE: DNA
<213> ORGANISM: Corynebacterium glutamicum
<220> FEATURE:
<221> NAME/KEY: CDS
<222> LOCATION: (1)..(1542)
<220> FEATURE:
<221> NAME/KEY: mutation
<222> LOCATION: (22)..(22)
<223> OTHER INFORMATION: T -> A  transversion
<220> FEATURE:
<221> NAME/KEY: mutation
<222> LOCATION: (138)..(138)
<223> OTHER INFORMATION: C -> T transition
```

```
<220> FEATURE:
<221> NAME/KEY: mutation
<222> LOCATION: (279)..(279)
<223> OTHER INFORMATION: C -> T transition
<220> FEATURE:
<221> NAME/KEY: mutation
<222> LOCATION: (738)..(738)
<223> OTHER INFORMATION: T -> C transition
<220> FEATURE:
<221> NAME/KEY: mutation
<222> LOCATION: (777)..(777)
<223> OTHER INFORMATION: C -> T transition
<220> FEATURE:
<221> NAME/KEY: mutation
<222> LOCATION: (906)..(906)
<223> OTHER INFORMATION: G -> A transition
<220> FEATURE:
<221> NAME/KEY: mutation
<222> LOCATION: (961)..(961)
<223> OTHER INFORMATION: G -> A transition

<400> SEQUENCE: 9 gtg agc aca aac acg acc ccc acc agc tgg aca aac cca ctg cgc gac    48
Met Ser Thr Asn Thr Thr Pro Thr Ser Trp Thr Asn Pro Leu Arg Asp
1               5                   10                  15 ccg cag gat aaa cga ctc ccc cgc atc gct ggc cct tcc ggc atg gtg    96
Pro Gln Asp Lys Arg Leu Pro Arg Ile Ala Gly Pro Ser Gly Met Val
            20                  25                  30 atc ttc ggt gtc act ggc gac ttg gct cga aag aag ctg ctt ccc gcc   144
Ile Phe Gly Val Thr Gly Asp Leu Ala Arg Lys Lys Leu Leu Pro Ala
        35                  40                  45 att tat gat cta gca aac cgc gga ttg ctg ccc cca gga ttc tcg ttg   192
Ile Tyr Asp Leu Ala Asn Arg Gly Leu Leu Pro Pro Gly Phe Ser Leu
50                  55                  60 gta ggt tac ggc cgc cgc gaa tgg tcc aaa gaa gac ttt gaa aaa tac   240
Val Gly Tyr Gly Arg Arg Glu Trp Ser Lys Glu Asp Phe Glu Lys Tyr
65                  70                  75                  80 gta cgc gat gcc gca agt gct ggt gct cgt acg gaa ttt cgt gaa aat   288
Val Arg Asp Ala Ala Ser Ala Gly Ala Arg Thr Glu Phe Arg Glu Asn
                85                  90                  95 gtt tgg gag cgc ctc gcc gag ggt atg gaa ttt gtt cgc ggc aac ttt   336
Val Trp Glu Arg Leu Ala Glu Gly Met Glu Phe Val Arg Gly Asn Phe
            100                 105                 110 gat gat gat gca gct ttc gac aac ctc gct gca aca ctc aag cgc atc   384
Asp Asp Asp Ala Ala Phe Asp Asn Leu Ala Ala Thr Leu Lys Arg Ile
        115                 120                 125 gac aaa acc cgc ggc acc gcc ggc aac tgg gct tac tac ctg tcc att   432
Asp Lys Thr Arg Gly Thr Ala Gly Asn Trp Ala Tyr Tyr Leu Ser Ile
    130                 135                 140 cca cca gat tcc ttc aca gcg gtc tgc cac cag ctg gag cgt tcc ggc   480
Pro Pro Asp Ser Phe Thr Ala Val Cys His Gln Leu Glu Arg Ser Gly
145                 150                 155                 160 atg gct gaa tcc acc gaa gaa gca tgg cgc cgc gtg atc atc gag aag   528
Met Ala Glu Ser Thr Glu Glu Ala Trp Arg Arg Val Ile Ile Glu Lys
                165                 170                 175 cct ttc ggc cac aac ctc gaa tcc gca cac gag ctc aac cag ctg gtc   576
Pro Phe Gly His Asn Leu Glu Ser Ala His Glu Leu Asn Gln Leu Val
            180                 185                 190 aac gca gtc ttc cca gaa tct tct gtg ttc cgc atc gac cac tat ttg   624
Asn Ala Val Phe Pro Glu Ser Ser Val Phe Arg Ile Asp His Tyr Leu
        195                 200                 205 ggc aag gaa aca gtt caa aac atc ctg gct ctg cgt ttt gct aac cag   672
Gly Lys Glu Thr Val Gln Asn Ile Leu Ala Leu Arg Phe Ala Asn Gln
    210                 215                 220
```

```
ctg ttt gag cca ctg tgg aac tcc aac tac gtt gac cac gtc cag atc      720
Leu Phe Glu Pro Leu Trp Asn Ser Asn Tyr Val Asp His Val Gln Ile
225                 230                 235                 240 acc atg gct gaa gat atc ggc ttg ggt gga cgt gct ggt tac tac gac      768
Thr Met Ala Glu Asp Ile Gly Leu Gly Gly Arg Ala Gly Tyr Tyr Asp
            245                 250                 255 ggc atc ggt gca gcc cgc gac gtc atc cag aac cac ctg atc cag ctc      816
Gly Ile Gly Ala Ala Arg Asp Val Ile Gln Asn His Leu Ile Gln Leu
        260                 265                 270 ttg gct ctg gtt gcc atg gaa gaa cca att tct ttc gtg cca gcg cag      864
Leu Ala Leu Val Ala Met Glu Glu Pro Ile Ser Phe Val Pro Ala Gln
    275                 280                 285 ctg cag gca gaa aag atc aag gtg ctc tct gcg aca aag cca tgc tac      912
Leu Gln Ala Glu Lys Ile Lys Val Leu Ser Ala Thr Lys Pro Cys Tyr
290                 295                 300 cca ttg gat aaa acc tcc gct cgt ggt cag tac gct gcc ggt tgg cag      960
Pro Leu Asp Lys Thr Ser Ala Arg Gly Gln Tyr Ala Ala Gly Trp Gln
305                 310                 315                 320 agc tct gag tta gtc aag gga ctt cgc gaa gaa gat ggc ttc aac cct     1008
Ser Ser Glu Leu Val Lys Gly Leu Arg Glu Glu Asp Gly Phe Asn Pro
            325                 330                 335 gag tcc acc act gag act ttt gcg gct tgt acc tta gag atc acg tct     1056
Glu Ser Thr Thr Glu Thr Phe Ala Ala Cys Thr Leu Glu Ile Thr Ser
        340                 345                 350 cgt cgc tgg gct ggt gtg ccg ttc tac ctg cgc acc ggt aag cgt ctt     1104
Arg Arg Trp Ala Gly Val Pro Phe Tyr Leu Arg Thr Gly Lys Arg Leu
    355                 360                 365 ggt cgc cgt gtt act gag att gcc gtg gtg ttt aaa gac gca cca cac     1152
Gly Arg Arg Val Thr Glu Ile Ala Val Val Phe Lys Asp Ala Pro His
370                 375                 380 cag cct ttc gac ggc gac atg act gta tcc ctt ggc caa aac gcc atc     1200
Gln Pro Phe Asp Gly Asp Met Thr Val Ser Leu Gly Gln Asn Ala Ile
385                 390                 395                 400 gtg att cgc gtg cag cct gat gaa ggt gtg ctc atc cgc ttc ggt tcc     1248
Val Ile Arg Val Gln Pro Asp Glu Gly Val Leu Ile Arg Phe Gly Ser
            405                 410                 415 aag gtt cca ggt tct gcc atg gaa gtc cgt gac gtc aac atg gac ttc     1296
Lys Val Pro Gly Ser Ala Met Glu Val Arg Asp Val Asn Met Asp Phe
        420                 425                 430 tcc tac tca gaa tcc ttc act gaa gaa tca cct gaa gca tac gag cgc     1344
Ser Tyr Ser Glu Ser Phe Thr Glu Glu Ser Pro Glu Ala Tyr Glu Arg
    435                 440                 445 ctc att ttg gat gcg ctg tta gat gaa tcc agc ctc ttc cct acc aac     1392
Leu Ile Leu Asp Ala Leu Leu Asp Glu Ser Ser Leu Phe Pro Thr Asn
450                 455                 460 gag gaa gtg gaa ctg agc tgg aag att ctg gat cca att ctt gaa gca     1440
Glu Glu Val Glu Leu Ser Trp Lys Ile Leu Asp Pro Ile Leu Glu Ala
465                 470                 475                 480 tgg gat gcc gat gga gaa cca gag gat tac cca gcg ggt acg tgg ggt     1488
Trp Asp Ala Asp Gly Glu Pro Glu Asp Tyr Pro Ala Gly Thr Trp Gly
            485                 490                 495 cca aag agc gct gat gaa atg ctt tcc cgc aac ggt cac acc tgg cgc     1536
Pro Lys Ser Ala Asp Glu Met Leu Ser Arg Asn Gly His Thr Trp Arg
        500                 505                 510 agg cca taa                                                         1545
Arg Pro

<210> SEQ ID NO 10
<211> LENGTH: 514
<212> TYPE: PRT
```

<213> ORGANISM: Corynebacterium glutamicum

<400> SEQUENCE: 10

| Met | Ser | Thr | Asn | Thr | Pro | Thr | Ser | Trp | Thr | Asn | Pro | Leu | Arg | Asp |
|---|---|---|---|---|---|---|---|---|---|---|---|---|---|---|
| 1 | | | | 5 | | | | | 10 | | | | | 15 |

| Pro | Gln | Asp | Lys | Arg | Leu | Pro | Arg | Ile | Ala | Gly | Pro | Ser | Gly | Met | Val |
|---|---|---|---|---|---|---|---|---|---|---|---|---|---|---|---|
| | | | 20 | | | | | 25 | | | | | 30 | | |

Ile Phe Gly Val Thr Gly Asp Leu Ala Arg Lys Lys Leu Leu Pro Ala
            35                  40                  45

Ile Tyr Asp Leu Ala Asn Arg Gly Leu Leu Pro Pro Gly Phe Ser Leu
50                      55                  60

Val Gly Tyr Gly Arg Arg Glu Trp Ser Lys Glu Asp Phe Glu Lys Tyr
65                  70                  75                  80

Val Arg Asp Ala Ala Ser Ala Gly Ala Arg Thr Glu Phe Arg Glu Asn
                85                  90                  95

Val Trp Glu Arg Leu Ala Glu Gly Met Glu Phe Val Arg Gly Asn Phe
            100                 105                 110

Asp Asp Asp Ala Ala Phe Asp Asn Leu Ala Ala Thr Leu Lys Arg Ile
        115                 120                 125

Asp Lys Thr Arg Gly Thr Ala Gly Asn Trp Ala Tyr Tyr Leu Ser Ile
130                 135                 140

Pro Pro Asp Ser Phe Thr Ala Val Cys His Gln Leu Glu Arg Ser Gly
145                 150                 155                 160

Met Ala Glu Ser Thr Glu Glu Ala Trp Arg Arg Val Ile Ile Glu Lys
                165                 170                 175

Pro Phe Gly His Asn Leu Glu Ser Ala His Glu Leu Asn Gln Leu Val
            180                 185                 190

Asn Ala Val Phe Pro Glu Ser Ser Val Phe Arg Ile Asp His Tyr Leu
        195                 200                 205

Gly Lys Glu Thr Val Gln Asn Ile Leu Ala Leu Arg Phe Ala Asn Gln
210                 215                 220

Leu Phe Glu Pro Leu Trp Asn Ser Asn Tyr Val Asp His Val Gln Ile
225                 230                 235                 240

Thr Met Ala Glu Asp Ile Gly Leu Gly Gly Arg Ala Gly Tyr Tyr Asp
                245                 250                 255

Gly Ile Gly Ala Ala Arg Asp Val Ile Gln Asn His Leu Ile Gln Leu
            260                 265                 270

Leu Ala Leu Val Ala Met Glu Glu Pro Ile Ser Phe Val Pro Ala Gln
        275                 280                 285

Leu Gln Ala Glu Lys Ile Lys Val Leu Ser Ala Thr Lys Pro Cys Tyr
290                 295                 300

Pro Leu Asp Lys Thr Ser Ala Arg Gly Gln Tyr Ala Ala Gly Trp Gln
305                 310                 315                 320

Ser Ser Glu Leu Val Lys Gly Leu Arg Glu Glu Asp Gly Phe Asn Pro
                325                 330                 335

Glu Ser Thr Thr Glu Thr Phe Ala Ala Cys Thr Leu Glu Ile Thr Ser
            340                 345                 350

Arg Arg Trp Ala Gly Val Pro Phe Tyr Leu Arg Thr Gly Lys Arg Leu
        355                 360                 365

Gly Arg Arg Val Thr Glu Ile Ala Val Val Phe Lys Asp Ala Pro His
370                 375                 380

Gln Pro Phe Asp Gly Asp Met Thr Val Ser Leu Gly Gln Asn Ala Ile
385                 390                 395                 400

-continued

```
Val Ile Arg Val Gln Pro Asp Glu Gly Val Leu Ile Arg Phe Gly Ser
                405                 410                 415
Lys Val Pro Gly Ser Ala Met Glu Val Arg Asp Val Asn Met Asp Phe
            420                 425                 430
Ser Tyr Ser Glu Ser Phe Thr Glu Glu Ser Pro Glu Ala Tyr Glu Arg
        435                 440                 445
Leu Ile Leu Asp Ala Leu Leu Asp Glu Ser Ser Leu Phe Pro Thr Asn
    450                 455                 460
Glu Glu Val Glu Leu Ser Trp Lys Ile Leu Asp Pro Ile Leu Glu Ala
465                 470                 475                 480
Trp Asp Ala Asp Gly Glu Pro Glu Asp Tyr Pro Ala Gly Thr Trp Gly
                485                 490                 495
Pro Lys Ser Ala Asp Glu Met Leu Ser Arg Asn Gly His Thr Trp Arg
            500                 505                 510
Arg Pro

<210> SEQ ID NO 11
<211> LENGTH: 2100
<212> TYPE: DNA
<213> ORGANISM: Corynebacterium glutamicum
<220> FEATURE:
<221> NAME/KEY: mutation
<222> LOCATION: (208)..(208)
<223> OTHER INFORMATION: A -> G transition
<220> FEATURE:
<221> NAME/KEY: mutation
<222> LOCATION: (235)..(235)
<223> OTHER INFORMATION: G -> A transition
<220> FEATURE:
<221> NAME/KEY: mutation
<222> LOCATION: (245)..(245)
<223> OTHER INFORMATION: T -> C transition
<220> FEATURE:
<221> NAME/KEY: mutation
<222> LOCATION: (257)..(257)
<223> OTHER INFORMATION: A -> G transition
<220> FEATURE:
<221> NAME/KEY: mutation
<222> LOCATION: (299)..(299)
<223> OTHER INFORMATION: A -> G transition
<220> FEATURE:
<221> NAME/KEY: CDS
<222> LOCATION: (308)..(1849)
<220> FEATURE:
<221> NAME/KEY: mutation
<222> LOCATION: (329)..(329)
<223> OTHER INFORMATION: T -> A transversion
<220> FEATURE:
<221> NAME/KEY: mutation
<222> LOCATION: (445)..(445)
<223> OTHER INFORMATION: C -> T transition
<220> FEATURE:
<221> NAME/KEY: mutation
<222> LOCATION: (586)..(586)
<223> OTHER INFORMATION: C -> T transition
<220> FEATURE:
<221> NAME/KEY: mutation
<222> LOCATION: (1045)..(1045)
<223> OTHER INFORMATION: T -> C transition
<220> FEATURE:
<221> NAME/KEY: mutation
<222> LOCATION: (1084)..(1084)
<223> OTHER INFORMATION: C -> T transition
<220> FEATURE:
<221> NAME/KEY: mutation
<222> LOCATION: (1213)..(1213)
<223> OTHER INFORMATION: G -> A transition
<220> FEATURE:
<221> NAME/KEY: mutation
<222> LOCATION: (1268)..(1268)
<223> OTHER INFORMATION: G -> A transition
```

-continued

<400> SEQUENCE: 11

```
tcgacgcggt tctggagcag ggcaacctgc acggtgacac cctgtccaac tccgcggcag      60
aagctgacgc tgtgttctcc cagcttgagg ctctgggcgt tgacttggca gatgtcttcc     120
aggtcctgga gaccgagggt gtggacaagt tcgttgcttc ttggagcgaa ctgcttgagt     180
ccatggaagc tcgcctgaag tagaatcggc acgctgcatc agtaacgcg acataaaatc      240 gaatcagttc gatcttgtgt ggccgttaca catctttcat taaagaaagg atcgtgacgc     300
```

| | | | | | | | | | | | | | | | |
|---|---|---|---|---|---|---|---|---|---|---|---|---|---|---|---|
| taccatc | gtg | agc | aca | aac | acg | acc | ccc | acc | agc | tgg | aca | aac | cca | ctg | 349 |
| | Met | Ser | Thr | Asn | Thr | Thr | Pro | Thr | Ser | Trp | Thr | Asn | Pro | Leu | |
| | 1 | | | | 5 | | | | | 10 | | | | | |

```
cgc gac ccg cag gat aaa cga ctc ccc cgc atc gct ggc cct tcc ggc       397
Arg Asp Pro Gln Asp Lys Arg Leu Pro Arg Ile Ala Gly Pro Ser Gly
 15              20                  25                  30 atg gtg atc ttc ggt gtc act ggc gac ttg gct cga aag aag ctg ctt       445
Met Val Ile Phe Gly Val Thr Gly Asp Leu Ala Arg Lys Lys Leu Leu
                 35                  40                  45 ccc gcc att tat gat cta gca aac cgc gga ttg ctg ccc cca gga ttc       493
Pro Ala Ile Tyr Asp Leu Ala Asn Arg Gly Leu Leu Pro Pro Gly Phe
         50                  55                  60 tcg ttg gta ggt tac ggc cgc gcc gaa tgg tcc aaa gaa gac ttt gaa       541
Ser Leu Val Gly Tyr Gly Arg Arg Glu Trp Ser Lys Glu Asp Phe Glu
             65                  70                  75 aaa tac gta cgc gat gcc gca agt gct ggt gct cgt acg gaa ttt cgt       589
Lys Tyr Val Arg Asp Ala Ala Ser Ala Gly Ala Arg Thr Glu Phe Arg
 80                  85                  90 gaa aat gtt tgg gag cgc ctc gcc gag ggt atg gaa ttt gtt cgc ggc       637
Glu Asn Val Trp Glu Arg Leu Ala Glu Gly Met Glu Phe Val Arg Gly
 95                 100                 105                 110 aac ttt gat gat gat gca gct ttc gac aac ctc gct gca aca ctc aag       685
Asn Phe Asp Asp Asp Ala Ala Phe Asp Asn Leu Ala Ala Thr Leu Lys
                115                 120                 125 cgc atc gac aaa acc cgc ggc acc gcc ggc aac tgg gct tac tac ctg       733
Arg Ile Asp Lys Thr Arg Gly Thr Ala Gly Asn Trp Ala Tyr Tyr Leu
        130                 135                 140 tcc att cca cca gat tcc ttc aca gcg gtc tgc cac cag ctg gag cgt       781
Ser Ile Pro Pro Asp Ser Phe Thr Ala Val Cys His Gln Leu Glu Arg
            145                 150                 155 tcc ggc atg gct gaa tcc acc gaa gaa gca tgg cgc cgc gtg atc atc       829
Ser Gly Met Ala Glu Ser Thr Glu Glu Ala Trp Arg Arg Val Ile Ile
160                 165                 170 gag aag cct ttc ggc cac aac ctc gaa tcc gca cac gag ctc aac cag       877
Glu Lys Pro Phe Gly His Asn Leu Glu Ser Ala His Glu Leu Asn Gln
175                 180                 185                 190 ctg gtc aac gca gtc ttc cca gaa tct tct gtg ttc cgc atc gac cac       925
Leu Val Asn Ala Val Phe Pro Glu Ser Ser Val Phe Arg Ile Asp His
                195                 200                 205 tat ttg ggc aag gaa aca gtt caa aac atc ctg gct ctg cgt ttt gct       973
Tyr Leu Gly Lys Glu Thr Val Gln Asn Ile Leu Ala Leu Arg Phe Ala
        210                 215                 220 aac cag ctg ttt gag cca ctg tgg aac tcc aac tac gtt gac cac gtc      1021
Asn Gln Leu Phe Glu Pro Leu Trp Asn Ser Asn Tyr Val Asp His Val
            225                 230                 235 cag atc acc atg gct gaa gat atc ggc ttg ggt gga cgt gct ggt tac      1069
Gln Ile Thr Met Ala Glu Asp Ile Gly Leu Gly Gly Arg Ala Gly Tyr
240                 245                 250 tac gac ggc atc ggt gca gcc cgc gac gtc atc cag aac cac ctg atc      1117
Tyr Asp Gly Ile Gly Ala Ala Arg Asp Val Ile Gln Asn His Leu Ile
```

-continued

```
                255                 260                 265                 270 cag ctc ttg gct ctg gtt gcc atg gaa gaa cca att tct ttc gtg cca    1165
Gln Leu Leu Ala Leu Val Ala Met Glu Glu Pro Ile Ser Phe Val Pro
            275                 280                 285 gcg cag ctg cag gca gaa aag atc aag gtg ctc tct gcg aca aag cca    1213
Ala Gln Leu Gln Ala Glu Lys Ile Lys Val Leu Ser Ala Thr Lys Pro
        290                 295                 300 tgc tac cca ttg gat aaa acc tcc gct cgt ggt cag tac gct gcc ggt    1261
Cys Tyr Pro Leu Asp Lys Thr Ser Ala Arg Gly Gln Tyr Ala Ala Gly
    305                 310                 315 tgg cag agc tct gag tta gtc aag gga ctt cgc gaa gaa gat ggc ttc    1309
Trp Gln Ser Ser Glu Leu Val Lys Gly Leu Arg Glu Glu Asp Gly Phe
320                 325                 330 aac cct gag tcc acc act gag act ttt gcg gct tgt acc tta gag atc    1357
Asn Pro Glu Ser Thr Thr Glu Thr Phe Ala Ala Cys Thr Leu Glu Ile
335                 340                 345                 350 acg tct cgt cgc tgg gct ggt gtg ccg ttc tac ctg cgc acc ggt aag    1405
Thr Ser Arg Arg Trp Ala Gly Val Pro Phe Tyr Leu Arg Thr Gly Lys
                355                 360                 365 cgt ctt ggt cgc cgt gtt act gag att gcc gtg gtg ttt aaa gac gca    1453
Arg Leu Gly Arg Arg Val Thr Glu Ile Ala Val Val Phe Lys Asp Ala
            370                 375                 380 cca cac cag cct ttc gac ggc gac atg act gta tcc ctt ggc caa aac    1501
Pro His Gln Pro Phe Asp Gly Asp Met Thr Val Ser Leu Gly Gln Asn
        385                 390                 395 gcc atc gtg att cgc gtg cag cct gat gaa ggt gtg ctc atc cgc ttc    1549
Ala Ile Val Ile Arg Val Gln Pro Asp Glu Gly Val Leu Ile Arg Phe
    400                 405                 410 ggt tcc aag gtt cca ggt tct gcc atg gaa gtc cgt gac gtc aac atg    1597
Gly Ser Lys Val Pro Gly Ser Ala Met Glu Val Arg Asp Val Asn Met
415                 420                 425                 430 gac ttc tcc tac tca gaa tcc ttc act gaa gaa tca cct gaa gca tac    1645
Asp Phe Ser Tyr Ser Glu Ser Phe Thr Glu Glu Ser Pro Glu Ala Tyr
                435                 440                 445 gag cgc ctc att ttg gat gcg ctg tta gat gaa tcc agc ctc ttc cct    1693
Glu Arg Leu Ile Leu Asp Ala Leu Leu Asp Glu Ser Ser Leu Phe Pro
            450                 455                 460 acc aac gag gaa gtg gaa ctg agc tgg aag att ctg gat cca att ctt    1741
Thr Asn Glu Glu Val Glu Leu Ser Trp Lys Ile Leu Asp Pro Ile Leu
        465                 470                 475 gaa gca tgg gat gcc gat gga gaa cca gag gat tac cca gcg ggt acg    1789
Glu Ala Trp Asp Ala Asp Gly Glu Pro Glu Asp Tyr Pro Ala Gly Thr
    480                 485                 490 tgg ggt cca aag agc gct gat gaa atg ctt tcc cgc aac ggt cac acc    1837
Trp Gly Pro Lys Ser Ala Asp Glu Met Leu Ser Arg Asn Gly His Thr
495                 500                 505                 510 tgg cgc agg cca taatttaggg gcaaaaaatg atctttgaac ttccggatac        1889
Trp Arg Arg Pro caccacccag caaatttcca agaccctaac tcgactgcgt gaatcgggca cccaggtcac  1949
caccggccga gtgctcaccc tcatcgtggt cactgactcc gaaagcgatg tcgctgcagt  2009
taccgagtcc accaatgaag cctcgcgcga gcacccatct cgcgtgatca ttttggtggt  2069
tggcgataaa actgcagaaa acaaagttga c                                 2100

<210> SEQ ID NO 12
<211> LENGTH: 514
<212> TYPE: PRT
<213> ORGANISM: Corynebacterium glutamicum
```

<400> SEQUENCE: 12

```
Met Ser Thr Asn Thr Thr Pro Thr Ser Trp Thr Asn Pro Leu Arg Asp
1               5                   10                  15

Pro Gln Asp Lys Arg Leu Pro Arg Ile Ala Gly Pro Ser Gly Met Val
            20                  25                  30

Ile Phe Gly Val Thr Gly Asp Leu Ala Arg Lys Lys Leu Leu Pro Ala
        35                  40                  45

Ile Tyr Asp Leu Ala Asn Arg Gly Leu Leu Pro Pro Gly Phe Ser Leu
    50                  55                  60

Val Gly Tyr Gly Arg Arg Glu Trp Ser Lys Glu Asp Phe Glu Lys Tyr
65                  70                  75                  80

Val Arg Asp Ala Ala Ser Ala Gly Ala Arg Thr Glu Phe Arg Glu Asn
                85                  90                  95

Val Trp Glu Arg Leu Ala Glu Gly Met Glu Phe Val Arg Gly Asn Phe
            100                 105                 110

Asp Asp Asp Ala Ala Phe Asp Asn Leu Ala Ala Thr Leu Lys Arg Ile
        115                 120                 125

Asp Lys Thr Arg Gly Thr Ala Gly Asn Trp Ala Tyr Tyr Leu Ser Ile
    130                 135                 140

Pro Pro Asp Ser Phe Thr Ala Val Cys His Gln Leu Glu Arg Ser Gly
145                 150                 155                 160

Met Ala Glu Ser Thr Glu Glu Ala Trp Arg Arg Val Ile Ile Glu Lys
                165                 170                 175

Pro Phe Gly His Asn Leu Glu Ser Ala His Glu Leu Asn Gln Leu Val
            180                 185                 190

Asn Ala Val Phe Pro Glu Ser Ser Val Phe Arg Ile Asp His Tyr Leu
        195                 200                 205

Gly Lys Glu Thr Val Gln Asn Ile Leu Ala Leu Arg Phe Ala Asn Gln
    210                 215                 220

Leu Phe Glu Pro Leu Trp Asn Ser Asn Tyr Val Asp His Val Gln Ile
225                 230                 235                 240

Thr Met Ala Glu Asp Ile Gly Leu Gly Gly Arg Ala Gly Tyr Tyr Asp
                245                 250                 255

Gly Ile Gly Ala Ala Arg Asp Val Ile Gln Asn His Leu Ile Gln Leu
            260                 265                 270

Leu Ala Leu Val Ala Met Glu Glu Pro Ile Ser Phe Val Pro Ala Gln
        275                 280                 285

Leu Gln Ala Glu Lys Ile Lys Val Leu Ser Ala Thr Lys Pro Cys Tyr
    290                 295                 300

Pro Leu Asp Lys Thr Ser Ala Arg Gly Gln Tyr Ala Ala Gly Trp Gln
305                 310                 315                 320

Ser Ser Glu Leu Val Lys Gly Leu Arg Glu Glu Asp Gly Phe Asn Pro
                325                 330                 335

Glu Ser Thr Thr Glu Thr Phe Ala Ala Cys Thr Leu Glu Ile Thr Ser
            340                 345                 350

Arg Arg Trp Ala Gly Val Pro Phe Tyr Leu Arg Thr Gly Lys Arg Leu
        355                 360                 365

Gly Arg Arg Val Thr Glu Ile Ala Val Phe Lys Asp Ala Pro His
    370                 375                 380

Gln Pro Phe Asp Gly Asp Met Thr Val Ser Leu Gly Gln Asn Ala Ile
385                 390                 395                 400

Val Ile Arg Val Gln Pro Asp Glu Gly Val Leu Ile Arg Phe Gly Ser
                405                 410                 415
```

-continued

```
Lys Val Pro Gly Ser Ala Met Glu Val Arg Asp Val Asn Met Asp Phe
            420                 425                 430
Ser Tyr Ser Glu Ser Phe Thr Glu Glu Ser Pro Glu Ala Tyr Glu Arg
        435                 440                 445
Leu Ile Leu Asp Ala Leu Leu Asp Glu Ser Ser Leu Phe Pro Thr Asn
    450                 455                 460
Glu Glu Val Glu Leu Ser Trp Lys Ile Leu Asp Pro Ile Leu Glu Ala
465                 470                 475                 480
Trp Asp Ala Asp Gly Glu Pro Glu Asp Tyr Pro Ala Gly Thr Trp Gly
                485                 490                 495
Pro Lys Ser Ala Asp Glu Met Leu Ser Arg Asn Gly His Thr Trp Arg
            500                 505                 510
Arg Pro

<210> SEQ ID NO 13
<211> LENGTH: 87
<212> TYPE: DNA
<213> ORGANISM: Corynebacterium glutamicum
<220> FEATURE:
<221> NAME/KEY: CDS
<222> LOCATION: (1)..(87)
<220> FEATURE:
<221> NAME/KEY: misc_feature
<222> LOCATION: (43)..(45)
<223> OTHER INFORMATION: n is a, c, g, or t

<400> SEQUENCE: 13 gat aaa acc tcc gct cgt ggt cag tac gct gcc ggt tgg cag nnn tct      48
Asp Lys Thr Ser Ala Arg Gly Gln Tyr Ala Ala Gly Trp Gln Xaa Ser
1               5                   10                  15 gag tta gtc aag gga ctt cgc gaa gaa gat ggc ttc aac                  87
Glu Leu Val Lys Gly Leu Arg Glu Glu Asp Gly Phe Asn
            20                  25

<210> SEQ ID NO 14
<211> LENGTH: 29
<212> TYPE: PRT
<213> ORGANISM: Corynebacterium glutamicum
<220> FEATURE:
<221> NAME/KEY: misc_feature
<222> LOCATION: (15)..(15)
<223> OTHER INFORMATION: The 'Xaa' at location 15 stands for Lys, Asn,
      Arg, Ser, Thr, Ile, Met, Glu, Asp, Gly, Ala, Val, Gln, His, Pro,
      Leu, Tyr, Trp, Cys, or Phe.

<400> SEQUENCE: 14

Asp Lys Thr Ser Ala Arg Gly Gln Tyr Ala Ala Gly Trp Gln Xaa Ser
1               5                   10                  15
Glu Leu Val Lys Gly Leu Arg Glu Glu Asp Gly Phe Asn
            20                  25

<210> SEQ ID NO 15
<211> LENGTH: 87
<212> TYPE: DNA
<213> ORGANISM: Corynebacterium glutamicum
<220> FEATURE:
<221> NAME/KEY: CDS
<222> LOCATION: (1)..(87)

<400> SEQUENCE: 15 gat aaa acc tcc gct cgt ggt cag tac gct gcc ggt tgg cag agc tct      48
Asp Lys Thr Ser Ala Arg Gly Gln Tyr Ala Ala Gly Trp Gln Ser Ser
1               5                   10                  15
```

```
gag tta gtc aag gga ctt cgc gaa gaa gat ggc ttc aac         87
Glu Leu Val Lys Gly Leu Arg Glu Glu Asp Gly Phe Asn
         20                  25
```

<210> SEQ ID NO 16
<211> LENGTH: 29
<212> TYPE: PRT
<213> ORGANISM: Corynebacterium glutamicum

<400> SEQUENCE: 16

```
Asp Lys Thr Ser Ala Arg Gly Gln Tyr Ala Ala Gly Trp Gln Ser Ser
1               5                   10                  15

Glu Leu Val Lys Gly Leu Arg Glu Glu Asp Gly Phe Asn
         20                  25
```

<210> SEQ ID NO 17
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer zwf-K1

<400> SEQUENCE: 17
aaggatcgtg acactaccat         20

<210> SEQ ID NO 18
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer zwf-K2

<400> SEQUENCE: 18
ggtggtatcc ggaagttcaa         20

<210> SEQ ID NO 19
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer zwf-L1

<400> SEQUENCE: 19
agaagctgac gctgtgttct         20

<210> SEQ ID NO 20
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer zwf-L2

<400> SEQUENCE: 20
cattggtgga ctcggtaact         20

<210> SEQ ID NO 21
<211> LENGTH: 1263
<212> TYPE: DNA
<213> ORGANISM: Corynebacterium glutamicum

```
<220> FEATURE:
<221> NAME/KEY: CDS
<222> LOCATION: (1)..(1263)
<223> OTHER INFORMATION: lysC wild-type gene

<400> SEQUENCE: 21 gtg gcc ctg gtc gta cag aaa tat ggc ggt tcc tcg ctt gag agt gcg        48
Met Ala Leu Val Val Gln Lys Tyr Gly Gly Ser Ser Leu Glu Ser Ala
1               5                   10                  15 gaa cgc att aga aac gtc gct gaa cgg atc gtt gcc acc aag aag gct        96
Glu Arg Ile Arg Asn Val Ala Glu Arg Ile Val Ala Thr Lys Lys Ala
                20                  25                  30 gga aat gat gtc gtg gtt gtc tgc tcc gca atg gga gac acc acg gat       144
Gly Asn Asp Val Val Val Val Cys Ser Ala Met Gly Asp Thr Thr Asp
            35                  40                  45 gaa ctt cta gaa ctt gca gcg gca gtg aat ccc gtt ccg cca gct cgt       192
Glu Leu Leu Glu Leu Ala Ala Ala Val Asn Pro Val Pro Pro Ala Arg
50                  55                  60 gaa atg gat atg ctc ctg act gct ggt gag cgt att tct aac gct ctc       240
Glu Met Asp Met Leu Leu Thr Ala Gly Glu Arg Ile Ser Asn Ala Leu
65                  70                  75                  80 gtc gcc atg gct att gag tcc ctt ggc gca gaa gcc caa tct ttc acg       288
Val Ala Met Ala Ile Glu Ser Leu Gly Ala Glu Ala Gln Ser Phe Thr
                85                  90                  95 ggc tct cag gct ggt gtc ctc acc acc gag cgc cac gga aac gca cgc       336
Gly Ser Gln Ala Gly Val Leu Thr Thr Glu Arg His Gly Asn Ala Arg
                100                 105                 110 att gtt gat gtc act cca ggt cgt gtg cgt gaa gca ctc gat gag ggc       384
Ile Val Asp Val Thr Pro Gly Arg Val Arg Glu Ala Leu Asp Glu Gly
            115                 120                 125 aag atc tgc att gtt gct ggt ttc cag ggt gtt aat aaa gaa acc cgc       432
Lys Ile Cys Ile Val Ala Gly Phe Gln Gly Val Asn Lys Glu Thr Arg
130                 135                 140 gat gtc acc acg ttg ggt cgt ggt ggt tct gac acc act gca gtt gcg       480
Asp Val Thr Thr Leu Gly Arg Gly Gly Ser Asp Thr Thr Ala Val Ala
145                 150                 155                 160 ttg gca gct gct ttg aac gct gat gtg tgt gag att tac tcg gac gtt       528
Leu Ala Ala Ala Leu Asn Ala Asp Val Cys Glu Ile Tyr Ser Asp Val
                165                 170                 175 gac ggt gtg tat acc gct gac ccg cgc atc gtt cct aat gca cag aag       576
Asp Gly Val Tyr Thr Ala Asp Pro Arg Ile Val Pro Asn Ala Gln Lys
                180                 185                 190 ctg gaa aag ctc agc ttc gaa gaa atg ctg gaa ctt gct gct gtt ggc       624
Leu Glu Lys Leu Ser Phe Glu Glu Met Leu Glu Leu Ala Ala Val Gly
                195                 200                 205 tcc aag att ttg gtg ctg cgc agt gtt gaa tac gct cgt gca ttc aat       672
Ser Lys Ile Leu Val Leu Arg Ser Val Glu Tyr Ala Arg Ala Phe Asn
        210                 215                 220 gtg cca ctt cgc gta cgc tcg tct tat agt aat gat ccc ggc act ttg       720
Val Pro Leu Arg Val Arg Ser Ser Tyr Ser Asn Asp Pro Gly Thr Leu
225                 230                 235                 240 att gcc ggc tct atg gag gat att cct gtg gaa gaa gca gtc ctt acc       768
Ile Ala Gly Ser Met Glu Asp Ile Pro Val Glu Glu Ala Val Leu Thr
                245                 250                 255 ggt gtc gca acc gac aag tcc gaa gcc aaa gta acc gtt ctg ggt att       816
Gly Val Ala Thr Asp Lys Ser Glu Ala Lys Val Thr Val Leu Gly Ile
                260                 265                 270 tcc gat aag cca ggc gag gct gcg aag gtt ttc cgt gcg ttg gct gat       864
Ser Asp Lys Pro Gly Glu Ala Ala Lys Val Phe Arg Ala Leu Ala Asp
        275                 280                 285
```

```
gca gaa atc aac att gac atg gtt ctg cag aac gtc tct tct gta gaa    912
Ala Glu Ile Asn Ile Asp Met Val Leu Gln Asn Val Ser Ser Val Glu
    290                 295                 300 gac ggc acc acc gac atc acc ttc acc tgc cct cgt tcc gac ggc cgc    960
Asp Gly Thr Thr Asp Ile Thr Phe Thr Cys Pro Arg Ser Asp Gly Arg
305                 310                 315                 320 cgc gcg atg gag atc ttg aag aag ctt cag gtt cag ggc aac tgg acc   1008
Arg Ala Met Glu Ile Leu Lys Lys Leu Gln Val Gln Gly Asn Trp Thr
                325                 330                 335 aat gtg ctt tac gac gac cag gtc ggc aaa gtc tcc ctc gtg ggt gct   1056
Asn Val Leu Tyr Asp Asp Gln Val Gly Lys Val Ser Leu Val Gly Ala
            340                 345                 350 ggc atg aag tct cac cca ggt gtt acc gca gag ttc atg gaa gct ctg   1104
Gly Met Lys Ser His Pro Gly Val Thr Ala Glu Phe Met Glu Ala Leu
        355                 360                 365 cgc gat gtc aac gtg aac atc gaa ttg att tcc acc tct gag att cgt   1152
Arg Asp Val Asn Val Asn Ile Glu Leu Ile Ser Thr Ser Glu Ile Arg
    370                 375                 380 att tcc gtg ctg atc cgt gaa gat gat ctg gat gct gct gca cgt gca   1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat   1248
Leu His Glu Gln Phe Gln Leu Gly Gly Glu Asp Glu Ala Val Val Tyr
                405                 410                 415 gca ggc acc gga cgc                                                1263
Ala Gly Thr Gly Arg
            420

<210> SEQ ID NO 22
<211> LENGTH: 421
<212> TYPE: PRT
<213> ORGANISM: Corynebacterium glutamicum

<400> SEQUENCE: 22

Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190
```

```
Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
        210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
                260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
        290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
                340                 345                 350

Gly Met Lys Ser His Pro Gly Val Thr Ala Glu Phe Met Glu Ala Leu
            355                 360                 365

Arg Asp Val Asn Val Asn Ile Glu Leu Ile Ser Thr Ser Glu Ile Arg
        370                 375                 380

Ile Ser Val Leu Ile Arg Glu Asp Asp Leu Asp Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 23
<211> LENGTH: 30
<212> TYPE: DNA
<213> ORGANISM: Artificial Sequence
<220> FEATURE:
<223> OTHER INFORMATION: Primer zwf-int1-bam

<400> SEQUENCE: 23
ctagggatcc acgtacgcga tgccgcaagt                                    30

<210> SEQ ID NO 24
<211> LENGTH: 30
<212> TYPE: DNA
<213> ORGANISM: Artificial Sequence
<220> FEATURE:
<223> OTHER INFORMATION: Primer zwf-int2-bam

<400> SEQUENCE: 24
ctagggatcc tcaggctgca cgcgaatcac                                    30
```

ALLELES OF THE ZWF GENE FROM CORYNEFORM BACTERIA

CROSS REFERENCE TO RELATED APPLICATIONS

The present application is a division of U.S. application Ser. No. 11/284,416, filed Nov. 22, 2005. U.S. Ser. No. 11/284,416 claims priority to German application 10 2005 013 676.1, filed on Mar. 24, 2005, and to U.S. provisional application 60/709,094, filed on Aug. 18, 2005. These previous applications are all incorporated by reference herein in their entirety.

The invention relates to mutants and alleles of the zwf gene of coryneform bacteria, which encode variants of the Zwf subunit of glucose 6-phosphate dehydrogenase (EC: 1.1.1.49), and to processes for preparing amino acids, in particular L-lysine and L-tryptophan, by using bacteria which harbor said alleles.

BACKGROUND OF THE INVENTION

Amino acids are applied in human medicine, in the pharmaceutical industry, in the food industry and especially in animal nutrition.

Amino acids are known to be prepared by fermentation of strains of coryneform bacteria, in particular *Corynebacterium glutamicum*. Due to the great importance, continuous efforts are made to improve the production processes. Said processes may be improved with respect to fermentation-related measures such as, for example, stirring and oxygen supply or the composition of the nutrient media, such as, for example, sugar concentration during the fermentation, or the working-up into product form, for example by means of ion exchange chromatography, or the intrinsic performance characteristics of the microorganism itself.

The performance characteristics of said microorganisms are improved by applying methods of mutagenesis, selection and mutant choice. This enables strains to be obtained which are resistant to antimetabolites or auxotrophic for metabolites which are of regulatory importance, and produce amino acids. A known antimetabolite is the lysine analog S-(2-aminoethyl)-L-cysteine (AEC).

For some years now, methods of recombinant DNA technology have likewise been employed in order to improve L-amino acid-producing *Corynebacterium* strains, by amplifying individual amino acid biosynthesis genes and studying the effect on amino acid production. A summary on a wide variety of aspects of the genetics, the metabolism and the biotechnology of *Corynebacterium glutamicum* can be found in Pühler (chief ed.) in Journal of Biotechnology 104 (1-3), 1-338, 2003.

The nucleotide sequence of the gene coding for glucose 6-phosphate dehydrogenase of *Corynebacterium glutamicum* is generally accessible, inter alia in the database of the National Center for Biotechnology Information (NCBI) of the National Library of Medicine (Bethesda, Md., USA). It can furthermore be found as sequence no. 243 (=AX065117) in the patent application WO 01/00844.

WO 01/70995 describes an improvement in the fermentative production of L-amino acids by coryneform bacteria due to amplification of the zwf gene.

WO 01/98472, WO 03/042389 and US 2003/0175911 A1 report novel mutations in the zwf gene.

Moritz et al. (European Journal of Biochemistry 267, 3442-3452 (2000)) report physiological and biochemical studies on glucose 6-phosphate dehydrogenase of *Corynebacterium glutamicum*. According to studies by Moritz et al., glucose 6-phosphate dehydrogenase consists of a Zwf subunit and an OpcA subunit.

The microbial biosynthesis of L-amino acids in coryneform bacteria is a complex system and linked on multiple levels to various other metabolic pathways in the cell. It is therefore not possible to predict which mutation alters the catalytic activity of glucose 6-phosphate dehydrogenase in such a way that production of L-amino acids is improved. It is therefore desirable to have available further variants of glucose 6-phosphate dehydrogenase.

For reasons of better clarity, SEQ ID NO:1 depicts the nucleotide sequence of the zwf gene coding for glucose 6-phosphate dehydrogenase and, respectively, of the zwf gene coding for the Zwf subunit of glucose 6-phosphate dehydrogenase from *Corynebacterium glutamicum* ("wild type gene"), according to the information of the NCBI database, and SEQ ID NO:2 and 4 depict the amino acid sequence derived therefrom of the encoded glucose 6-phosphate dehydrogenase. In addition, SEQ ID NO:3 indicates nucleotide sequences located upstream and downstream.

OBJECT OF THE INVENTION

The inventors have set themselves the object of providing novel measures for improving the production of amino acids, in particular L-lysine and L-tryptophan.

DESCRIPTION OF THE INVENTION

The invention relates to generated or isolated mutants of coryneform bacteria which preferably secrete amino acids, and which comprise a gene or allele encoding a polypeptide having glucose 6-phosphate dehydrogenase activity, wherein said polypeptide comprises an amino acid sequence in which any proteinogenic amino acid other than glycine is present in position 321 or a corresponding or comparable position of the amino acid sequence. Preference is given to the substitution of glycine with L-serine.

The polypeptide which is present in the mutants of the invention may likewise be referred to as Zwf polypeptide or Zwf subunit of glucose 6-phosphate dehydrogenase.

Among the coryneform bacteria, preference is given to the genus *Corynebacterium*. Particular preference is given to amino acid-secreting strains which are based on the following species:

*Corynebacterium efficiens*, for example the strain DSM44549,
*Corynebacterium glutamicum*, for example the strain ATCC13032,
*Corynebacterium thermoaminogenes* for example the strain FERM BP-1539, and
*Corynebacterium ammoniagenes*, for example the strain ATCC6871, very particular preference being given to the species *Corynebacterium glutamicum*.

Some representatives of the species *Corynebacterium glutamicum* are also known under different species names in the prior art. These include, for example:

*Corynebacterium acetoacidophilum* ATCC13870,
*Corynebacterium lilium* DSM20137,
*Corynebacterium melassecola* ATCC17965,
*Brevibacterium flavum* ATCC14067,
*Brevibacterium lactofermentum* ATCC13869, and
*Brevibacterium divaricatum* ATCC14020.

Examples of known representatives of amino acid-secreting strains of coryneform bacteria are the L-lysine-producing strains
- *Corynebacterium glutamicum* DM58-1/pDM6 (=DSM4697) described in EP 0 358 940,
- *Corynebacterium glutamicum* MH20-22B (=DSM16835) described in Menkel et al. (Applied and Environmental Microbiology 55(3), 684-688 (1989)),
- *Corynebacterium glutamicum* AHP-3 (=FermBP-7382) described in EP 1 108 790,
- *Corynebacterium thermoaminogenes* AJ12521 (=FERM BP-3304) described in U.S. Pat. No. 5,250,423, or the L-tryptophan-producing strains
- *Corynebacterium glutamicum* K76 (=FermBP-1847) described in U.S. Pat. No. 5,563,052,
- *Corynebacterium glutamicum* BPS13 (=FermBP-1777) described in U.S. Pat. No. 5,605,818, and
- *Corynebacterium glutamicum* FermBP-3055 described in U.S. Pat. No. 5,235,940.

Information on the taxonomic classification of strains of this group of bacteria can be found, inter alia, in Seiler (Journal of General Microbiology 129, 1433-1477 (1983)), Kampfer and Kroppenstedt (Canadian Journal of Microbiology 42, 989-1005 (1996)), Liebl et al. (International Journal of Systematic Bacteriology 41, 255-260 (1991)) and in U.S. Pat. No. 5,250,434.

Strains denoted "ATCC" may be obtained from the American Type Culture Collection (Manassas, Va., USA). Strains denoted "DSM" may be obtained from the Deutsche Sammlung von Mikroorganismen und Zellkulturen (DSMZ, Brunswick, Germany). Strains denoted "FERM" may be obtained from the National Institute of Advanced Industrial Science and Technology (AIST Tsukuba Central 6, 1-1-1 Higashi, Tsukuba Ibaraki, Japan). The *Corynebacterium thermoaminogenes* strains mentioned (FERM BP-1539, FERM BP-1540, FERM BP-1541 and FERM BP-1542) are described in U.S. Pat. No. 5,250,434.

The term proteinogenic amino acids means the amino acids occurring in natural proteins, i.e. in proteins of microorganisms, plants, animals and humans. These include in particular L-amino acids selected from the group consisting of L-aspartic acid, L-asparagine, L-threonine, L-serine, L-glutamic acid, L-glutamine, glycine, L-alanine, L-cysteine, L-valine, L-methionine, L-isoleucine, L-leucine, L-tyrosine, L-phenylalanine, L-histidine, L-lysine, L-tryptophan, L-proline and L-arginine. L-homoserine likewise belongs to the L-amino acids.

The mutants of the invention preferably secrete said proteinogenic amino acids, in particular L-lysine and L-tryptophan. The term amino acids also comprises their salts such as, for example, lysine monohydrochloride or lysine sulfate in the case of the amino acid L-lysine.

The invention further relates to mutants of coryneform bacteria, which comprise a zwf allele encoding a polypeptide having glucose 6-phosphate dehydrogenase enzyme activity, which polypeptide comprises the amino acid sequence of SEQ ID NO:2, with any proteinogenic amino acid other than glycine being present in position 321. Preference is given to replacing glycine with L-serine. In addition, the amino acid sequence of the polypeptide comprises, where appropriate, replacement of the amino acid L-serine in position 8 with a different proteinogenic amino acid, preferably L-threonine.

The invention furthermore relates to mutants of coryneform bacteria, which comprise a zwf allele encoding a polypeptide having glucose 6-phosphate dehydrogenase enzyme activity, which polypeptide comprises any proteinogenic amino acid other than glycine, preferably L-serine, in the position corresponding to position 321 of the amino acid sequence of SEQ ID NO:2, the gene comprising a nucleotide sequence identical to the nucleotide sequence of a polynucleotide which is obtainable by a polymerase chain reaction (PCR) using a primer pair whose nucleotide sequences comprise in each case at least 15 contiguous nucleotides selected from the nucleotide sequence between positions 1 and 307 of SEQ ID NO:3 or SEQ ID NO:11 and from the complementary nucleotide sequence between positions 2100 and 1850 of SEQ ID NO:3 or SEQ ID NO:11. Examples of suitable primer pairs of this kind are depicted in SEQ ID NO:17 and SEQ ID NO:18 and in SEQ ID NO:19 and SEQ ID NO:20. The preferred starting material (template DNA) is chromosomal DNA of coryneform bacteria which have been treated in particular with a mutagen. Particular preference is given to the chromosomal DNA of the genus *Corynebacterium* and very particular preference is given to that of the species *Corynebacterium glutamicum*.

The invention furthermore relates to mutants of coryneform bacteria, which comprise a zwf allele encoding a polypeptide having glucose 6-phosphate dehydrogenase enzyme activity, which polypeptide comprises an amino acid sequence having a length corresponding to 514 L-amino acids, with any proteinogenic amino acid other than glycine, preferably L-serine, being present in position 321. In addition, the amino acid L-serine in position 8 of the amino acid sequence of the polypeptide has, where appropriate, been replaced with a different proteinogenic amino acid, preferably L-threonine.

The invention furthermore relates to mutants of coryneform bacteria, which comprise a zwf allele encoding a polypeptide having glucose 6-phosphate dehydrogenase enzyme activity, which polypeptide comprises the amino acid sequence corresponding to positions 312 to 330 of SEQ ID NO:6 or 8 in positions 312 to 330 of the amino acid sequence. Preferably, the amino acid sequence of the encoded polypeptide comprises an amino acid sequence corresponding to positions 307 to 335 of SEQ ID NO:6 or 8 or to positions 292 to 350 of SEQ ID NO:6 or 8 or to positions 277 to 365 of SEQ ID NO:6 or 8 or to positions 262 to 380 of SEQ ID NO:6 or 8 or to positions 247 to 395 of SEQ ID NO:6 or 8 or to positions 232 to 410 of SEQ ID NO:6 or 8 or to positions 202 to 440 of SEQ ID NO:6 or 8 or to positions 172 to 470 of SEQ ID NO:6 or 8 or to positions 82 to 500 of SEQ ID NO:6 or 8 or to positions 2 to 512 of SEQ ID NO:6 or 8 or to positions 2 to 513 of SEQ ID NO:6 or 8 or to positions 2 to 514 of SEQ ID NO:6 or 8. Very particular preference is given to the length of the encoded polypeptide comprising 514 amino acids.

The invention furthermore relates to mutants of coryneform bacteria, which comprise a zwf allele encoding a polypeptide having glucose 6-phosphate dehydrogenase enzyme activity, which polypeptide comprises any amino acid other than glycine in position 321 or in the corresponding position of the amino acid sequence, preference being given to the substitution with L-serine, and whose amino acid sequence is moreover at least 90%, preferably at least 92% or at least 94% or at least 96%, and very particularly preferably at least 97% or at least 98% or at least 99%, identical to the amino acid sequence of SEQ ID NO:6. An example of an amino acid sequence having an identity of at least 99% to the amino acid sequence of SEQ ID NO:6 is depicted in SEQ ID NO:8 and 10. The polypeptide of this glucose 6-phosphate dehydrogenase possesses, apart from the amino acid substitution in position 321, the amino acid substitution of L-serine with L-threonine in position 8.

The invention furthermore relates to mutants of coryneform bacteria, which comprise a zwf allele encoding a polypeptide having glucose 6-phosphate dehydrogenase enzyme activity, which polypeptide comprises any amino acid other than glycine in position 321 or in the corresponding position of the amino acid sequence, with preference being given to the substitution with L-serine, and whose nucleotide sequence is moreover at least 90%, preferably at least 92% or at least 94% or at least 96%, and very particularly preferably at least 97% or at least 98% or at least 99%, identical to the nucleotide sequence of SEQ ID NO:5. An example of a nucleotide sequence of a zwf allele, which possesses at least 99% identity to the nucleotide sequence of SEQ ID NO:5, is depicted in SEQ ID NO:7. Apart from the nucleotide substitution of guanine with allanine in position 961 (see SEQ ID NO:5), the nucleotide sequence of this zwf allele has the nucleotide substitution of thymine with adenine in position 22 (see SEQ ID NO:7). A further example of a nucleotide sequence of a zwf allele, which has at least 99% identity to the nucleotide sequence of SEQ ID NO:5, is depicted in SEQ ID NO:9. The nucleotide sequence of this zwf allele has, apart from the nucleotide substitution of guanine with adenine in position 961 (see SEQ ID NO:5) and the nucleotide substitution of thymine with adenine in position 22 (see SEQ ID NO:7), the nucleotide substitutions of cytosine with thymine in position 138, of cytosine with thymine in position 279, of thymine with cytosine in position 738, of cytosine with thymine in position 777 and of guanine with adenine in position 906 (see SEQ ID NO:9).

Conservative amino acid substitutions are known to alter the enzyme activity only insignificantly. Accordingly, the zwf allele which is present in the mutants of the invention and which encodes a polypeptide having glucose 6-phosphate dehydrogenase enzyme activity may comprise one (1) or more conservative amino acid substitution(s), in addition to the amino acid sequence depicted in SEQ ID NO:6 and SEQ ID NO:8 and, respectively, SEQ ID NO:10. Preference is given to the polypeptide comprising no more than two (2), no more than three (3), no more than four (4) or no more than five (5), conservative amino acid substitutions.

In the case of the aromatic amino acids, the substitutions are said to be conservative when phenylalanine, tryptophan and tyrosine are substituted for one another. In the case of the hydrophobic amino acids, the substitutions are said to be conservative when leucine, isoleucine and valine are substituted for one another. In the case of the polar amino acids, the substitutions are said to be conservative when glutamine and asparagine are substituted for one another.

In the case of the basic amino acids, the substitutions are said to be conservative when arginine, lysine and histidine are substituted for one another. In the case of the acidic amino acids, the substitutions are said to be conservative when aspartic acid and glutamic acid are substituted for one another. In the case of the hydroxyl group-containing amino acids, the substitutions are said to be conservative when serine and threonine are substituted for one another.

An example of a conservative amino acid substitution is the substitution of serine with threonine in position 8 of SEQ ID NO:6, which results in the amino acid sequence according to SEQ ID NO:8 and SEQ ID NO:10, respectively.

During work on the present invention, comparison of the amino acid sequence using the Clustal program (Thompson et al., Nucleic Acids Research 22, 4637-4680 (1994)) revealed that the amino acid sequences of glucose 6-phosphate dehydrogenase of various bacteria such as, for example, *Escherichia coli*, *Bacillus subtilis*, *Mycobacterium tuberculosis*, *Mycobacterium bovis*, *Streptomyces coeliclor*, *Streptomyces avermitilis*, *Corynebacterium efficiens* and *Corynebacterium glutamicum*, comprise a sequence motif consisting of the sequence Val-Ile-Phe-Gly-Ali-Afa-Gly-Asp-Leu, a sequence motif consisting of the sequence Arg-Ile-Asp-His-Tyr-Leu-Gly-Lys, or a sequence motif consisting of the sequence Arg-Trp-Ala-Gly-Val-Pro-Phe-Tyr-Bra-Arg-Thr-Gly-Lys-Arg. The term "Ali" represents the amino acids Ala or Val, the term "Afa" represents the amino acids Lys or Thr, and the term "Bra" represents the amino acids Ile or Leu.

Accordingly, preference is given to those mutants of coryneform bacteria, which comprise a zwf allele encoding a polypeptide having glucose 6-phosphate dehydrogenase enzyme activity, which polypeptide comprises at least one amino acid sequence selected from the group consisting of Val-Ile-Phe-Gly-Ali-Afa-Gly-Asp-Leu, Arg-Ile-Asp-His-Tyr-Leu-Gly-Lys and Arg-Trp-Ala-Gly-Val-Pro-Phe-Tyr-Bra-Arg-Thr-Gly-Lys-Arg and which comprises any amino acid other than lysine, preferably L-serine, in position 321 or in the corresponding or comparable position of the amino acid sequence. In addition, the amino acid sequence comprises, where appropriate, an amino acid substitution of L-serine with a different proteinogenic amino acid, preferably L-threonine, in position 8 according to SEQ ID NO:2.

The amino acid sequence motif Val-Ile-Phe-Gly-Val-Thr-Gly Asp-Leu is present, for example, in SEQ ID NO:6, 8 or 10 from positions 32 to 40. The amino acid sequence motif Arg-Ile-Asp-His-Tyr-Leu-Gly-Lys is present, for example, in SEQ ID NO:6, 8 and, respectively, 10 from position 203 to 210. The amino acid sequence motif Arg-Trp-Ala-Gly-Val-Pro-Phe-Tyr-Leu-Arg-Thr-Gly-Lys-Arg is present, for example, in SEQ ID NO:6, 8 or 10 from positions 354 to 367.

Finally, the invention relates to mutants of coryneform bacteria, which comprise a zwf allele encoding a polypeptide having glucose 6-phosphate dehydrogenase enzyme activity, which polypeptide comprises the amino acid sequence of SEQ ID NO:6 or SEQ ID NO:8 and, respectively, SEQ ID NO:10.

Enzymes intrinsic to the host, called aminopeptidases, are known to remove the terminal methionine during protein synthesis.

The term "a position corresponding to position 321 of the amino acid sequence" or "a position comparable to position 321 of the amino acid sequence" means the fact that insertion or deletion of a codon coding for an amino acid in the N-terminal region (based on position 321 of SEQ ID NO:6, 8 or 10) of the encoded polypeptide formally increases, in the case of an insertion, or decreases, in the case of a deletion, the indicated position and indicated length, in each case by one unit. For example, deletion of the AAC codon coding for the amino acid L-asparagine in position 4 of SEQ ID NO:6, 8 or 10 moves the L-serine from position 321 to position 320. The indicated length would then be: 513 amino acids. In the same way, insertion or deletion of a codon coding for an amino acid in the C-terminal region (based on position 321) of the encoded polypeptide formally increases, in the case of an insertion, or decreases, in the case of a deletion, the indicated length by one unit. Such comparable positions can readily be identified by comparing the amino acid sequences in the form of an alignment, for example with the aid of the Clustal program.

Insertions and deletions of this kind essentially do not affect the enzymic activity. "Essentially do not affect" means that the enzymic activity of the variants mentioned differs from the activity of the polypeptide having the amino acid sequence of SEQ ID NO:6 or 8 and, respectively, 10 by no more than 10%, no more than 7.5%, no more than 5%, no more than 2.5% or no more than 1%.

Accordingly, the invention also relates to zwf alleles encoding polypeptide variants of SEQ ID NO:6 or 8 and, respectively, 10, which variants comprise one or more insertion(s) or deletion(s). The polypeptide preferably comprises no more than 5, no more than 4, no more than 3 or no more than 2 amino acid insertions or deletions.

The sequence motifs Val-Ile-Phe-Gly-Ali-Afa-Gly-Asp-Leu, and Arg-Ile-Asp-His-Tyr-Leu-Gly-Lys and Arg-Trp-Ala-Gly-Val-Pro-Phe-Tyr-Bra-Arg-Thr-Gly-Lys-Arg are preferably not disrupted by such insertions/deletions.

The mutants of the invention may be prepared by classical in-vivo mutagenesis methods with cell populations of coryneform bacteria by using mutagenic substances such as, for example, N-methyl-N'-nitro-N-nitrosoguanidine (MNNG), ethyl methanesulfonate (EMS), 5-bromouracil, or ultraviolet light. Mutagenesis methods are described, for example, in Manual of Methods for General Bacteriology (Gerhard et al. (Eds.), American Society for Microbiology, Washington, D.C., USA, 1981) or in Tosaka et al. (Agricultural and Biological Chemistry 42(4), 745-752 (1978)) or in Konicek et al. (Folia Microbiologica 33, 337-343 (1988)). Typical mutageneses using MNNG comprise concentrations of from 50 to 500 mg/l or else higher concentrations of up to a maximum of 1 g/l, an incubation time of from 1 to 30 minutes at a pH of from 5.5 to 7.5. Under these conditions, the number of viable cells is reduced by a proportion of from approx. 50% to 90% or approx. 50% to 99% or approx. 50% to 99.9% or more.

Mutants or cells are removed from the mutagenized cell population and propagated. Preference is given to investigating, in a further step, their ability to secrete amino acids, preferably L-lysine or L-tryptophan, in a batch culture using a suitable nutrient medium. Suitable nutrient media and assay conditions are described, inter alia, in U.S. Pat. No. 6,221,636, in U.S. Pat. No. 5,840,551, in U.S. Pat. No. 5,770,409, in U.S. Pat. No. 5,605,818, in U.S. Pat. No. 5,275,940 and in U.S. Pat. No. 4,224,409. Using suitable robots, as described, for example, in Zimmermann et al. (VDI Berichte No. 1841, VDI-Verlag, Düsseldorf, Germany 2004, 439-443) or Zimmermann (Chemie Ingenenieur Technik 77 (4), 426-428 (2005)), it is possible to study a large number of mutants in a short time. In this way, mutants are identified which, compared to the parent strain or non-mutagenized starting strain, secrete an increased amount of amino acids into the nutrient medium or the cell interior. These include, for example, those mutants whose amino acid secretion has increased by at least 0.5%.

Subsequently, DNA of the mutants is provided or isolated from the latter and the corresponding polynucleotide is synthesized with the aid of the polymerase chain reaction using primer pairs which allow amplification of the zwf gene or of the zwf allele of the invention or of the mutation of the invention in position 321. Preference is given to isolating the DNA from those mutants which secrete an increased amount of amino acids.

To this end, it is possible to select any primer pairs from the nucleotide sequence located upstream and downstream of the mutation of the invention and from the nucleotide sequence complementary thereto. A primer of a primer pair here preferably comprises at least 15, at least 18, at least 20, at least 21 or at least 24, contiguous nucleotides selected from the nucleotide sequence between positions 1 and 1267 of SEQ ID NO:3 or SEQ ID NO:11. The corresponding second primer of a primer pair comprises at least 15, at least 18, at least 20, at least 21 or at least 24, contiguous nucleotides selected from the complementary nucleotide sequence of positions 2100 and 1271 of SEQ ID NO:3 or SEQ ID NO:11. If it is desired to amplify the coding region, then the primer pair is preferably selected from the nucleotide sequence between positions 1 and 307 of SEQ ID NO:3 or SEQ ID NO:11 and from the complementary nucleotide sequence between positions 2100 and 1850 of SEQ ID NO:3 or SEQ ID NO:11. If it is desired to amplify part of the coding region, as indicated, for example, in SEQ ID NO:14 and 15, then the primer pair is preferably selected from the nucleotide sequence between positions 309 and 1267 of SEQ ID NO:3 or SEQ ID NO:11 and from the complementary nucleotide sequence between positions 1848 and 1271 of SEQ ID NO:3 or SEQ ID NO:11. Examples of suitable primer pairs are the zwf-K1 and zwf-K2 primer pair depicted under SEQ ID NO:17 and SEQ ID NO:18 or the zwf-L1 and zwf-L2 primer pair depicted under SEQ ID NO:19 and SEQ ID NO:20. In addition, the primer may be provided with recognition sites for restriction enzymes, with a biotin group or further accessories as described in the prior art. The total length of the primer is usually no more than 30, 40, 50 or 60 nucleotides.

Usually, thermostable DNA polymerases are employed in the preparation of polynucleotides by amplification of selected sequences such as the zwf allele of the invention from initially introduced DNA, for example chromosomal DNA (template DNA), via amplification by means of PCR. Examples of DNA polymerases of this kind are Taq polymerase of *Thermus aquaticus,* which is sold, inter alia, by Qiagen (Hilden, Germany), Vent polymerase of *Thermococcus litoralis,* sold, inter alia, by New England Biolabs (Frankfurt, Germany), or Pfu polymerase of *Pyrococcus furiosus,* sold, inter alia, by Stratagene (La Jolla, USA). Preference is given to polymerases having proof-reading activity. Proof-reading activity means that these polymerases are capable of recognizing wrongly incorporated nucleotides and rectifying the error by renewed polymerization (Lottspeich and Zorbas, Bioanalytik, Spektrum Akademischer Verlag, Heidelberg, Germany (1998)). Examples of polymerases having proof-reading activity are Vent polymerase and Pfu polymerase.

The conditions in the reaction mixture are set according to the information provided by the manufacturer. The polymerases are usually supplied by the manufacturer together with the customary buffer which usually has concentrations of 10-100 mM Tris/HCl and 6-55 mM KCl at pH 7.5-9.3. Magnesium chloride is added in a concentration of 0.5-10 mM, if not present in the buffer supplied by the manufacturer. Furthermore, deoxynucleoside triphosphates are added in a concentration of 0.1-16.6 mM to the reaction mixture. The primers, in a final concentration of 0.1-3 µM, and template DNA, in the optimal case from $10^2$ to $10^5$ copies, are initially introduced into the reaction mixture. $10^6$ to $10^7$ copies may also be used. An amount of 2-5 units of the appropriate polymerase is added to the reaction mixture. A typical reaction mixture has a volume of 20-100 µl.

Further additives which may be added to the reaction are bovine serum albumin, Tween-20, gelatin, glycerol, formamide or DMSO (Dieffenbach and Dveksler, PCR Primer—A Laboratory Manual, Cold Spring Harbor Laboratory Press, USA 1995).

A typical PCR profile consists of three different, successively repeated temperature stages. Initially, the reaction is started by increasing the temperature to 92° C.-98° C. for 4 to 10 minutes in order to denature the initially introduced DNA. This is followed repeatedly by first a step of denaturing the initially introduced DNA at approximately 92-98° C. for 10-60 seconds, then a step of 10-60 seconds of binding the primers to the initially introduced DNA at a particular temperature dependent on said primers (annealing temperature), which from experience is from 50° C. to 60° C. and can be calculated for each primer pair individually. Detailed information on this can be found by the skilled worker in Rychlik et al. (Nucleic Acids Research 18 (21): 6409-6412). Subsequently, a synthesis step of extending the initially introduced primers (extension) at the activity optimum of the polymerase, indicated in each case and usually in the range from 73° C. to 67° C., preferably 72° C. to 68° C., depending on the polymerase. The duration of this extension step depends on the performance of the polymerase and on the length of the PCR product to be amplified. In a typical PCR, this step lasts 0.5-8 minutes, preferably 2-4 minutes. These three steps are repeated 30 to 35 times, where appropriate up to 50 times. A final "extension" step of 4-10 minutes ends the reaction. The polynucleotides prepared in this manner are also referred to as amplicons; the term nucleic acid fragment is likewise common.

Further instructions and information regarding PCR can be found by the skilled worker for example in the manual "PCR-Strategies" (Innis, Felfand and Sninsky, Academic Press, Inc., 1995), in the manual by Diefenbach and Dveksler "PCR Primer—a laboratory manual" (Cold Spring Harbor Laboratory Press, 1995), in the manual by Gait "Oligonucleotide synthesis: A Practical Approach" (IRL Press, Oxford, UK, 1984) and in Newton and Graham "PCR" (Spektrum Akademischer Verlag, Heidelberg, Germany, 1994).

The nucleotide sequence is subsequently determined, for example by the chain termination method of Sanger et al. (Proceedings of the National Academies of Sciences, U.S.A., 74, 5463-5467 (1977)) with the modifications indicated by Zimmermann et al. (Nucleic Acids Research 18, 1067 pp (1990)), and the polypeptide encoded by said nucleotide sequence is analyzed, in particular with respect to the amino acid sequence. For this purpose, the nucleotide sequence is entered into a program for translating DNA sequence into an amino acid sequence. Examples of suitable programs are the program "Patentin" which is available from patent offices, for example the US Patent and Trademark Office (USPTO), or "Translate Tool" which is available on the ExPASy Proteomics Server on the World Wide Web (Gasteiger et al., Nucleic Acids Research 31, 3784-3788 (2003)).

In this way, mutants are identified whose zwf alleles encode polypeptides having glucose 6-phosphate dehydrogenase enzyme activity, which polypeptides comprise any proteinogenic amino acid other than glycine in position 321 of the amino acid sequence or in the corresponding or comparable position. Preference is given to the substitution with L-serine. In addition, the amino acid sequence comprises, where appropriate, an amino acid substitution of L-serine with a different proteinogenic amino acid, preferably L-threonine, in position 8 or in the corresponding or comparable position.

Accordingly, the invention relates to a mutant of a coryneform bacterium, which is obtainable by the following steps:
a) treating a coryneform bacterium capable of secreting amino acids with a mutagenic agent,
b) isolating and propagating the mutant generated in a),
c) preferably determining the ability of said mutant to secrete in a medium or to accumulate in the cell interior at least 0.5% more amino acid than the coryneform bacterium employed in a),
d) providing nucleic acid of the mutant obtained in b),
e) preparing a nucleic acid molecule/amplicon/nucleic acid fragment, using the polymerase chain reaction, of the nucleic acid from d) and of a primer pair consisting of a first primer comprising at least 15 contiguous nucleotides selected from the nucleotide sequence between positions 1 and 1267 of SEQ ID NO:3 or SEQ ID NO:11 and a second primer comprising at least 15 contiguous nucleotides selected from the complementary nucleotide sequence between positions 2100 and 1271 of SEQ ID NO:3 or 11,
f) determining the nucleotide sequence of the nucleic acid molecule obtained in e) and determining the encoded amino acid sequence,
g) comparing, where appropriate, the amino acid sequence determined in f) with SEQ ID NO:6, 8 or 10, and
h) identifying a mutant comprising a polynucleotide which encodes a polypeptide comprising any proteinogenic amino acid other than glycine, preferably L-serine, in position 321 or a comparable position, and which, where appropriate, comprises any proteinogenic amino acid other than L-serine, preferably L-threonine, in position 8 or a comparable position.

The mutants generated in this way typically comprise one (1) copy of the zwf allele described.

SEQ ID NO:5, 7 and 9 depict, by way of example, the coding regions of zwf alleles of mutants of the invention. The coding region of the wild type gene is depicted as SEQ ID NO:1. SEQ ID NO:1 comprises the nucleobase guanine in position 961, the nucleobase guanine in position 962 and the nucleobase cytosine in position 963. SEQ ID NO:1 comprises the GGC codon, coding for the amino acid glycine, in positions 961 to 963. SEQ ID NO:5 comprises the nucleobase adenine in position 961. This guanine-adenine transition results in the AGC codon, coding for the amino acid L-serine, in positions 961 to 963.

SEQ ID NO:1 comprises the nucleobase thymine in position 22, the nucleobase cytosine in position 23 and the nucleobase cytosine in position 24. Accordingly, SEQ ID NO:1 comprises the TCC codon, coding for the amino acid serine, in positions 22 to 24. SEQ ID NO:7 comprises the nucleobase adenine in position 22. This thymine-adenine transversion results in the AGC codon, coding for the amino acid L-serine, in positions 22 to 24.

In addition, the nucleotide sequences depicted in SEQ ID NO:5 and 7 may comprise further base substitutions which have resulted from the mutagenesis treatment but which do not manifest themselves in an altered amino acid sequence. Such mutations are referred to in the art also as silent or neutral mutations. These silent mutations may likewise already be present in the coryneform bacterium used for mutagenesis treatment. Examples of such silent mutations are the cytosine-thymine transition in position 138, the cytosine-thymine transition in position 279, the thymine-cytosine transition in position 738, the cytosine-thymine transition in position 777 and the guanine-adenine transition in position 906, as depicted in SEQ ID NO:9.

The coryneform bacteria used for the mutagenesis preferably already have the ability to secrete the desired amino acid into the surrounding nutrient medium or fermentation broth or to accumulate it in the cell interior.

L-Lysine-producing coryneform bacteria typically possess a feedback-resistant or desensibilized aspartate kinase. Feedback-resistant aspartate kinases mean aspartate kinases which, compared to the wild type, have a lower sensitivity to the inhibition by mixtures of lysine and threonine or mixtures of AEC (aminoethylcysteine) and threonine or lysine alone or AEC alone. The genes or alleles encoding these desensibilized aspartate kinases are also referred to as $lysC^{FBR}$ alleles. The prior art (Table 1) describes numerous $lysC^{FBR}$ alleles encoding aspartate kinase variants which have amino acid substitutions in comparison with the wild type protein. SEQ ID NO:21 depicts the coding region of the wild type lysC gene of *Corynebacterium glutamicum* according to accession number AX756575 of the NCBI database, and SEQ ID NO:22 depicts the protein encoded by said gene.

TABLE 1 lysC$^{FBR}$ alleles encoding feedback-resistant aspartate kinases

| Name of allele | Further information | Reference | Accession number |
|---|---|---|---|
| lysC$^{FBR}$ E05108 | | JP 1993184366-A (sequence 1) | E05108 |
| lysC$^{FBR}$ E06825 | lysC A279T | JP 1994062866-A (sequence 1) | E06825 |
| lysC$^{FBR}$ E06826 | lysC A279T | JP 1994062866-A (sequence 2) | E06826 |
| lysC$^{FBR}$ E06827 | | JP 1994062866-A (sequence 3) | E06827 |
| lysC$^{FBR}$ E08177 | | JP 1994261766-A (sequence 1) | E08177 |
| lysC$^{FBR}$ E08178 | lysC A279T | JP 1994261766-A (sequence 2) | E08178 |
| lysC$^{FBR}$ E08179 | lysC A279V | JP 1994261766-A (sequence 3) | E08179 |
| lysC$^{FBR}$ E08180 | lysC S301F | JP 1994261766-A (sequence 4) | E08180 |
| lysC$^{FBR}$ E08181 | lysC T308I | JP 1994261766-A (sequence 5) | E08181 |
| lysC$^{FBR}$ E08182 | | JP 1994261766-A (sequence 6) | E08182 |
| lysC$^{FBR}$ E12770 | | JP 1997070291-A (sequence 13) | E12770 |
| lysC$^{FBR}$ E14514 | | JP 1997322774-A (sequence 9) | E14514 |
| lysC$^{FBR}$ E16352 | | JP 1998165180-A (sequence 3) | E16352 |
| lysC$^{FBR}$ E16745 | | JP 1998215883-A (sequence 3) | E16745 |
| lysC$^{FBR}$ E16746 | | JP 1998215883-A (sequence 4) | E16746 |
| lysC$^{FBR}$ I74588 | | U.S. Pat. No. 5,688,671-A (sequence 1) | I74588 |
| lysC$^{FBR}$ I74589 | lysC A279T | U.S. Pat. No. 5,688,671-A (sequence 2) | I74589 |
| lysC$^{FBR}$ I74590 | | U.S. Pat. No. 5,688,671-A (sequence 7) | I74590 |
| lysC$^{FBR}$ I74591 | lysC A279T | U.S. Pat. No. 5,688,671-A (sequence 8) | I74591 |
| lysC$^{FBR}$ I74592 | | U.S. Pat. No. 5,688,671-A (sequence 9) | I74592 |
| lysC$^{FBR}$ I74593 | lysC A279T | U.S. Pat. No. 5,688,671-A (sequence 10) | I74593 |
| lysC$^{FBR}$ I74594 | | U.S. Pat. No. 5,688,671-A (sequence 11) | I74594 |
| lysC$^{FBR}$ I74595 | lysC A279T | U.S. Pat. No. 5,688,671-A (sequence 12) | I74595 |
| lysC$^{FBR}$ I74596 | | U.S. Pat. No. 5,688,671-A (sequence 13) | I74596 |
| lysC$^{FBR}$ I74597 | lysC A279T | U.S. Pat. No. 5,688,671-A (sequence 14) | I74597 |
| lysC$^{FBR}$ X57226 | lysC S301Y | EP0387527 Kalinowski et al., Molecular and General Genetics 224:317-324 (1990) | X57226 |
| lysC$^{FBR}$ L16848 | lysC G345D | Follettie and Sinskey NCBI Nucleotide Database (1990) | L16848 |
| lysC$^{FBR}$ L27125 | lysC R320G lysC G345D | Jetten et al., Applied Microbiology Biotechnology 43:76-82 (1995) | L27125 |
| lysC$^{FBR}$ | lysC T311I | WO0063388 (sequence 17) | |
| lysC$^{FBR}$ | lysC S301F | U.S. Pat. No. 3,732,144 | |
| lysC$^{FBR}$ | lysC S381F | EP0435132 | |
| lysC$^{FBR}$ | lysC S317A | U.S. Pat. No. 5,688,671 (sequence 1) | |
| lysC$^{FBR}$ | lysC T380I | WO 01/49854 | |

L-Lysine-secreting coryneforme bacteria typically possess one or more of the amino acid substitutions listed in Table 1.

Preference is given to the following lysC$^{FBR}$ alleles: lysC A279T (substitution of alanine in position 279 of the encoded aspartate kinase protein according to SEQ ID NO:22 with threonine), lysC A279V (substitution of alanine in position 279 of the encoded aspartate kinase protein according to SEQ ID NO:22 with valine), lysC S301F (substitution of serine in position 301 of the encoded aspartate kinase protein according to SEQ ID NO:22 with phenylalanine), lysC T308I (substitution of threonine in position 308 of the encoded aspartate kinase protein according to SEQ ID NO:22 with isoleucine), lysC S301Y (substitution of serine in position 308 of the encoded aspartate kinase protein according to SEQ ID NO:22 with tyrosine), lysC G345D (substitution of glycine in position 345 of the encoded aspartate kinase protein according to SEQ ID NO:22 with asparaginic acid), lysC R320G (substitution of arginine in position 320 of the encoded aspartate kinase protein according to SEQ ID NO:22 with glycine), lysC T311I (substitution of threonine in position 311 of the encoded aspartate kinase protein according to SEQ ID NO:22 with isoleucine), lysC S381F (substitution of serine in position 381 of the encoded aspartate kinase protein according to SEQ ID NO:22 with phenylalanine) and lysC S317A (substitution of serine in position 317 of the encoded aspartate kinase protein according to SEQ ID NO:22 with alanine).

Particular preference is given to the lysC$^{FBR}$ allele lysC T311I (substitution of threonine in position 311 of the encoded aspartate kinase protein according to SEQ ID NO:22 with isoleucine) and a lysC$^{FBR}$ allele comprising at least one substitution selected from the group consisting of A279T (substitution of alanine in position 279 of the encoded aspartate kinase proteins according to SEQ ID NO:22 with threonine) and S317A (substitution of serine in position 317 of the encoded aspartate kinase protein according to SEQ ID NO:22 with alanine). The lysC$^{FBR}$ allele lysC T311I is present in the strain DM1797 deposited with the DSMZ. DM1797 is a mutant of *Corynebacterium glutamicum* ATCC13032.

Starting from strain DM1797, a mutant referred to as DM1816, which harbors a zwf allele encoding a polypeptide in which L-serine is present in position 321 of the amino acid sequence, was isolated in the manner described above. The nucleotide sequence of the coding region of the zwf allele of the DM1816 mutant is depicted as SEQ ID NO:9 and the amino acid sequence of the encoded polypeptide is depicted as SEQ ID NO:10 and 12, respectively. The DM1816 mutant additionally comprises nucleotide substitutions in the nucleotide sequence between positions 1 and 307 of SEQ ID NO:3. These nucleotide substitutions are depicted in SEQ ID NO:11. SEQ ID NO:11 comprises guanine instead of adenine in position 208, adenine instead of guanine in position 235, cytosine instead of thymine in position 245, guanine. instead of adenine in position 257 and guanine instead of adenine in position 299. SEQ ID NO:11 furthermore comprises adenine instead of thymine in position 329, thymine instead of cytosine in position 445, thymine instead of cytosine in position 586, cytosine instead of thymine in position 1045, thymine instead of cytosine in position 1084, adenine instead of guanine in position 1213 and adenine instead of guanine in position 1268.

In addition it is possible to use L-lysine-secreting coryneform bacteria which have an attenuated homoserine dehydrogenase or homoserine kinase or which possess other properties as known from the prior art. L-Tryptophan-producing coryneform bacteria typically possess a feedback-resistant or desensibilized anthranilate synthase. The term feedback-resistant anthranilate synthase means anthranilate synthases which, compared to the wild type, have a lower sensitivity to inhibition (5% to 10%, 10% to 15% or 10% to 20%) by tryptophan or 5-fluorotryptophan (Matsui et al., Journal of Bacteriology 169 (11): 5330-5332 (1987)) or similar analogs. The genes or alleles encoding these desensibilized anthranilate synthases are also referred to as trpE$^{FBR}$ alleles. Examples of mutants or alleles of this kind are described, for example, in U.S. Pat. No. 6,180,373 and EP0338474.

The mutants obtained show increased secretion or production of the desired amino acid in a fermentation process, in comparison with the starting strain or parent strain employed.

The invention likewise relates to an isolated polynucleotide encoding a polypeptide having glucose 6-phosphate dehydrogenase enzyme activity, which polypeptide comprises any proteinogenic amino acid other than glycine in position 321 or in a corresponding or comparable position of the amino acid sequence, with preference being given to the substitution with L-serine.

The polynucleotide of the invention may be isolated from a mutant of the invention.

It is furthermore possible to use in-vitro methods for the mutagenesis of the zwf gene. The use of in-vitro methods involves subjecting isolated polynucleotides which comprise a zwf gene of a coryneform bacterium, preferably the *Corynebacterium glutamicum* wild type gene described in the prior art, to a mutagenic treatment.

The isolated polynucleotides may be, for example, isolated total DNA or chromosomal DNA or else amplicons of the zwf gene, which have been prepared with the aid of the polymerase chain reaction (PCR). Such amplicons are also referred to as PCR products. Instructions for the amplification of DNA sequences with the aid of the polymerase chain reaction can be found by the skilled worker, inter alia, in the manual by Gait: Oligonucleotide Synthesis: A Practical Approach (IRL Press, Oxford, UK, 1984) and Newton and Graham: PCR (Spektrum Akademischer Verlag, Heidelberg, Germany, 1994). It is likewise possible to incorporate the zwf gene to be mutagenized first into a vector, for example into a bacteriophage or into a plasmid. Suitable methods of in-vitro mutagenesis are, inter alia, the treatment with hydroxylamine according to Miller (Miller, J. H.: A Short Course in Bacterial Genetics. A Laboratory Manual and Handbook for *Escherichia coli* and Related Bacteria, Cold Spring Harbor Laboratory Press, Cold Spring Harbor, 1992), the use of mutagenic oligonucleotides (T. A. Brown: Gentechnologie für Einsteiger [Genetic engineering for beginners], Spektrum Akademischer Verlag, Heidelberg, 1993 and R. M. Horton: PCR-Mediated Recombination and Mutagenesis, Molecular Biotechnology 3, 93-99 (1995)) and the use of a polymerase chain reaction using a DNA polymerase with a high error rate. An example of such a DNA polymerase is the Mutazyme DNA Polymerase (GeneMorph PCR Mutagenesis Kit, No.600550) from Stratagene (La Jolla, Calif., USA).

Further instructions and reviews on the generation of mutations in vivo or in vitro can be found in the prior art and in known textbooks of genetics and molecular biology, such as, for example, the textbook by Knippers ("Molekulare Genetik", 6th edition, Georg Thieme Verlag, Stuttgart, Germany, 1995), that by Winnacker ("Gene and Klone", VCH Verlagsgesellschaft, Weinheim, Germany, 1990) or that by Hagemann ("Allgemeine Genetik", Gustav Fischer Verlag, Stuttgart, 1986).

The invention furthermore relates to an isolated polynucleotide encoding a polypeptide having glucose 6-phosphate dehydrogenase enzyme activity, which polypeptide comprises the amino acid sequence of SEQ ID NO:2, with any proteinogenic amino acid other than glycine being present in position 321 of said amino acid sequence. Preference is given to the substitution with L-serine. In addition, the amino acid sequence of the polypeptide comprises, where appropriate, an amino acid substitution of L-serine with a different amino acid, preferably L-threonine, in position 8.

The invention furthermore relates to an isolated polynucleotide encoding a polypeptide having glucose 6-phosphate dehydrogenase enzyme activity, which polypeptide comprises an amino acid sequence having a length of 514 amino acids, with any proteinogenic L-amino acid other than glycine, preferably L-serine, being present in position 321.

The invention furthermore relates to an isolated polynucleotide encoding a polypeptide having glucose 6-phosphate dehydrogenase enzyme activity, which polypeptide comprises, from position 312 to 330 of the amino acid sequence, the amino acid sequence corresponding to positions 312 to 330 of SEQ ID NO:6 or 8. The amino acid sequence of the encoded polypeptide preferably comprises an amino acid sequence corresponding to positions 307 to 335 of SEQ ID NO:6 or 8 or to positions 292 to 350 of SEQ ID NO:6 or 8 or to positions 277 to 365 of SEQ ID NO:6 or 8 or to positions 262 to 380 of SEQ ID NO:6 or 8 or to positions 247 to 395 of SEQ ID NO:6 or 8 or to positions 232 to 410 of SEQ ID NO:6 or 8 or to positions 202 to 440 of SEQ ID NO:6 or 8 or to positions 172 to 470 of SEQ ID NO:6 or 8 or to positions 82 to 500 of SEQ ID NO:6 or 8 or to positions 2 to 512 of SEQ ID NO:6 or 8 or to positions 2 to 513 of SEQ ID NO:6 or 8 or to positions 2 to 514 of SEQ ID NO:6 or 8. The length of the encoded polypeptide comprises very particularly preferably 514 amino acids.

The invention furthermore relates to an isolated polynucleotide encoding a polypeptide having glucose 6-phosphate dehydrogenase enzyme activity, which polypeptide comprises any proteinogenic amino acid other than glycine, preferably L-serine, in position 321 of the amino acid sequence or in a corresponding or comparable position, and comprising a nucleotide sequence identical to the nucleotide sequence of a polynucleotide which is obtainable by a polymerase chain reaction (PCR) using the primer pair whose nucleotide sequences comprise in each case at least 15 contiguous nucleotides selected from the nucleotide sequence between positions 1 and 307 of SEQ ID NO:3 or SEQ ID NO:11 and from the complementary nucleotide sequence between positions 2100 and 1850 of SEQ ID NO:3 or SEQ ID NO:11. Examples of suitable primer pairs of this kind are depicted in SEQ ID NO:17 and SEQ ID NO:18 and in SEQ ID NO:19 and SEQ ID NO:20. The preferred starting material (template DNA) is chromosomal DNA of coryneform bacteria, in particular of those which have been treated with a mutagen. Particular preference is given to the chromosomal DNA of the genus *Corynebacterium,* and very particular preference is given to that of the species *Corynebacterium glutamicum.*

The invention furthermore relates to an isolated polynucleotide which hybridizes with the nucleotide sequence complementary to SEQ ID NO:5, 7 or 9 under stringent conditions and which encodes a polypeptide having glucose 6-phosphate dehydrogenase enzyme activity, which polypeptide comprises any proteinogenic amino acid other than glycine, preferably L-serine, in position 321 of the amino acid sequence or in a corresponding or comparable position and, where appropriate, any proteinogenic amino acid other than L-serine, preferably L-threonine, in a position corresponding to position 8.

Instructions regarding the hybridization of nucleic acids or polynucleotides can be found by the skilled worker, inter alia, in the manual "The DIG System User's Guide for Filter Hybridization" from Boehringer Mannheim GmbH (Mannheim, Germany, 1993) and in Liebl et al. (International Journal of Systematic Bacteriology 41: 255-260 (1991)). The hybridization is carried out under stringent conditions, i.e. only hybrids in which the probe, i.e. a polynucleotide comprising the nucleotide sequence complementary to SEQ ID NO:5, 7 or 9, and the target sequence, i.e. the polynucleotides treated or identified with the probe, are at least 90% identical, are formed. The stringency of the hybridization, including that of the washing steps, is known to be influenced or determined by varying the buffer composition, the temperature and the salt concentration. The hybridization reaction is generally carried out at relatively low stringency compared to the washing steps (Hybaid Hybridisation Guide, Hybaid Limited, Teddington, UK, 1996).

For example, a buffer corresponding to 5×SSC buffer at a temperature of approx. 50° C.-68° C. may be used for the hybridization reaction. In this case, probes may also hybridize with polynucleotides which are less than 90% identical to the nucleotide sequence of the probe employed. Such hybrids are less stable and are removed by washing under stringent conditions. This may be achieved, for example, by lowering the salt concentration to 2×SSC and, where appropriate, subsequently to 0.5×SSC (The DIG System User's Guide for Filter Hybridisation, Boehringer Mannheim, Mannheim, Germany, 1995), with the temperature being set to approx. 50° C.-68° C., approx. 52° C.-68° C., approx. 54° C.-68° C., approx. 56° C.-68° C., approx. 58° C.-68° C., approx. 60° C.-68° C., approx. 62° C.-68° C., approx. 64° C.-68° C., approx. 66° C.-68° C. Temperature ranges of approx. 64° C.-68° C. or approx. 66° C.-68° C. are preferred. It is possible, where appropriate, to lower the salt concentration down to a concentration corresponding to 0.2×SSC or 0.1×SSC. The SSC buffer comprises, where appropriate, sodium dodecyl sulfate (SDS) in a concentration of 0.1%. By gradually increasing the hybridization temperature in steps of approx. 1-2° C. from 50° C. to 68° C., it is possible to isolate polynucleotide fragments which have at least 90% or at least 91%, preferably at least 92% or at least 93% or at least 94% or at least 95% or at least 96%, and very particularly preferably at least 97% or at least 98% or at least 99%, identity to the sequence or complementary sequence of the probe employed and which encode a polypeptide which has glucose 6-phosphate dehydrogenase enzyme activity and comprises the amino acid substitution of the invention. The nucleotide sequence of the polynucleotide obtained in this way is determined by known methods. Further instructions regarding hybridization are commercially available in the form of "kits" (e.g. DIG Easy Hyb from Roche Diagnostics GmbH, Mannheim, Germany, Catalog No. 1603558). The nucleotide sequences thus obtained encode polypeptides having glucose 6-phosphate dehydrogenase enzyme activity, which polypeptides are at least 90%, preferably at least 92% or at least 94% or at least 96%, and very particularly preferably at least 97% or at least 98% or at least 99%, identical to the amino acid sequence of SEQ ID NO:6 or SEQ ID NO:8 and which comprise the amino acid substitution of the invention.

The invention furthermore relates to an isolated polynucleotide encoding a polypeptide having glucose 6-phosphate dehydrogenase enzyme activity, which polypeptide comprises any amino acid other than glycine in position 321 or in a corresponding or comparable position of the amino acid sequence, the substitution with L-serine being preferred, and which comprises an amino acid sequence which moreover is at least 90%, preferably at least 92% or at least 94% or at least 96%, and very particularly preferably at least 97% or at least 98% or at least 99%, identical to the amino acid sequence of SEQ ID NO:6. One example of a polypeptide having glucose 6-phosphate dehydrogenase enzyme activity, which polypeptide comprises an amino acid sequence at least 99% identical to that of SEQ ID NO:6, is depicted in SEQ ID NO:8 and SEQ ID NO:10.

The invention furthermore relates to an isolated polynucleotide encoding a polypeptide having glucose 6-phosphate dehydrogenase enzyme activity, which polypeptide comprises any amino acid other than glycine in position 321 or in a corresponding or comparable position of the amino acid sequence, the substitution with L-serine being preferred, and comprising a nucleotide sequence which moreover is at least 90%, preferably at least 92% or at least 94% or at least 96%, and very particularly preferably at least 97% or at least 98% or at least 99%, identical to the nucleotide sequence of SEQ ID NO:5. An example of a polynucleotide which encodes a polypeptide of the invention having glucose 6-phosphate dehydrogenase enzyme activity and which has a nucleotide sequence at least 99% identical to that of SEQ ID NO:5 is depicted in SEQ ID NO:7. The nucleotide sequence of this zwf allele has, in addition to the nucleotide substitution of guanine with adenine in position 961 (see SEQ ID NO:5), the nucleotide substitution of thymine with adenine in position 22 (see SEQ ID NO:7). Another example of a nucleotide sequence of a zwf allele, which has at least 99% identity to the nucleotide sequence of SEQ ID NO:5, is depicted in SEQ ID NO:9. The nucleotide sequence of this zwf allele has, in addition to the nucleotide substitution of guanine with adenine in position 961 (see SEQ ID NO:5) and the nucleotide substitution of thymine with adenine in position 22 (see SEQ ID NO:7), the nucleotide substitutions of cytosine with thymine in position 138, of cytosine with thymine in position 279, of thymine with cytosine in position 738, of cytosine with thymine in position 777, and of guanine with adenine in position 906 (see SEQ ID NO:9).

In addition, preference is given to those isolated polynucleotides encoding a polypeptide having glucose 6-phosphate dehydrogenase enzyme activity, which polypeptide comprises any amino acid other than glycine, preferably L-serine, in position 321 of the amino acid sequence or in a corresponding or comparable position, and comprising at least one sequence motif or an amino acid sequence selected from the group consisting of Val-Ile-Phe-Gly-Ali-Afa-Gly-Asp-Leu, Arg-Ile-Asp-His-Tyr-Leu-Gly-Lys, and Arg-Trp-Ala-Gly-Val-Pro-Phe-Tyr-Bra-Arg-Thr-Gly-Lys-Arg.

The term "Ali" represents the amino acids Ala or Val, the term "Afa" represents the amino acids Lys or Thr, and the term "Bra" represents the amino acids Ile or Leu.

The invention furthermore relates to an isolated polynucleotide encoding a polypeptide having glucose 6-phosphate dehydrogenase enzyme activity, which polypeptide comprises the amino acid sequence of SEQ ID NO:6 or 8 and, respectively, 10. The encoded polypeptide comprises, where appropriate, one (1) or more conservative amino acid substitution(s). Preferably, the polypeptide comprises no more than two (2), no more than three (3), no more than four (4) or no more than five (5), conservative amino acid substitutions.

The invention furthermore relates to an isolated polynucleotide encoding a polypeptide having glucose 6-phosphate dehydrogenase enzyme activity, which polypeptide comprises the amino acid sequence of SEQ ID NO:6 or 8 and, respectively, 10, including an extension at the N- or C-terminus by at least one (1) amino acid. This extension has no more than 50, 40, 30, 20, 10, 5, 3 or 2 amino acids or amino acid residues.

Finally, the invention also relates to zwf alleles encoding polypeptide variants of SEQ ID NO:6, 8 or 10, which comprise one or more insertions or deletions. These preferably comprise no more than 5, no more than 4, no more than 3 or no more than 2 insertions or deletions of amino acids. Preferably, the sequence motifs Val-Ile-Phe-Gly-Ali-Afa-Gly-Asp-Leu and/or Arg-Ile-Asp-His-Tyr-Leu-Gly-Lys and/or Arg-Trp-Ala-Gly-Val-Pro-Phe-Tyr-Bra-Arg-Thr-Gly-Lys-Arg are not disrupted by such insertions/deletions.

The invention furthermore relates to an isolated polynucleotide comprising the nucleotide sequence according to SEQ ID NO:5, 7, 9 or 11.

The invention furthermore relates to an isolated polynucleotide comprising the nucleotide sequence between positions 1 and 307 of SEQ ID NO:11, preferably the nucleotide sequence between positions 198 and 304 of SEQ ID NO:11, and very particularly preferably the nucleotide sequence between positions 208 and 299 of SEQ ID NO:11.

Finally, the invention relates to an isolated polynucleotide comprising the zwf allele of the DM1816 mutant.

Moreover, the invention relates to an isolated polynucleotide comprising part of the coding region of a zwf allele of the invention, said isolated polynucleotide comprising in any case that part of the coding region which comprises the amino acid substitution in position 321 of the amino acid sequence of the encoded polypeptide.

More specifically, a nucleic acid molecule or DNA fragment is comprised which encodes at least one amino acid sequence corresponding to positions 307 to 335 of SEQ ID NO:2 or which encodes at least one amino acid sequence corresponding to positions 292 to 350 of SEQ ID NO:2 or which encodes at least one amino acid sequence corresponding to positions 277 to 365 of SEQ ID NO:2 or which encodes at least one amino acid sequence corresponding to positions 262 to 380 of SEQ ID NO:2 or which encodes at least one amino acid sequence corresponding to positions 247 to 395 of SEQ ID NO:2 or which encodes at least one amino acid sequence corresponding to positions 232 to 410 of SEQ ID NO:2 or which encodes at least one amino acid sequence corresponding to positions 202 to 440 of SEQ ID NO:2, or which encodes at least one amino acid sequence corresponding to positions 172 to 470 of SEQ ID NO:2 or which encodes at least one amino acid sequence corresponding to positions 82 to 500 of SEQ ID NO:2, or which encodes at least one amino acid sequence corresponding to positions 2 to 512 of SEQ ID NO:2, or which encodes at least one amino acid sequence corresponding to positions 2 to 513 of SEQ ID NO:2, or which encodes at least one amino acid sequence corresponding to positions 2 to 514 of SEQ ID NO:2, or which includes a corresponding reading frame, with any proteinogenic amino acid other than glycine, preferably L-serine, being present in the position corresponding to 321 of SEQ ID NO:2 and, where appropriate, any proteinogenic amino acid except L-serine, preferably L-threonine, being present in the position corresponding to 8.

An example of a reading frame of the invention, comprising a polynucleotide encoding at least the amino acid sequence of positions 307 to 335 corresponding to SEQ ID NO:2, with any proteinogenic amino acid (Xaa) other than glycine being present in the position corresponding to 321 of the amino acid sequence, is listed below:

```
gat aaa acc tcc gct cgt ggt cag tac gct gcc ggt
Asp Lys Thr Ser Ala Arg Gly Gln Tyr Ala Ala Gly
307         310                     315 tgg cag nnn tct gag tta gtc aag gga ctt cgc gaa
Trp Gln Xaa Ser Glu Leu Val Lys Gly Leu Arg Glu
        320                 325                 330 gaa gat ggc ttc aac
Glu Asp Gly Phe Asn
                335
```

It is likewise depicted as SEQ ID NO:13. The amino acid sequence encoded by this reading frame is depicted as SEQ ID NO:14. Position 15 in SEQ ID NO:14 corresponds to position 321 of SEQ ID NO:6, 8, 10 or 12.

Preference is given to nucleic acid molecules encoding at least one amino acid sequence corresponding to positions 307 to 335 of SEQ ID NO:6 or 8 and, respectively, 10, or at least corresponding to position 292 to 350 of SEQ ID NO:6 or 8 and, respectively, 10, or at least corresponding to positions 277 to 365 of SEQ ID NO:6 or 8 and, respectively, 10, or at least corresponding to positions 262 to 380 of SEQ ID NO:6 or 8 and, respectively, 10, or at least corresponding to positions 247 to 395 of SEQ ID NO:6 or 8 and, respectively, 10, or at least corresponding to positions 232 to 410 of SEQ ID NO:6 or 8 and, respectively, 10, or at least corresponding to positions 202 to 440 of SEQ ID NO:6 or 8 and, respectively, 10, or at least corresponding to positions 172 to 470 of SEQ ID NO:6 or 8 and, respectively, 10, or at least corresponding to positions 82 to 500 of SEQ ID NO:6 or 8 and, respectively, 10, or at least corresponding to positions 2 to 512 of SEQ ID NO:6 or 8 and, respectively, 10, or at least corresponding to positions 2 to 513 of SEQ ID NO:6 or 8 and, respectively 10, or at least corresponding to positions 2 to 514 of SEQ ID NO:6 or 8 and, respectively, 10.

An example of a reading frame of the invention, comprising a polynucleotide encoding at least the amino acid sequence corresponding to positions 307 to 335 of SEQ ID NO:6, is listed below:

```
gat aaa acc tcc gct cgt ggt cag tac gct gcc ggt
Asp Lys Thr Ser Ala Arg Gly Gln Tyr Ala Ala Gly
307         310                     315 tgg cag agc tct gag tta gtc aag gga ctt cgc gaa
Trp Gln Ser Ser Glu Leu Val Lys Gly Leu Arg Glu
        320                 325                 330 gaa gat ggc ttc aac
Glu Asp Gly Phe Asn
                335
```

The reading frame is likewise depicted as SEQ ID NO:15. SEQ ID NO:16 depicts the amino acid sequence encoded by said reading frame. Position 15 in SEQ ID NO:16 corresponds to position 321 of SEQ ID NO:6, 8, 10 or 12.

Very particular preference is given to nucleic acid molecules comprising at least one nucleotide sequence corresponding to positions 919 to 1005 of SEQ ID NO:5, 7 or 9, or at least one nucleotide sequence corresponding to positions 874 to 1050 of SEQ ID NO:5, 7 or 9, or at least one nucleotide sequence corresponding to positions 829 to 1095 of SEQ ID NO:5, 7 or 9, or at least one nucleotide sequence corresponding to positions 784 to 1140 of SEQ ID NO:5, 7 or 9, or at least one nucleotide sequence corresponding to positions 739 to 1185 of SEQ ID NO:5, 7 or 9, or at least one nucleotide sequence corresponding to positions 694 to 1230 of SEQ ID NO:5, 7 or 9, or at least one nucleotide sequence corresponding to positions 604 to 1320 of SEQ ID NO:5, 7 or 9, or at least one nucleotide sequence corresponding to positions 514 to 1410 of SEQ ID NO:5, 7 or 9, or at least one nucleotide sequence corresponding to positions 244 to 1500 of SEQ ID NO:5, 7 or 9, or at least one nucleotide sequence corresponding to positions 4 to 1536 of SEQ ID NO:5, 7 or 9, or at least one nucleotide sequence corresponding to positions 4 to 1539 of SEQ ID NO:5, 7 or 9, or at least one nucleotide sequence corresponding to positions 4 to 1542 of SEQ ID NO:5, 7 or 9.

In addition, the reading frames of the invention, as shown by way of example in SEQ ID NO:13 and 15 as nucleotide sequence and in SEQ ID NO:14 and SEQ ID NO:16 in the form of the encoded amino acid sequence, may comprise one or more mutations resulting in one or more conservative amino acid substitutions. The mutations preferably result in no more than 4%, no more than 2% or no more than 1%, conservative amino acid substitutions. The reading frames of the invention may furthermore comprise one more silent mutations. The reading frames of the invention comprise preferably no more than 4%, and particularly preferably no more than 2% to no more than 1%, silent mutations.

The isolated polynucleotides of the invention may be used in order to produce recombinant strains of microorganisms, which release amino acids into the surrounding medium or accumulate them in the cell interior in an improved manner, compared to the starting or parent strain.

A widespread method of incorporating mutations into genes of coryneform bacteria is that of allele substitution which is also referred to as gene replacement. This process involves transferring a DNA fragment comprising the mutation of interest into the desired strain of a coryneform bacterium and incorporating said mutation into the chromosome of the desired strain by at least two recombination events or cross-over events or replacing the sequence of a gene in the strain in question with the mutated sequence.

Schwarzer and Pühler (Bio/Technology 9, 84-87 (1991) used this method in order to incorporate a lysA allele carrying a deletion and a lysA allele carrying an insertion into the *C. glutamicum* chromosome, instead of the wild type gene. Schafer et al. (Gene 145, 69-73 (1994)) employed said method in order to incorporate a deletion into the *C. glutamicum* hom-thrB operon. Nakagawa et al. (EP 1108790) and Ohnishi et al. (Applied Microbiology and Biotechnology 58(2), 217-223 (2002)) employed said method in order to incorporate various mutations, starting from the isolated alleles, into the *C. glutamicum* chromosome. In this way, Nakagawa et al. succeeded in incorporating a mutation referred to as Val59Ala into the homoserine dehydrogenase gene (hom), a mutation referred to as Thr311Ile into the aspartate kinase gene (lysC and ask, respectively), a mutation referred to as Pro458Ser into the pyruvate carboxylase gene (pyc) and a mutation referred to as Ala213Thr into the glucose 6-phosphate dehydrogenase gene (zwf) of *C. glutamicum* strains.

A process of the invention may use a polynucleotide of the invention, which comprises the entire coding region, as depicted, for example, in SEQ ID NO:5, 7 or 9, or which comprises part of the coding region, such as, for example, the nucleotide sequence encoding at least the amino acid sequence corresponding to positions 307 to 335 of SEQ ID NO:6, 8 or 10, and depicted as SEQ ID NO:13 and 15. The part of the coding region corresponding to SEQ ID NO:13 and 15 is $\geq 87$ nucleobases in length. Preference is given to those parts of the coding region whose length is $\geq 267$ nucleobases, such as, for example, nucleic acid molecules encoding at least one amino acid sequence corresponding to positions 277 to 365 of SEQ ID NO:6, 8 or 10. Very particular preference is given to those parts of the coding region whose length is $\geq 357$ nucleobases, such as, for example, nucleic acid molecules coding for at least one amino acid sequence corresponding to positions 262 to 380 of SEQ ID NO:6, 8 or 10.

In said method, the DNA fragment comprising the mutation of interest is typically present in a vector, in particular a plasmid which preferably is replicated only to a limited extent, if at all, by the strain to be provided with the mutation. The auxiliary or intermediate host used, in which the vector can be replicated, is usually a bacterium of the genus *Escherichia*, preferably of the species *Escherichia coli*.

Examples of plasmid vectors of this kind are the pK*mob and pK*mobsacB vectors described by Schafer et al. (Gene 145, 69-73 (1994)), such as, for example, pK18mobsacB, and the vectors described in WO 02/070685 and WO 03/014362. These are replicative in *Escherichia coli* but not in coryneform bacteria. Particularly suitable are vectors comprising a gene with a conditionally negative-dominant action, such as, for example, the sacB gene (levansucrase gene) of *Bacillus*, for example, or the galK gene (galactose kinase gene) of *Escherichia coli*, for example. (A gene with conditionally negative-dominant action means a gene which, under certain conditions, is disadvantageous, for example toxic, to the host but which has, under different conditions, no adverse effects on the host carrying the gene.) Said vectors make possible the selection for recombination events in which the vector is eliminated from the chromosome. Nakamura et al. (U.S. Pat. No. 6,303,383) furthermore described a temperature-sensitive plasmid for coryneform bacteria, which can replicate only at temperatures below 31° C.

The vector is subsequently transferred to the coryneform bacterium by way of conjugation, for example by the method of Schafer (Journal of Bacteriology 172, 1663-1666 (1990)), or transformation, for example by the method of Dunican and Shivnan (Bio/Technology 7, 1067-1070 (1989)) or the method of Thierbach et al. (Applied Microbiology and Biotechnology 29, 356-362 (1988)). The DNA may also be transferred, where appropriate, by particle bombardment.

Incorporation of the mutation is achieved after homologous recombination by means of a first cross-over event causing integration and of a suitable second cross-over event causing excision in the target gene or in the target sequence, resulting in a recombinant bacterium.

The strains obtained may be identified and characterized by using, inter alia, the methods of Southern blotting hybridization, polymerase chain reaction, sequence determination, the method of fluorescence resonance energy transfer (FRET) (Lay et al. Clinical Chemistry 43, 2262-2267 (1997)) or methods of enzymology.

Accordingly, the invention further relates to a process for preparing a coryneform bacterium, which comprises a) transferring a polynucleotide of the invention to a coryneform bacterium, b) replacing the glucose 6-phosphate dehydrogenase gene which encodes an amino acid sequence with glycine in position 321 or in a comparable position of said amino acid sequence and which is present in the chromosome of said coryneform bacterium with the polynucleotide of a), which encodes an amino acid sequence having a different L-amino acid, preferably L-serine, in position 321 or in a comparable position of said amino acid sequence and, where appropriate, any proteinogenic amino acid other than L-serine, preferably the amino acid L-threonine, in position 8 or in a comparable position, and c) propagating the coryneform bacterium obtained by steps a) and b).

In this way a recombinant coryneform bacterium is obtained which comprises one (1) zwf allele of the invention, instead of the wild type zwf gene.

Another process of the invention for preparing a microorganism comprises a) transferring a polynucleotide of the invention, which encodes a polypeptide having glucose 6-phosphate dehydrogenase enzyme activity, to a microrganism, b) replicating said polynucleotide in said microorganism, and c) propagating the microorganism obtained by steps a) and b).

In this way a recombinant microorganism is obtained, which comprises at least one (1) copy or several copies of a polynucleotide of the invention, which polynucleotide encodes a glucose 6-phosphate dehydrogenase comprising any proteinogenic amino acid other than glycine in position 321 or a comparable position of the amino acid sequence of the encoded polypeptide, the substitution with L-serine being preferred. The polypeptide comprises, where appropriate, any proteinogenic amino acid other than L-serine, preferably the amino acid L-threonine, in position 8 or a comparable position.

Accordingly, the invention further relates to hosts or host cells, preferably microorganisms, particularly preferably coryneform bacteria and bacteria of the genus *Escherichia*, which comprise the polynucleotides of the invention. The invention likewise relates to microorganisms prepared by using the isolated polynucleotides. Such microorganisms or bacteria are also referred to as recombinant microorganisms or recombinant bacteria. In the same way, the invention relates to vectors comprising the polynucleotides of the invention. Finally, the invention likewise relates to hosts harboring said vectors.

The isolated polynucleotides of the invention may likewise be used for achieving overexpression of the polypeptides encoded by them.

Overexpression generally means an increase in the intracellular concentration or activity of a ribonucleic acid, a protein or an enzyme. In the case of the present invention, zwf alleles or polynucleotides which encode glucose 6-phosphate dehydrogenases comprising any proteinogenic amino acid other than glycine in position 321 of the amino acid sequence of the encoded polypeptide, with the substitution with L-serine being preferred, are overexpressed. The encoded protein moreover comprises, where appropriate, a substitution of L-serine with a different proteinogenic amino acid, preferably L-threonine, in position 8 of the amino acid sequence. Enzymes endogenous to the host—"aminopeptidases"—are known to be able to cleave N-terminal amino acids, in particular the N-terminal methionine, off the polypeptide produced. Said increase in the concentration or activity of a gene product can be achieved, for example, by increasing the copy number of the corresponding polynucleotides by at least one copy.

A widespread method of increasing the copy number comprises incorporating the appropriate gene or allele into a vector, preferably a plasmid, which is replicated by a coryneform bacterium. Examples of suitable plasmid vectors are pZ1 (Menkel et al., Applied and Environmental Microbiology (1989) 64: 549-554) or the pSELF vectors described by Tauch et al. (Journal of Biotechnology 99, 79-91 (2002)). A review article on plasmids in *Corynebacterium glutamicum* can be found in Tauch et al. (Journal of Biotechnology 104, 27-40 (2003))

Another common method of achieving overexpression is the process of chromosomal gene amplification. This method involves inserting at least one additional copy of the gene or allele of interest into the chromosome of a coryneform bacterium.

In one embodiment, as described, for example, for the hom-thrB operon in Reinscheid et al. (Applied and Environmental Microbiology 60, 126-132 (1994)), a plasmid which is non-replicative in *C. glutamicum* and which comprises the gene of interest is transferred to a coryneform bacterium. After homologous recombination by means of a cross-over event, the resulting strain comprises at least two copies of the gene or allele in question.

In another embodiment described in WO 03/040373 and US-2003-0219881-A1, one or more copies of the gene of interest are inserted at a desired side of the *C. glutamicum* chromosome by means of at least two recombination events. In this way, for example, a copy of a lysC allele encoding a L-lysine-insensitive aspartate kinase was incorporated into the *C. glutamicum* gluB gene.

In a further embodiment described in WO 03/014330 and US-2004-0043458-A1, at least one further copy, preferably in tandem arrangement to the gene or allele already present, of the gene of interest is incorporated by means of at least two recombinantion events at the natural locus. In this way it was possible, for example, to achieve a tandem duplication of a lysC$^{FBR}$ allele at the natural lysC gene locus.

Another method of achieving overexpression comprises linking the appropriate gene or allele functionally (operably linked) to a promoter or an expression cassette.

Examples of suitable promotors for *Corynebacterium glutamicum* are described in the review article by Patek et al. (Journal of Biotechnology 104(1-3), 311-323 (2003)). It is furthermore possible to use the well-known promoters T3, T7, SP6, M13, lac, tac and trc described by Amann et al. (Gene 69(2), 301-315 (1988)) and Amann and Brosius (Gene 40(2-3), 183-190 (1985)). Such a promotor may be inserted, for example, upstream of the zwf allele, typically at a distance of approximately 1-500 or 1-307 nucleotides from the start codon, of a recombinant coryneform bacterium, which allele comprises, instead of the amino acid glycine naturally present in position 321, a different proteinogenic amino acid. A promotor of this kind may naturally likewise be inserted upstream of the zwf allele of a mutant of the invention. It is furthermore possible to link an isolated polynucleotide of the invention, which encodes a variant of the invention of glucose 6-phosphate dehydrogenase, to a promotor and to incorporate the expression unit obtained into an extrachromosomally replicating plasmid or into the chromosome of a coryneform bacterium.

In addition, it is possible to mutate the promotor and regulatory regions or the ribosomal binding site which is located upstream of the structural gene. An example of a mutated promotor region of the zwf gene or zwf allele is the nucleotide sequence comprising positions 208 to 299 of SEQ ID NO:11. Measures of extending the mRNA lifetime likewise improve expression. Preventing the degradation of the enzyme protein furthermore likewise enhances enzyme activity. Alternatively, the gene or allele in question may furthermore be overexpressed by altering the media composition and the culturing process.

The overexpression measures increase the activity or concentration of the protein in question usually by at least 10%, 25%, 50%, 75%, 100%, 150%, 200%, 300%, 400% or 500%, up to no more than 1000% or 2000%, based on the activity or concentration of the protein in the starting microorganism or parent strain. A starting microorganism or parent strain means a microorganism which is subjected to the measures of the invention.

A method of determining the enzymic activity of glucose 6-phosphate dehydrogenase is described in Moritz et al. (European Journal of Biochemistry 267, 3442-3452 (2000)).

The concentration of the protein may be determined via 1- and 2-dimensional protein gel fractionation and subsequent optical identification of the protein concentration in the gel, using appropriate evaluation software. A common method of preparing the protein gels in the case of coryneform bacteria and of identifying the proteins is the procedure described by Hermann et al. (Electrophoresis, 22:1712-23 (2001)). The protein concentration may likewise be determined by Western blot hybridization using an antibody specific for the protein to be detected (Sambrook et al., Molecular cloning: a laboratory manual. $2^{nd}$ Ed. Cold Spring Harbor Laboratory Press, Cold Spring Harbor, N.Y., 1989) and subsequent optical evaluation using appropriate concentration determination software (Lohaus and Meyer (1998) Biospektrum 5:32-39; Lottspeich, Angewandte Chemie 321: 2630-2647 (1999)).

Accordingly, the invention relates to processes for overexpressing the glucose 6-phosphate dehydrogenases of the invention. A process of the invention for overexpression comprises, inter alia, increasing the copy number of a polynucleotide of the invention, which polynucleotide encodes a glucose 6-phosphate-dehydrogenase variant comprising any proteinogenic amino acid other than glycine in position 321 or the corresponding position of the encoded amino acid sequence and comprising, where appropriate, any proteinogenic amino acid other than L-serine in position 8 or the corresponding position, by at least one (1) or several copies. Another process of the invention comprises functionally linking a promotor to the polynucleotide.

The invention furthermore relates to microorganisms having an increased concentration or activity of the glucose 6-phosphate dehydrogenase variants of the invention in their cell interior.

It may be additionally advantageous for improved production of L-amino acids to overexpress in the mutants or recombinant strains of the invention one or more enzymes of the particular biosynthetic pathway, of glycolysis, of anaplerotics, of the citrate cycle, of the pentose phosphate cycle, of the amino acid export and, where appropriate, regulatory proteins. Preference is usually given to the use of endogenous genes.

"Endogenous genes" or "endogenous nucleotide sequences" means the genes or the nucleotide sequences or alleles present in the population of a species.

Thus it is possible to overexpress for the preparation of L-lysine one or more of the genes selected from the group consisting of a dapA gene encoding a dihydrodipicolinate synthase, such as, for example, the *Corynebacterium glutamicum* wild-type dapA gene described in EP 0 197 335, a zwf gene encoding a glucose 6-phosphate dehydrogenase, such as, for example, the *Corynebacterium glutamicum* wild-type zwf gene described in JP-A-09224661 and EP-A-1108790, the *Corynebacterium glutamicum* zwf alleles described in US-2003-0175911-A1, which encode a protein in which, for example, the L-alanine in position 243 of the amino acid sequence has been replaced with L-threonine or in which the L-aspartic acid in position 245 has been replaced with L-serine, a pyc gene encoding a pyruvate carboxylase, such as, for example, the *Corynebacterium glutamicum* wild-type pyc gene described in DE-A-198 31 609 and EP 1108790, the *Corynebacterium glutamicum* pyc allele described in EP 1 108 790, which encodes a protein in which L-proline in position 458 of the amino acid sequence has been replaced by L-serine, the *Corynebacterium glutamicum* pyc alleles described in WO 02/31158, which encode proteins which, according to claim 1, carry one or more of the amino acid substitutions selected from the group consisting of L-glutamic acid in position 153 replaced with L-aspartic acid, L-alanine in position 182 replaced with L-serine, L-alanine in position 206 replaced with L-serine, L-histidine in position 227 replaced with L-arginine, L-alanine in position 452 replaced with glycine and L-aspartic acid in position 1120 replaced with L-glutamic acid (FIG. 2A in WO 02/31158 specifies two different start positions for the pyruvate carboxylase, which positions differ by a length corresponding to 17 amino acids. Accordingly, position 153 in accordance with claim 1 in WO 02/31158 corresponds to a position 170 in FIG. 2A in WO 02/31158, while position 182 in accordance with claim 1 corresponds to position 199 in FIG. 2A, position 206 in accordance with claim 1 corresponds to position 223 in FIG. 2A, position 227 in accordance with claim 1 corresponds to position 244 in FIG. 2A, position 452 in accordance with claim 1 corresponds to position 469 in FIG. 2A, position 1120 in accordance with claim 1 corresponds to position 1137 in FIG. 2B. FIG. 2A in WO 02/31158 furthermore indicates an amino acid substitution of A (alanine) with G (glycine) in position 472. Position 472 of the protein having the N terminal sequence MTA corresponds to position 455 of the protein having the N-terminal sequence MST according to FIG. 2A. FIG. 2B in WO 02/31158 furthermore indicates an amino acid substitution of D (aspartic acid) with E (glutamic acid) in position 1133 of the protein having the N-terminus MTA.), a lysC gene encoding an aspartate kinase, such as, for example, that of *Corynebacterium glutamicum* wild-type lysC gene described as SEQ ID NO:281 in EP-A-1108790 (see also accession numbers AX120085 and 120365) and that of *Corynebacterium glutamicum* wild-type lysC gene, described as SEQ ID NO:25 in WO 01/00843 (see accession number AX063743), a $lysC^{FBR}$ allele, in particular according to Table 1, which encodes a feedback-resistant aspartate kinase variant, a lysE gene encoding a lysine export protein, such as, for example, the *Corynebacterium glutamicum* wild-type lysE gene described in DE-A-195 48 222, the *Corynebacterium glutamicum* wild-type zwa1 gene encoding the Zwa1 protein (U.S. Pat. No. 6,632,644).

In addition to using the alleles of the invention of the zwf gene, it may also be advantageous, for the purpose of producing L-lysine, to simultaneously attenuate or eliminate one or more of the endogenous genes selected from the group consisting of a pgi gene encoding glucose 6-phosphate isomerase, such as, for example, the *Corynebacterium glutamicum* pgi gene described in U.S. Pat. No. 6,586,214 and U.S. Pat. No. 6,465,238, a hom gene encoding homoserine dehydrogenase, such as, for example, the *Corynebacterium glutamicum* hom gene described in EP-A-0131171, a thrB gene encoding homoserine kinase, such as, for example, the *Corynebacterium glutamicum* thrB gene described by Peoples et al. (Molecular Microbiology 2 (1988): 63-72)), and a pfkB gene encoding phosphofructokinase, such as, for example, the *Corynebacterium glutamicum* pfkB gene described in WO 01/00844 (sequence no. 57).

In this connection, the term "attenuation" describes the reduction or elimination of the intracellular activity of one or more enzymes (proteins) which are encoded by the corresponding DNA in a microorganism which is achieved, for example, by using a weak promoter or using a gene or allele which encodes a corresponding enzyme having low activity, or inactivating the corresponding gene or enzyme (protein), and, where appropriate, combining these measures.

As a result of using the measures for achieving attenuation, the activity or concentration of the corresponding protein is generally lowered to from 0 to 75%, from 0 to 50%, from 0 to 25%, from 0 to 10%, or from 0 to 5%, of the activity or concentration of the wild-type protein or of the activity or concentration of the protein in the starting microorganism.

Mutations which come into consideration for generating an attenuation are transitions, transversions, insertions and deletions of at least one (1) base pair or nucleotide. Depending on the effect which the amino acid substitution elicited by the mutation has on the enzyme activity, reference is made to missense mutations or nonsense mutations. A missense mutation leads to the replacement of a given amino acid in a protein with another amino acid, with the amino acid replacement constituting, in particular, a nonconservative amino acid substitution. This substitution impairs the efficiency or activity of the protein and reduces it down to a value of from 0 to 75%, from 0 to 50%, from 0 to 25%, from 0 to 10%, or from 0 to 5%. A nonsense mutation leads to a stop codon being located in the coding region of the gene and consequently to translation being terminated prematurely. Insertions or deletions of at least one base pair in a gene lead to frame shift mutations which result in incorrect amino acids being incorporated or in the translation being terminated prematurely. If a stop codon is formed in the coding region as a consequence of mutation, this then also leads to translation being terminated prematurely.

Directions for generating such mutations belong to the prior art and are contained in known textbooks of genetics and molecular biology such as the textbook by Knippers ("Molekulare Genetik [Molecular Genetics]", 6$^{th}$ edition, Georg Thieme Verlag, Stuttgart, Germany, 1995), that by Winnacker ("Gene und Klone [Genes and Clones]", VCH Verlagsgesellschaft, Weinheim, Germany, 1990) or that by Hagemann ("Allgemeine Genetik [General Genetics]", Gustav Fischer Verlag, Stuttgart, 1986). Further measures are described in the prior art.

The isolated coryneform bacteria which are obtained by the measures of the invention exhibit a secretion or production of the desired amino acid, in a fermentation process, which is increased as compared with that of the starting strain or parent strain which was initially employed.

"Isolated bacteria" are to be understood as being the mutants and recombinant bacteria, in particular coryneform bacteria, according to the invention which are isolated or generated and which comprise a zwf allele which encodes a glucose 6-phosphate dehydrogenase which comprises the described amino acid substitution in position 321 of the amino acid sequence and, where appropriate, an amino acid substitution of L-serine with another proteinogenic amino acid, preferably L-threonine, in position 8.

The performance of the isolated bacteria, or of the fermentation process when using these bacteria, in regard to one or more of the parameters selected from the group comprising the product concentration (product per volume), the product yield (product formed per carbon source consumed) and the product formation (product formed per volume and time), or else of other process parameters and combinations, is improved by at least 0.5%, at least 1%, at least 1.5%, or at least 2%, based on the starting strain or parent strain or the fermentation process when using these strains.

The isolated coryneform bacteria according to the invention can be cultured continuously, as described, for example, in PCT/EP2004/008882, or discontinuously, in a batch process or a fed-batch process or a repeated fed-batch process, for the purpose of producing L-amino acids. A general summary of known culturing methods can be found in the textbook by Chmiel (Bioprozesstechnik 1. Einführung in die Bioverfahrenstechnik [Bioprocess Technology 1. Introduction to Bioprocess Technology] (Gustav Fischer Verlag, Stuttgart, 1991)) or in the textbook by Storhas (Bioreaktoren und periphere Einrichtungen [Bioreactors and Peripheral Equipment] (Vieweg Verlag, Brunswick/Wiesbaden, 1994)).

The culture medium or fermentation medium to be used must suitably satisfy the requirements of the given strains. Descriptions of media for culturing different microorganisms are given in the manual "Manual of Methods for General Bacteriology" published by the American Society for Bacteriology (Washington D.C., USA, 1981). The terms culture medium and fermentation medium or medium are mutually interchangeable.

The carbon source employed can be sugars and carbohydrates, such as glucose, sucrose, lactose, fructose, maltose, molasses, sucrose-containing solutions derived from sugar beet or sugar cane production, starch, starch hydrolysate and cellulose, oils and fats, such as soybean oil, sunflower oil, peanut oil and coconut oil, fatty acids, such as palmitic acid, stearic acid and linoleic acid, alcohols, such as glycerol, methanol and ethanol, and organic acids, such as acetic acid. These substances can be used individually or as mixtures.

The nitrogen source employed can be organic nitrogen-containing compounds, such as peptones, yeast extract, meat extract, malt extract, cornsteep liquor, soybean flour and urea, or inorganic compounds, such as ammonium sulfate, ammonium chloride, ammonium phosphate, ammonium carbonate and ammonium nitrate. The nitrogen sources can be used individually or as mixtures.

The phosphorus source employed can be phosphoric acid, potassium dihydrogen phosphate or dipotassium hydrogen phosphate or the corresponding sodium-containing salts.

The culture medium must furthermore contain salts, for example in the form of chlorides or sulfates of metals such as sodium, potassium, magnesium, calcium and iron, for example magnesium sulfate or iron sulfate, which are necessary for growth. Finally, essential growth substances, such as amino acids, for example homoserine, and vitamins, for example thiamine, biotin or pantothenic acid, can be used in addition to the abovementioned substances. In addition to this, suitable precursors of the respective amino acid can be added to the culture medium.

The abovementioned added substances can be added to the culture in the form of a once-only mixture or fed in a suitable manner during the culture.

Basic compounds such as sodium hydroxide, potassium hydroxide, ammonia or ammonia water, or acidic compounds such as phosphoric acid or sulfuric acid, are employed in a suitable manner for controlling the pH of the culture. In general, the pH is adjusted to a value of from 6.0 to 9.0, preferably of from 6.5 to 8. It is possible to use antifoamants, such as fatty acid polyglycol esters, for controlling foam formation. Suitable substances which act selectively, such as antibiotics, can be added to the medium in order to maintain the stability of plasmids. In order to maintain aerobic conditions, oxygen or oxygen-containing gas mixtures, such as air, are passed into the culture. It is also possible to use liquids which are enriched with hydrogen peroxide. Where appropriate, the fermentation is conducted under positive pressure, for example under a pressure of 0.03 to 0.2 MPa. The temperature of the culture is normally from 20° C. to 45° C., and preferably from 25° C. to 40° C. In the case of batch processes, the culture is continued until a maximum of the desired amino acid has been formed. This objective is normally achieved within from 10 hours to 160 hours. Longer culturing times are possible in the case of continuous processes.

Suitable fermentation media are described, inter alia, in U.S. Pat. Nos. 6,221,636, 5,840,551, 5,770,409, 5,605,818, 5,275,940 and 4,224,409.

Methods for determining L-amino acids are disclosed in the prior art. The analysis can, for example, take place by means of anion exchange chromatography, followed by ninhydrin derivatization, as described in Spackman et al. (Analytical Chemistry, 30 (1958), 1190), or it can take place by reversed phase HPLC, as described in Lindroth et al. (Analytical Chemistry (1979) 51: 1167-1174).

The invention accordingly relates to a process for preparing an L-amino acid, which comprises
a) fermenting an isolated coryneform bacterium in a suitable medium, said bacterium comprising a gene encoding a polypeptide having glucose 6-phosphate dehydrogenase enzyme activity, with the glycine in position 321 or the corresponding position in the amino acid sequences of said polypeptide having been replaced by a different proteinogenic amino acid, preferably L-serine, and with, where appropriate, the L-serine in position 8 or the corresponding position having been replaced with a different proteinogenic amino acid, preferably L-threonine, and
b) the L-amino acid being accumulated in the fermentation broth or in the cells of the isolated coryneform bacterium.

The fermentation broth which has been prepared in this way is then subjected to further processing into a solid or liquid product.

A fermentation broth is understood as being a fermentation medium in which a microorganism is cultured for a certain time and at a certain temperature. The fermentation medium, and/or the medium employed during the fermentation, contains/contain all the substances or components which ensure propagation of the microorganism and the formation of the desired amino acid.

At the conclusion of the fermentation, the resulting fermentation broth accordingly contains a) the biomass of the microorganism which has been formed as a consequence of the propagation of the cells of the microorganism, b) the desired amino acid which has been formed during the fermentation, c) the organic by-products which have been formed during the fermentation, and d) the constituents of the fermentation medium/fermentation media employed, or the added substances, for example vitamins, such as biotin, amino acids, such as homoserine, or salts, such as magnesium sulfate, which were not consumed by the fermentation.

The organic by-products include substances which are produced by the microorganisms employed in the fermentation, where appropriate in addition to the given desired L-amino acid, and are secreted, where appropriate. These by-products include L-amino acids which amount to less than 30%, 20% or 10% compared with the desired amino acid. They also include organic acids which carry from one to three carboxyl groups, such as acetic acid, lactic acid, citric acid, malic acid or fumaric acid. Finally, they also include sugars, such as trehalose.

Typical fermentation broths which are suitable for industrial purposes have an amino acid content of from 40 g/kg to 180 g/kg or of from 50 g/kg to 150 g/kg. In general, the content of biomass (as dry biomass) is from 20 to 50 g/kg.

In the case of the amino acid L-lysine, essentially four different product forms have been disclosed in the prior art.

One group of L-lysine-containing products comprises concentrated, aqueous, alkaline solutions of purified L-lysine (EP-B-0534865). Another group, as described, for example, in U.S. Pat. Nos. 6,340,486 and 6,465,025, comprises aqueous, acidic, biomass-containing concentrates of L-lysine-containing fermentation broths. The best-known group of solid products comprises pulverulent or crystalline forms of purified or pure L-lysine, which is typically present in the form of a salt such as L-lysine monohydrochloride. Another group of solid product forms is described, for example, in EP-B-0533039. The product form which is described in this document contains, in addition to L-lysine, the major portion of the added substances which were used during the fermentative preparation, and which were not consumed, and, where appropriate, from >0% to 100% of the biomass of the microorganism employed.

In correspondence with the different product forms, a very wide variety of methods are known for collecting, isolating or purifying the L-amino acid from the fermentation broth for the purpose of preparing the L-amino acid-containing product or the purified L-amino acid.

It is essentially ion exchange chromatography methods, where appropriate using active charcoal, and crystallization methods which are used for preparing solid, pure L-amino acids. In the case of lysine, this results in the corresponding base or a corresponding salt such as the monohydrochloride (Lys-HCl) or the lysine sulfate ($Lys_2$-$H_2SO_4$).

As far as lysine is concerned, EP-B-0534865 describes a method for preparing aqueous, basic L-lysine-containing solutions from fermentation broths. In this document, the biomass is separated off from the fermentation broth and discarded. A base such as sodium hydroxide, potassium hydroxide or ammonium hydroxide is used to adjust the pH to between 9 and 11. Following concentration and cooling, the mineral constituents (inorganic salts) are separated off from the broth by crystallization and either used as fertilizer or discarded.

In the case of processes for preparing lysine using the bacteria according to the invention, preference is given to those processes which result in products which contain constituents of the fermentation broth. These products are, in particular, used as animal feed additives.

Depending on the requirement, the biomass can be entirely or partially removed from the fermentation broth by means of separation methods such as centrifugation, filtration or decanting, or a combination of these methods, or all the biomass can be left in the fermentation broth. Where appropriate, the biomass, or the biomass-containing fermentation broth, is inactivated during a suitable process step, for example by means of thermal treatment (heating) or by means of adding acid.

In one approach, the biomass is completely or virtually completely removed, such that no (0%) or at most 30%, at most 20%, at most 10%, at most 5%, at most 1% or at most 0.1%, of the biomass remains in the prepared product. In another approach, the biomass is not removed, or only removed in trivial amounts, such that all (100%) or more than 70%, 80%, 90%, 95%, 99% or 99.9% of the biomass remains in the prepared product. In one process according to the invention, the biomass is accordingly removed in proportions of from $\geq 0\%$ to $\leq 100\%$.

Finally, the fermentation broth which is obtained after the fermentation can be adjusted, before or after the biomass has been completely or partially removed, to an acid pH using an inorganic acid, such as hydrochloric acid, sulfuric acid or phosphoric acid, or an organic acid, such as propionic acid (GB 1,439,728 or EP 1 331 220). It is likewise possible to acidify the fermentation broth when it contains the entire biomass (U.S. Pat. No. 6,340,486 or U.S. Pat. No. 6,465,025). Finally, the broth can also be stabilized by adding sodium bisulfite ($NaHSO_3$, GB 1,439,728) or another salt, for example an ammonium, alkali metal or alkaline earth metal salt of sulfurous acid.

Organic or inorganic solids which may be present in the fermentation broth are partially or entirely removed when the biomass is separated off. At least some (>0%), preferably at least 25%, particularly preferably at least 50%, and very particularly preferably at least 75%, of the organic by-products which are dissolved in the fermentation broth and the constituents of the fermentation medium (added substances), which are dissolved and not consumed remain in the product. Where appropriate, these by-products and constituents also remain completely (100%) or virtually completely, that is >95% or >98%, in the product. In this sense, the term "fermentation broth basis" means that a product comprises at least a part of the constituents of the fermentation broth.

Subsequently, water is extracted from the broth, or the broth is thickened or concentrated, using known methods, for example using a rotary evaporator, a thin-film evaporator or a falling-film evaporator, or by means of reverse osmosis or nanofiltration. This concentrated fermentation broth can then be worked up into flowable products, in particular into a finely divided powder or, preferably, a coarse-grained granulate, using methods of freeze drying, of spray drying or of spray granulation, or using other methods, for example in a circulating fluidized bed as described in PCT/EP2004/006655. Where appropriate, a desired product is isolated from the resulting granulate by means of screening or dust separation.

It is likewise possible to dry the fermentation broth directly, i.e. by spray drying or spray granulation without any prior concentration.

"Flowable" is understood as meaning powders which discharge unhindered from a series of glass discharge vessels having discharge apertures of different sizes, i.e. which discharge unhindered at least from the vessel having a 5 mm (millimeter) aperture (Klein: Seifen, Öle, Fette, Wachse [Soaps, Oils, Fats and Waxes] 94, 12 (1968)).

"Finely divided" means a powder the majority (>50%) of which has a particle size which is from 20 to 200 µm in diameter.

"Coarse-grained" means a product the majority (>50%) of which has a particle size of from 200 to 2000 µm in diameter.

The particle size can be determined using methods of laser diffraction spectrometry. The corresponding methods are described in the textbook "Teilchengrößenmessung in der Laborpraxis [Particle Size Measurement in Laboratory Practice]" by R. H. Müller and R. Schuhmann, Wissenschaftliche Verlagsgesellschaft Stuttgart (1996) or in the textbook "Introduction to Particle Technology" by M. Rhodes, Wiley & Sons (1998).

The flowable, finely divided powder can in turn be converted, by means of suitable compacting or granulating methods, into a coarse-grained, readily flowable, storable, and to a large extent dust-free, product.

The term "dust-free" means that the product only contains small proportions (<5%) of particle sizes of less than 100 µm in diameter.

Within the meaning of this invention, "storable" means a product which can be stored for at least one (1) year or longer, preferably at least 1.5 years or longer, particularly preferably two (2) years or longer, in a dry and cool environment without there being any significant loss (<5%) of the given amino acid.

The invention accordingly also relates to a process for preparing an L-amino acid-, preferably L-lysine- or L-tryptophan-, containing product, preferably an animal feed additive, from fermentation broths, which process is characterized by the steps of a) culturing and fermenting an L-amino acid-secreting coryneform bacterium, which comprises at least one zwf allele encoding a polypeptide having glucose 6-phosphate dehydrogenase activity, which polypeptide comprises an amino acid sequence in which any proteinogenic amino acid other than glycine, preferably L-serine, is present in position 321 or the comparable position, with, where appropriate, any proteinogenic amino acid other than L-serine, preferably L-threonine, being present in position 8 or the comparable position, in a fermentation medium, b) removing from 0 to 100% by weight of the biomass which is formed during the fermentation, and c) drying the fermentation broth which is obtained in accordance with a) and/or b) in order to obtain the product in the desired powder form or granulate form, with, where appropriate, an acid selected from the group sulfuric acid, phosphoric acid or hydrochloric acid being added prior to step b) or c).

Preference is given to water being removed (concentration) from the L-amino acid-containing fermentation broth after step a) or b).

It is advantageous to use customary organic or inorganic auxiliary substances, or carrier substances such as starch, gelatin, cellulose derivatives or similar substances, as are customarily used as binders, gelatinizers or thickeners in foodstuff or feedstuff processing, or other substances, such as silicic acids, silicates (EP0743016A) or stearates, in connection with the granulation or compacting.

It is furthermore advantageous to provide the surface of the resulting granulates with oils, as described in WO 04/054381. The oils which can be used are mineral oils, vegetable oils or mixtures of vegetable oils. Examples of these oils are soybean oil, olive oil and soybean oil/lecithin mixtures. In the same way, silicone oils, polyethylene glycols or hydroxyethyl cellulose are also suitable. Treating the surfaces with said oils increases the abrasion resistance of the product and reduces the dust content. The content of oil in the product is from 0.02 to 2.0% by weight, preferably from 0.02 to 1.0% by weight, and very particularly preferably from 0.2 to 1.0% by weight, based on the total quantity of the feedstuff additives.

Preference is given to products having a content of ≧97% by weight of a particle size of from 100 to 1800 μm, or a content of ≧95% by weight of a particle size of from 300 to 1800 μm, in diameter. The content of dust, i.e. particles having a particle size of <100 μm, is preferably from >0 to 1% by weight, particularly preferably at most 0.5% by weight.

Alternatively, however, the product can also be absorbed onto an organic or inorganic carrier substance which is known and customary in feedstuff processing, for example silicic acids, silicates, grists, brans, meals, starches, sugars etc., and/or be mixed and stabilized with customary thickeners or binders. Application examples and methods in this regard are described in the literature (Die Mühle+Mischfuttertechnik [The Grinding Mill+Mixed Feed Technology] 132 (1995) 49, page 817).

Finally, the product can also be brought, by means of coating methods using film formers such as metal carbonates, silicic acids, silicates, alginates, stearates, starches, rubbers and cellulose ethers, as described in DE-C-4100920, into a state in which it is stable towards digestion by animal stomachs, in particular the ruminant stomach.

In order to set a desired amino acid concentration in the product, the appropriate amino acid can, depending on the requirement, be added during the process in the form of a concentrate or, where appropriate, of a largely pure substance or its salt in liquid or solid form. The latter can be added individually, or as mixtures, to the resulting fermentation broth, or to the concentrated fermentation broth, or else be added during the drying process or granulation process.

In the case of lysine, the ratio of the ions is adjusted during the preparation of lysine-containing products such that the ion ratio in accordance with the following formula

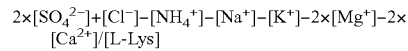

has a value of from 0.68 to 0.95, preferably of from 0.68 to 0.90, as described by Kushiki et al. in US 20030152633.

In the case of lysine, the solid fermentation broth-based product which has been prepared in this way has a lysine content (as lysine base) of from 10% by weight to 70% by weight or of from 20% by weight to 70% by weight, preferably of from 30% by weight to 70% by weight and very particularly preferably of from 40% by weight to 70% by weight, based on the dry mass of the product. It is also possible to achieve maximum contents of lysine base of 71% by weight, 72% by weight or 73% by weight.

In the case of an electrically neutral amino acid such as L-tryptophan, the solid fermentation broth-based product which has been prepared in this way has an amino acid content of at least 5% by weight, 10% by weight, 20% by weight or 30% by weight and maximally 50% by weight, 60% by weight, 70% by weight, 80% by weight, 90% by weight or up to 95% by weight.

The water content of the solid product is up to 5% by weight, preferably up to 4% by weight, and particularly preferably less than 3% by weight.

A mutant of *Corynebacterium glutamicum* which is designated DM1797 and which comprises the amino acid substitution lysC T311I in its aspartate kinase was deposited on Oct. 28, 2004 with the Deutsche Sammlung für Mikroorganismen und Zellkulturen [German Collection of Microorganisms and Cell Cultures] (DSMZ, Brunswick, Germany) as DSM 16833.

The *Corynebacterium glutamicum* mutant DM1816 of the invention, which comprises L-serine in position 321 in the amino acid sequence of the Zwf polypeptide, was deposited on Feb. 9, 2005 at the Deutsche Sammlung für Mikroorganismen und Zellkulturen [German Collection of Microorganisms and Cell Cultures] (DSMZ, Brunswick, Germany) as DSM17119.

EXAMPLE 1

Mutagenesis of the L-Lysine-Producing Strain DM1797

The *Corynebacterium glutamicum* strain DM1797 was used as a starting strain for mutagenesis with N-methyl-N'-nitro-N-nitrosoguanidine (MNNG). The DM1797 strain is an aminoethylcysteine-resistant mutant of *Corynebacterium glutamicum* ATCC13032 and has been deposited under the name DSM16833 with the Deutsche Sammlung für Mikroorganismen und Zellkulturen (DSMZ, Brunswick, Germany).

The DM1797 strain was cultured in 10 ml of LB broth (Merck, Darmstadt, Germany) contained in a 100 ml Erlenmeyer flask on a Certomat BS-1 rotary shaker (B. Braun Biotech International, Melsungen, Germany) at 33° C. and 200 rpm for 24 hours. The culture was subsequently removed by centrifugation, the sediment was resuspended in 10 ml of 0.9% NaCl solution, the suspension obtained was again removed by centrifugation and the sediment obtained was taken up in 10 ml of 0.9% NaCl solution. 5 ml of this cell suspension were treated with 400 μg/ml MNNG on a shaker (see above) at 30° C. and 200 rpm for 15 minutes. The mutagenesis mixture was subsequently removed by centrifugation and the sediment was taken up in 10 ml of 2% sodium thiosulfate in 0.9% NaCl buffer (pH=6.0). The cell suspension was then diluted 1:1000, 1:10000 and 1:100000 with 0.9% NaCl solution, and aliquots were plated on brain-heart agar (Merck, Darmstadt, Germany). Approximately 2500 mutants were isolated in this way.

EXAMPLE 2

Performance Test of the DM1797 Strain Mutants

The mutants obtained in example 1 were cultured in a nutrient medium suitable for lysine production, and the lysine content was determined in the culture supernatant.

For this purpose, the clones were first propagated on brain-heart agar plates (Merck, Darmstadt, Germany) at 33° C. for 24 hours. Starting from these agar plate cultures, in each case a preculture was inoculated (10 ml of medium in a 100 ml Erlenmeyer flask). The medium used for said preculture was MM medium. The preculture was incubated on a shaker at 33° C. and 240 rpm for 24 hours. From this preculture, a main culture was inoculated in such a way that the starting OD (660 nm) of said main culture was 0.1 OD. The MM medium was likewise used for the main culture.

| Medium MM | |
|---|---|
| CSL | 5 g/l |
| MOPS | 20 g/l |
| Glucose (autoclaved separately) | 50 g/l |
| Salts: | |
| (NH$_4$)$_2$SO$_4$) | 25 g/l |
| KH$_2$PO$_4$ | 0.1 g/l |
| MgSO$_4$ * 7 H$_2$O | 1.0 g/l |
| CaCl$_2$ * 2 H$_2$O | 10 mg/l |
| FeSO$_4$ * 7 H$_2$O | 10 mg/l |
| MnSO$_4$ * H$_2$O | 5.0 mg/l |
| Biotin (sterile-filtered) | 0.3 mg/l |

-continued

| | |
|---|---|
| Thiamin * HCl (sterile-filtered) | 0.2 mg/l |
| CaCO₃ | 25 g/l |

CSL (corn steep liquor), MOPS (morpholinopropanesulfonic acid) and the salt solution were adjusted to pH 7 with aqueous ammonia and autoclaved. Subsequently, the sterile substrate and vitamin solutions and the dry-autoclaved CaCO$_3$ were added.

Culturing took place in volumes of 10 ml contained in 100 ml Erlenmeyer flasks with baffles. The temperature was 33° C., the number of revolutions per minute was 250 rpm and the humidity was 80%.

After 24 hours, the optical density (OD) was determined at a measuring wavelength of 660 nm using a Biomek 1000 device (Beckmann Instruments GmbH, Munich, Germany). The amount of lysine formed was determined by ion exchange chromatography and post-column derivatization with ninhydrin detection, using an amino acid analyzer from Eppendorf-BioTronik (Hamburg, Germany). A mutant distinguished by an increased lysine formation was referred to as DM1816.

TABLE 1

| Strain | OD (660) | Lysine-HCl (g/l) |
|---|---|---|
| DM1797 | 11.7 | 3.6 |
| DM1816 | 11.8 | 3.9 |

EXAMPLE 3

Sequencing of the zwf Gene of the DM1816 Mutant

Chromosomal DNA was isolated from the DM1816 clone by the method of Eikmanns et al. (Microbiology 140: 1817-1828 (1994)). A DNA section carrying the zwf gene was amplified with the aid of the polymerase chain reaction. To this end, the following oligonucleotides were used as primers:

```
zwf-L1 (SEQ ID NO:19):
5' agaagctgac gctgtgttct 3' zwf-L2 (SEQ ID NO:20):
5' cattggtgga ctcggtaact 3'
```

The primers depicted were synthesized by MWG Biotech (Ebersberg, Germany). They enable an approx. 1.95 kb DNA section carrying the zwf gene to be amplified. The zwf-L1 primer binds to the region corresponding to positions 59 to 78 of the strand complementary to SEQ ID NO:3. The zwf-L2 primer binds to the region corresponding to positions 2026 to 2007 of the strand according to SEQ ID NO:3.

The PCR reaction was carried out using the Phusion High Fidelity DNA polymerase (New England Biolabs, Frankfurt, Germany). The reaction mixture was prepared according to the manufacturer's instructions and contained in a total volume of 50 µl 10 µl of the supplied 5×Phusion HF buffer, deoxynucleoside triphosphates, in each case in a concentration of 200 µM, primers in a concentration of 0.5 µM, approximately 50 ng of template DNA and 2 units of Phusion polymerase. The volume was adjusted to 50 µl by adding H$_2$O.

The PCR mixture was first subjected to an initial denaturation at 98° C. for 30 seconds. This was followed by 35 repeats of a denaturation step at 98° C. for 20 seconds, a step of binding the primers to the initially introduced DNA at 60° C. for 20 seconds and the extension step of extending the primers at 72° C. for 60 seconds. After the final extension step of 5 minutes at 72° C., the PCR mixture was subjected to an agarose gel electrophoresis (0.8% agarose). An approx. 1.85 kb DNA fragment was identified, isolated from the gel and purified using the QIAquick Gel Extraction Kit from Qiagen, (Hilden, Germany).

The nucleotide sequence of the amplified DNA fragment and PCR product, respectively, was determined by Agowa (Berlin, Germany). The sequence obtained of the coding region of the zwf allele is depicted in SEQ ID NO:9. The amino acid sequence of the protein, established with the aid of the Patentin program, is depicted in SEQ ID NO:10.

The nucleotide sequence of the coding region of the zwf allele of the DM1816 mutant comprises the nucleobase adenine in position 961 (see SEQ ID NO:5 or 9). The wild type gene (see SEQ ID NO:1) comprises the nucleobase guanine in this position. This guanine-adenine transition results in an amino acid substitution of serine for glycine in position 321 of the resulting amino acid sequence. This mutation is referred to as zwfG321S hereinbelow. The zwf allele of DM1816 furthermore also comprises the nucleotide substitution of thymine with adenine in position 22 of the nucleotide sequence. This thymine-adenine transversion results in an amino acid substitution of threonine for serine in position 8 of the resulting amino acid sequence.

Moreover, the zwf allele of DM1816 also comprises another five nucleotide substitutions which do not result in an amino acid substitution ("silent mutations"): a cytosine-thymine transition in position 138, a cytosine-thymine transition in position 279, a thymine-cytosine transition in position 738, a cytosine-thymine transition in position 777 and a guanine-adenine transition in position 906.

EXAMPLE 4

Construction of the Exchange Vector pK18mobsacB_zwfG321S

A part of the coding region, i.e. an "internal fragment" or "internal region", of the zwf allele, which carries the mutation zwfG321S, was amplified with the aid of the polymerase chain reaction. The template used was the chromosomal DNA obtained in example 3. The following oligonucleotides were selected as primers for the PCR:

```
zwf-int1-bam (SEQ ID NO:23):
5' ctag-ggatcc-acgtacgcgatgccgcaagt 3' zwf-int2-bam (SEQ ID NO:24):
5' ctag-ggatcc-tcaggctgcacgcgaatcac 3'
```

They were synthesized by MWG Biotech (Ebersberg, Germany) and enable an approx. 1 kb DNA section of the coding region to be amplified. The nucleotides 11 to 30 of the zwf-int1-bam primer bind to the region corresponding to positions 546 to 565 of the strand complementary to SEQ ID NO:3. The positions 546 and 565 of SEQ ID NO:3 correspond to positions 239 and 258 in SEQ ID NO:1. The nucleotides 11 to 30 of the zwf-int2-bam primer bind to the region corresponding to positions 1527 to 1508 of the strand according to SEQ ID NO:3. The positions 1527 and 1508 of SEQ ID NO:3 correspond to positions 1220 and 1201 of SEQ ID NO:1. The primers moreover comprise the sequences for cleavage sites of the restriction endonuclease BamHI, which are indicated by underscoring in the nucleotide sequence depicted above.

The PCR reaction was carried out using the Phusion High-Fidelity DNA polymerase (New England Biolabs, Frankfurt, Germany). The reaction mixture was composed as described above. The PCR was carried out as above, with one exception: the 72° C. extension step in the 35 repeats was carried out in each case only for 30 seconds.

The approx. 1 kb amplicon was treated with the BamHI restriction endonuclease and identified by electrophoresis in a 0.8% strength agarose gel. It was subsequently isolated from the gel and purified using the QIAquick Gel Extraction Kit from Qiagen.

The DNA fragment purified in this way comprises the zwfG321S mutation described and has BamHI-compatible ends (zwfG321S fragment and, respectively, 'zwf' in FIG. 1). It was then incorporated into the mobilizable pK18mobsacB vector described by Schafer et al. (Gene, 145, 69-73 (1994)), in order to enable an allele or mutation exchange. To this end, pK18mobsacB was digested with the BamHI restriction enzyme and the ends were dephosphorylated by alkaline phosphatase (Alkaline Phosphatase, Boehringer Mannheim, Germany). The thus prepared vector was mixed with the zwfG321S fragment, and the mixture was treated with the Ready-To-Go T4 DNA Ligase Kit (Amersham-Pharmacia, Freiburg, Germany).

The ligation mixture was then used to transform the *E. coli* strain S17-1 (Simon et al., Bio/Technologie 1: 784-791, 1993) (Hanahan, In. DNA cloning. A practical approach. Vol. 1. ILR-Press, Cold Spring Harbor, N.Y., 1989). Selection for plasmid-harboring cells was carried out by plating the transformation mixture on LB agar (Sambrock et al., Molecular Cloning: a laboratory manual. $2^{nd}$ Ed. Cold Spring Harbor, N.Y., 1989) which had been supplemented with 25 mg/l kanamycin.

Plasmid DNA was isolated from a transformant with the aid of the QIAprep Spin Miniprep Kit from Qiagen and checked by restriction cleavage, in each case once with the enzyme BamHI and once with the enzyme SacI, and subsequent agarose gel electrophoresis. The plasmid was named pK18mobsacB_zwfG321S and is depicted in FIG. 1.

EXAMPLE 5

Incorporation of the zwfG321S Mutation into the DM1797 Strain

The pK18mobsacB_zwfG321S vector described in example 4 was transferred by way of conjugation into the *C. glutamicum* strain DM1797 according to the protocol by Schäfer et al. (Journal of Microbiology 172: 1663-1666 (1990)). The vector cannot self-replicate in DM1797 and remains in the cell only when integrated in the chromosome as a result of a recombination event. The selection of transconjugants, i.e. of clones with integrated pK18mobsacB_zwfG321S, was carried out by plating the conjugation mixture on LB agar which had been supplemented with 25 mg/l kanamycin and 50 mg/l nalidixic acid. Kanamycin-resistant transconjugants were then streaked out on LB agar plates supplemented with kanamycin (25 mg/l) and incubated at 33° C. for 24 hours. Mutants in which the plasmid had been excised as a result of a second recombination event were selected by culturing the clones non-selectively in LB liquid medium for 30 hours, then streaking them out on LB agar which had been supplemented with 10% sucrose and incubating at 33° C. for 24 hours.

Like the pK18mobsacB starting plasmid, the pK18mobsacB_zwfG321S plasmid comprises, in addition to the kanamycin resistance gene, a copy of the sacB gene coding for *Bacillus subtilis* levan sucrase. Sucrose-inducible expression of the sacB gene results in the formation of levan sucrase which catalyzes the synthesis of the product levan which is toxic to *C. glutamicum*. Therefore, only those clones in which the integrated pK18mobsacB_zwfG321S has been excised as the result of a second recombination event grow on sucrose-supplemented LB agar. Depending on the location of the second recombination event with respect to the site of mutation, the excision causes the allele exchange or incorporation of the mutation, or the original copy remains in the chromosome of the host.

Subsequently, a clone was looked for in which the desired exchange, i.e. incorporation of the zwfG321S mutation, had taken place. To this end, the sequence of the zwf gene of 10 clones having the phenotype "growth in the presence of sucrose" and "no growth in the presence of kanamycin" was determined. In this way, a clone harboring the zwfG321S mutation was identified. This strain was referred to as *C. glutamicum* DM1797_zwfG321S.

EXAMPLE 6

Comparison of the Performance of the DM1797_zwfG321S Strain With that of the DM1797 Starting Strain The performance test was carried out as described in example 2. The DM1797_zwfG321S strain displayed, in comparison with DM1797, a markedly increased secretion of lysine, similar to DM1816 (see table 1).

What is claimed is:

1. An isolated polynucleotide encoding a polypeptide of coryneform bacteria having glucose 6-phosphate dehydrogenase enzyme activity, wherein said polypeptide comprises the amino acid sequence of SEQ ID NO:2, except that any proteinogenic amino acid other than glycine is present at position 321 and/or any proteinogenic amino acid other than serine is present at position 8.

2. The isolated polynucleotide of claim 1, wherein said isolated polynucleotide comprises the nucleotide sequence of SEQ ID NO:1, except that the codon for the amino acid in position 321 of the protein encoded is for any proteinogenic amino acid other than glycine and/or the codon for the amino acid at position 8 is for any proteinogenic amino acid other than serine.

3. The isolated polynucleotide of claim 1, wherein, except for the amino acids at positions 321 and 8, said polypeptide consists of the amino acid sequence of SEQ ID NO:2.

4. The isolated polynucleotide of claim 1, wherein said polypeptide is 514 amino acids in length.

5. The isolated polynucleotide of claim 1, wherein the amino acid at position 321 of said polypeptide is L-serine.

6. The isolated polynucleotide of claim 1, wherein the amino acid at position 8 of said polypeptide is L-threonine.

7. The isolated polynucleotide of claim 1, wherein the amino acid at position 321 of said polypeptide is L-serine and the amino acid at position 8 of said polypeptide is L-threonine.

8. The isolated polynucleotide of claim 1, wherein said isolated polynucleotide comprises the nucleotide sequence of SEQ ID NO:5, SEQ ID NO:7 or SEQ ID NO:9.

9. The isolated polynucleotide of claim 1, wherein said isolated polynucleotide comprises the nucleotide sequence of SEQ ID NO:11.

10. A vector comprising the nucleotide sequence of the isolated polynucleotide of claim 1.

11. An isolated coryneform bacterium comprising a polynucleotide sequence encoding a polypeptide comprising the amino acid sequence of SEQ ID NO:2 except that any proteinogenic amino acid other than glycine is present at position 321 and/or any proteinogenic amino acid other than serine is present at position 8, and wherein said polypeptide has glucose 6-phosphate dehydrogenase activity.

12. The isolated coryneform bacterium of claim 11, wherein said polypeptide comprises an amino acid sequence having a length of 514 amino acids.

13. The isolated coryneform bacterium of claim 12, wherein said isolated coryneform bacterium is selected from the group consisting of *Corynebacterium efficiens*, *Corynebacterium glutamicum*, *Corynebacterium thermoaminogenes* and *Corynebacterium aminogenes*.

14. A process for preparing an L-amino acid, comprising:
a) fermenting a coryneform bacterium in a suitable medium, said coryneform bacterium comprising the isolated polynucleotide of claim 1;
b) concentrating the L-amino acid in the fermentation broth or in the cells of said bacterium.

15. The process of claim 14, wherein said polypeptide comprises an amino acid sequence having a length of 514 amino acids.

16. The process of claim 14, wherein said L-amino acid is purified from the fermentation broth or cells of step b).

17. The process of claim 14, further comprising:
c) concentrating said L-amino acid in said fermentation broth in step b, collecting said fermentation broth and then removing an amount of from 0 to 100% of the biomass present; and
d) preparing from the composition produced in step c, an essentially dry and shaped product by a method selected from the group consisting of granulation, compacting, spray drying and extrusion.

18. The process of claim 17, wherein the essentially dry and shaped product obtained in step d) is sprayed with an oil.

19. The process of claim 14, wherein said L-amino acid is either L-lysine or L-tryptophan.

20. The vector of claim 10, wherein, except for the amino acids at positions 321 and 8, said polypeptide consists of the amino acid sequence of SEQ ID NO:2.

21. A coryneform bacterium comprising the vector of claim 20.

* * * * *